(12) United States Patent
Pulé et al.

(10) Patent No.: US 10,588,967 B2
(45) Date of Patent: Mar. 17, 2020

(54) CHIMERIC ANTIGEN RECEPTOR (CAR) SIGNALLING SYSTEM

(71) Applicant: UCL BUSINESS PLC, London (GB)

(72) Inventors: Martin Pulé, London (GB); Shaun Cordoba, London (GB); Khai Kong, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/301,148

(22) PCT Filed: Mar. 31, 2015

(86) PCT No.: PCT/GB2015/050974
§ 371 (c)(1),
(2) Date: Sep. 30, 2016

(87) PCT Pub. No.: WO2015/150771
PCT Pub. Date: Oct. 8, 2015

(65) Prior Publication Data
US 2017/0014508 A1    Jan. 19, 2017

(30) Foreign Application Priority Data
Apr. 1, 2014    (GB) .................................. 1405845.7

(51) Int. Cl.
| | | |
|---|---|---|
| *A61K 39/395* | (2006.01) | |
| *C07K 16/28* | (2006.01) | |
| *A61K 38/17* | (2006.01) | |
| *C07K 14/725* | (2006.01) | |
| *C12N 5/0783* | (2010.01) | |
| *A61K 31/166* | (2006.01) | |
| *A61K 31/436* | (2006.01) | |
| *A61K 31/4545* | (2006.01) | |
| *A61K 38/45* | (2006.01) | |
| *A61K 38/52* | (2006.01) | |
| *C07K 14/705* | (2006.01) | |
| *C12N 9/12* | (2006.01) | |
| *C12N 9/90* | (2006.01) | |
| *C12N 5/10* | (2006.01) | |
| *A61K 48/00* | (2006.01) | |
| *C07K 14/47* | (2006.01) | |

(52) U.S. Cl.
CPC ........ *A61K 39/3955* (2013.01); *A61K 31/166* (2013.01); *A61K 31/436* (2013.01); *A61K 31/4545* (2013.01); *A61K 38/177* (2013.01); *A61K 38/1774* (2013.01); *A61K 38/45* (2013.01); *A61K 38/52* (2013.01); *A61K 48/00* (2013.01); *C07K 14/4702* (2013.01); *C07K 14/705* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 16/2803* (2013.01); *C12N 5/0636* (2013.01); *C12N 5/0646* (2013.01); *C12N 5/10* (2013.01); *C12N 9/12* (2013.01); *C12N 9/90* (2013.01); *C12Y 207/11001* (2013.01); *C12Y 502/01008* (2013.01); *C07K 2317/622* (2013.01); *C07K 2319/00* (2013.01); *C07K 2319/02* (2013.01); *C07K 2319/03* (2013.01); *C07K 2319/70* (2013.01); *C07K 2319/74* (2013.01)

(58) Field of Classification Search
CPC ............ C07K 2319/00; C07K 2319/70; C07K 2319/74; C07K 2319/75
See application file for complete search history.

(56) References Cited

U.S. PATENT DOCUMENTS

| | | | | |
|---|---|---|---|---|
| 4,208,479 A | * | 6/1980 | Zuk ...................... | C07J 41/0016 435/7.72 |
| 2013/0280285 A1 | | 10/2013 | Schoenfeld et al. | |
| 2014/0005076 A1 | | 1/2014 | Gurney et al. | |

(Continued)

FOREIGN PATENT DOCUMENTS

| | | |
|---|---|---|
| WO | WO 2016/030691 | 3/1916 |
| WO | WO 2016/124930 | 8/1916 |

(Continued)

OTHER PUBLICATIONS

Sirolimus—MeSH—NCBI (https://www.ncbi.nlm.nih.gov/mesh/68020123,1999, downloaded Jun. 18, 2018) (Year: 1999).*

(Continued)

*Primary Examiner* — Peter J Reddig
(74) *Attorney, Agent, or Firm* — Marshall, Gerstein & Borun LLP

(57) ABSTRACT

The present invention relates to a chimeric antigen receptor (CAR) signalling system comprising; (i) a receptor component comprising an extracellular antigen-binding domain, a transmembrane domain and a intracellular first chemical inducer of dimerization binding domain 1 (CBD1); and (ii) an intracellular signalling component comprising a signalling domain and a second chemical inducer of dimerization binding domain 2 (CBD2); wherein CBD1 and CBD2 are capable of simultaneously binding to a chemical inducer of dimerization (CID); wherein, in the absence of the CID, binding of the antigen-binding component to antigen does not result in signalling through the signalling component; whilst, in the presence of the CID, the receptor component and the signalling component heterodimerize and binding of the antigen-binding domain to antigen results in signalling through the signalling domain.

24 Claims, 10 Drawing Sheets
Specification includes a Sequence Listing.

(56) References Cited

U.S. PATENT DOCUMENTS

| | | | |
|---|---|---|---|
| 2016/0311907 A1* | 10/2016 | Brogdon | C07K 14/7051 |
| 2017/0014508 A1 | 1/2017 | Pule et al. | |
| 2017/0081411 A1 | 3/2017 | Engels et al. | |
| 2017/0260269 A1 | 9/2017 | Pule et al. | |
| 2018/0016335 A1 | 1/2018 | Pule et al. | |
| 2018/0042963 A1 | 2/2018 | Wu et al. | |
| 2018/0050065 A1 | 2/2018 | Pule et al. | |

FOREIGN PATENT DOCUMENTS

| | | |
|---|---|---|
| WO | WO-2012/099973 A2 | 7/2012 |
| WO | WO-2014/127261 A1 | 8/2014 |
| WO | 2014/184143 A1 | 11/2014 |
| WO | WO 2015/142661 | 9/2015 |
| WO | 2015/150771 A1 | 10/2015 |
| WO | 2017/137758 A1 | 8/2017 |
| WO | 2017/137759 A1 | 8/2017 |
| WO | 2017/216562 A1 | 12/2017 |

OTHER PUBLICATIONS

Szymczak et al. (Nat. Biotech. May 2004 22(5): 589-594) (Year: 2004).*

Lanitis et al. (Cancer Immunology Res. Apr. 7, 2013 1(1): 43-53) (Year: 2013).*

Bayle et al., Rapamycin analogs with differential binding specificity permit orthogonal control of protein activity. Chem Biol. 13: 99-107 (2006).

Belshaw et al., Controlling protein association and subcellular localization with a synthetic ligand that induces heterodimerization of proteins. Proc. Natl. Acad. Sci. USA. 93(10): 4604-7 (1996).

Clackson et al., Redesigning an FKBP-lingand interface to generate chemical dimerizers with novel specificity. Proc. Natl. Acad. Sci. USA, 95(18): 10437-42 (1998).

Farrar et al., Activation of the Raf-1 kinase cascade by coumermycin= induced dimerization. Nature, 383: 178-81 (1996).

Farrar et al., Coumermycin-induced dimerization of GyrB-containing fusion proteins. Methods Enzymol. 327: 421-9 (2000).

Gendreizig et al., Induced protein dimerization in vivo through covalent labeling. J. Am. Chem. Soc. 125(49): 14970-1 (2003).

Hussey et al., Synthesis of a beta-estradiol-biotin chimera that potently heterodimerizes estrogen receptor and streptavidin proteins in a yeast three-hybrid system. J. Am. Chem. Soc. 125(13): 3692-3 (2003).

Huye et al., Combining mTor inhibitors with rapamycin-resistant T cells: A two-pronged approach to tumor elimination. Molec. Ther. 19(12): 2239-48 (2011).

Jensen et al., Design and implementation of adoptive therapy with chimeric antigen receptor-modified T cells. Immuno. Rev. 257: 127-44 (2013).

Lin et al., Dexamethasone-Methotrexate: An efficient chemical inducer of protein dimerization in vivo. J. Am. Chem. Soc. 122: 4247-8 (2000).

Muddana et al., Facile synthesis of cids: biotinylated estrone oximes efficiently heterodimerize estrogen receptor and streptavidin proteins in yeast three hybrid systems. Org. Lett. 6(9): 1409-12 (2004).

Rivera et al., A humanized system for pharmacologic control of gene expression. Nat. Med. 2(9): 1028-32 (1996).

International Preliminary Report on Patentability prepared for PCT/GB2015/050974 by European Patent Office, dated Oct. 4, 2016.

U.S. Appl. No. 15/506,383, filed Feb. 24, 2017.

U.S. Appl. No. 15/548,340, filed Aug. 2, 2017.

Amrolia et al, Chimeric antigen receptor T cells for ALL, Lancet. 385(9967):488-490 (2015).

Budde et al., Combining a CD20 chimeric antigen receptor and an inducible caspase 9 suicide switch to improve the efficacy and safety of T cell adoptive immunotherpay for lymphoma, PLOS One. 8(12):e82742 (2013).

Call et al., Common themes in the assembly and architecture of activating immune receptors, Nature Review Immunology. 7:841-850 (2007).

Casucci et al., Suicide Gene Therapy to increase the safety of chimeric antigen receptor-redirected T Lymphocytes, Journal of Cancer. 2:378-382 (2011).

Chang et al., A general method for facilitating heterodimeric pairing between two proteins: application to expression of alpha and beta T-cell receptor extracellular segments, Proc. Natl. Acad. Sci. USA. 91:11408-11412 (1994).

Chicaybam et al., A conditional system for the activation of lymphocytes expressing activating and inhibitory CARs, Hum. Gene Ther. 21:1418 (2010).

Chicaybam et al., Constructions and validation of an activating and inhibitory chimeric antigen receptor (CAR) system, Cancer Research. 74(Suppl 19):Abstract #2797 (2014).

Cordoba et al., Chimeric Antigen Receptor Logical and Gate Based on CD45/CD148 Phosphatases, Mol. Ther. 22(Suppl.):S59 (2014).

Davila et al, Efficacy and toxicity management of 19-28z CAR T cell therapy in B cell acute lymphoblastic leukemia, Sci. Transl. Med. 6(224):224ra25, 23 pages (2014).

Deyev et al. Design of multivalent complexes using the barnase*barstar module, Nat. Biotechnol. 21:1486-1492 (2003).

Donnelly et al., The 'cleavage' activities of foot-and-mouth disease virus 2A site-directed mutants and naturally occurrina '2A-like' sequences, J. Gen. Viral. 82: 1027-41 (2001 ).

Dotti et al., Design and Development of Therapies using Chimeric Antigen Receptor-Expressing T cells, Immunol. Rev. 257:1-30 (2014).

Fedorov et al., Inhibitory Chimeric Antigen Receptors (iCARs) Limit Undersirable Side Effects of T-Cell Therapies, Experimental Hematology, 42nd Annual Scientific Meeting of the ISEH—Society for Hematology and Stem Cells, 41(2):Abstract S75 (2013).

Fedorov et al., PD-1- and CTLA-4-Based Inhibitory Chimeric Antigen Receptors (iCARs) Divert Off-Target Immunotherapy Responses, Sci. Transl. Med. 5(215):215ra172 (2013).

International Preliminary Report on Patentability received for PCT Patent Application No. PCT/GB2015/052494, dated Mar. 9, 2017, 8 pages.

International Preliminary Report on Patentability received for PCT Patent Application No. PCT/GB2016/050257, dated Aug. 17, 2017, 7 pages.

International Search Report and Written Opinion received for PCT Patent Application No. PCT/GB2015/050974, dated Jun. 8, 2015, 10 pages.

International Search Report and Written Opinion received for PCT Patent Application No. PCT/GB2016/050257, dated May 13, 2016, 10 pages.

International Search Report and Written Opinion, International Application No. PCT/GB2015/052494, dated Oct. 14, 2015.

Janus et al., The mammalian target of the rapamycin (mTOR) kinase pathway: its role in tumourigenesis and targeted antitumour therapy, Cell Mol. Biol. Lett. 10:479-98 (2005).

Jena et al, Redirecting T-cell specificity by introducing a tumor-specific chimeric antgen receptor, Blood. 116(7):1035-1044 (2010).

Kershaw et al., Clinical application of genetically modified T cells in cancer therapy, Clinical Translation Immunology. 3:e16 (2014).

Klotzsche et al., A peptide triggers allostery in tet repressor by binding to a unique site, J. Biol. Chem. 280:24591-9 (2005).

Klotzsche et al., Efficient and exclusive induction of Tet repressor by the oligopeptide Tip results from co-variation of their interaction site, Nucleic Acids Research. 35(12):3945-3952 (2007).

Kochenderfer et al, Chemotherapy-refractory diffuse large B-cell lymphoma and indolent B-cell malignancies can be effectively treated with autologous T cells expressing an anti-CD19 chimeric antigen receptor, J. Clin. Oncol. 33(6):540-549 (2015).

Luckner et al., How an agonist peptide mimics the antibiotic tetracycline to induce Tet-repressor, J. Molec. Biol. 368:780-90 (2007).

Maude et al, Chimeric antigen receptor T cells for sustained remissions in leukemia, N. Engl. J. Med. 371(16):1507-1517 (2014).

(56) References Cited

OTHER PUBLICATIONS

Ramos et al., Chimeric antigen receptor (CAR)-engineered lymphocytes for cancer therapy, Expert Opin. Biol. Ther. 11(7):855-873 (2011).
Rossi et al., Stably tethered multifunctional structures of defined composition made by the dock and lock method for use in cancer targeting, Proc. Natl. Acad. Sci. USA. 103: 6841-6 (2006).
Rossi et al., The dock-and-lock method combines recombinant engineering with site-specific covalent conjugation to generate multifunctional structures, Bioconjugate Chem. 23:309-323 (2011).
White et al., Protein-protein interactions as targets for small-molecule therapeutics in cancer, Expert Rev. Mol. Med. 10:e8 (2008).
Wilkie et al., Dual Targeting of ErbB2 and MUC1 in Breast Cancer Using Chimeric Antigen Receptors Engineered to Provide Complementary Signaling, J. Clin. Immunol. 32:1059-1070 (2012).

* cited by examiner (a)

(b)

(a)

(b)

(c)

CHIMERIC ANTIGEN RECEPTOR (CAR) SIGNALLING SYSTEM

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 49455_Seq-Listing.txt; Size: 62,779 bytes; Created: Sep. 28, 2016.

FIELD OF THE INVENTION

The present invention relates to an antigen receptor signalling system.

BACKGROUND TO THE INVENTION

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T-cells specific to any surface antigen by ex vivo viral vector transduction of a bulk population of peripheral blood T-cells.

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common forms of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

A number of toxicities have been reported from CAR studies, and additional theoretical toxicities exist. Such toxicities include immunological toxicity caused by sustained intense activation of the CAR T-cells resulting in a macrophage activation syndrome (MAS) and "On-target off-tumour" toxicity i.e. recognition of the target antigen on normal tissues.

MAS is presumed to be caused by persistent antigen-driven activation and proliferation of T-cells which in turn release copious inflammatory cytokines leading to hyper-activation of macrophages and a feed-forward cycle of immune activation. A large spike in serum IL-6 is characteristic and the syndrome can result in a severe systemic illness requiring ICU admission.

On-target off-tumour toxicity has been reported with other CARs, for example a group of patients treated with a CAR against the renal cell carcinoma antigen CAIX developed unexpected and treatment limiting biliary toxicity. Two fatalities have been reported with CAR studies: one patient died of a respiratory distress syndrome which occurred immediately post-infusion of a large dose of 3rd generation anti-ERBB2 CAR T-cells; a further patient died in a different study after a possible cytokine storm following treatment of CLL with a second generation anti-CD19 CAR.

These toxicities are very difficult to predict even with detailed animal studies or non-human primate work. Crucially, unlike small molecules and biologics, CAR T-cells do not have a half-life and one cannot cease administration and wait for the agent to breakdown/become excreted. CAR T-cells are autonomous and can engraft and proliferate. Toxicity can therefore be progressive and fulminant.

Suicide genes are genetically expressed elements which can conditionally destroy cells which express them. Examples include Herpes-simplex virus thymidine kinase, which renders cells susceptible to Ganciclovir; inducible Caspase 9, which renders cells susceptible to a small molecular homodimerizer and CD20 and RQR8, which renders cells susceptible to Rituximab.

This technology adds a certain amount of safety to CAR T-cell therapy, however there are limitations. Firstly, it is a binary approach wherein all the CAR T-cells are destroyed upon addition of the suicide entity. In addition, medicinal therapeutics often have a therapeutic window. With a suicide gene the potency of the product cannot be tuned such that efficacy with tolerable toxicity can be achieved. Secondly, it is not clear whether a suicide gene would help with some of the immune-toxicities described above: for instance by the time a macrophage activation syndrome had been triggered, it may well no longer need the CAR T-cells to perpetuate and the suicide gene would no longer be helpful. The more acute cytokine release syndromes probably occur too quickly for the suicide gene to work. Finally, suicide genes are not "fail-safe", i.e. the default status is for the CAR T-cells to be active.

There is thus a need for alternative methods for controlling CAR T-cells that are not associated with the disadvantages and problems mentioned above.

SUMMARY OF ASPECTS OF THE INVENTION

Figure 1:
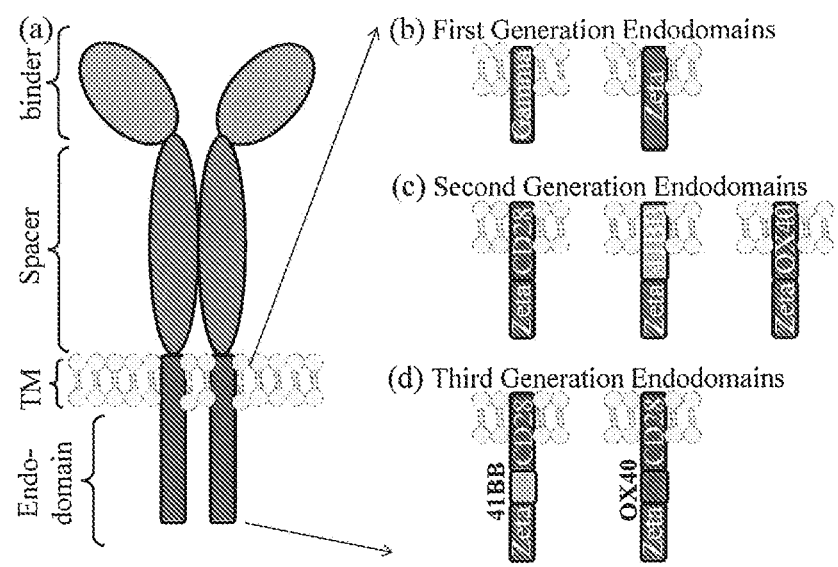
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.

The present inventors have found that it is possible to separate the antigen-recognition and signalling components of a CAR to produce an inducible system, where signalling only takes place in the presence of an agent such as a small molecule which can induce dimerization (henceforth referred to as chemical inducer of dimerization or CID).

The CID binds two protein domains simultaneously. By incorporating a CID binding domain into each of two non-functional halves of a CAR, the presence of CID will re-unite the halves constituting a functional whole.

Functional signalling by the CAR is hence dependent on the presence of the CID. This provides a mechanism for controlling the CAR T-cell after it has been administered to a patient: The CAR T-cell can be remotely switched on by administering the CID to the patient, and in case of toxicity switched off by not administering further CID. If activity of the CAR is proportional to local concentration of the agent (for instance when CID concentration is not saturating) activity of the CAR T-cells can be "tuned" by altering CID dose administered to the patient.

In a first aspect, the present relates to a chimeric antigen receptor (CAR) signalling system comprising of two separate protein components:
  (i) A membrane spanning receptor component comprising an extracellular antigen-binding domain, a transmembrane domain and a first intracellular CID binding domain (referred henceforth as CBD1); and
  (ii) An intracellular signalling component comprising at a minimum a signalling domain and a second CID binding domain (henceforth referred to as CBD2);
wherein CBD1 and CBD2 are capable of simultaneously and specifically binding to the CID.

Thus, in a first aspect, the present invention provides a chimeric antigen receptor (CAR) signalling system comprising;

(i) a receptor component comprising an extracellular antigen-binding domain, a transmembrane domain and a intracellular first chemical inducer of dimerization (CID) binding domain (CBD1); and
(ii) an intracellular signalling component comprising a signalling domain and a second CID binding domain (CBD2); wherein CBD1 and CBD2 are capable of simultaneously binding to a CID;
wherein, in the absence of CID, binding of the antigen-binding domain to antigen does not result in signalling through the signalling domain; whilst, in the presence of CID, the receptor component and the signalling component heterodimerize and binding of the antigen-binding domain to antigen results in signalling through the signalling domain.

CBD1 and CBD2 of the CAR signalling system according to the first aspect may comprise different CID binding domains and the CID may comprise two different binding moieties.

CDB1 may comprise the rapamycin binding domain of FK-binding protein 12 (FKBP12), CDB2 may comprise the FKBP12-Rapamycin Binding (FRB) domain of mTOR, or visa-versa. In this case, the CID may comprise rapamycin or a derivative thereof which is capable of causing the receptor component and the signalling component to heterodimerize.

CBD1 may comprise the FK506 (Tacrolimus) binding domain of FK-binding protein 12 (FKBP12), CBD2 may comprise the cyclosporin binding domain of cylcophilin A (or visa versa). In this case, the CID may comprise an FK506/cyclosporin fusion protein or a derivative thereof which is capable of causing the receptor component and the signalling component to heterodimerize.

CBD1 may comprise an oestrogen-binding domain (EBD), CBD2 may comprise a streptavidin binding domain, or visa-versa. In this case, the CID may comprise an estrone/biotin fusion protein or a derivative thereof which is capable of causing the receptor component and the signalling component to heterodimerize.

CBD1 may comprise a glucocorticoid-binding domain (GBD), CBD2 may comprise a dihydrofolate reductase (DHFR) binding domain, or visa-versa. In this case, the CID may comprise a dexamethasone/methotrexate fusion molecule or a derivative thereof which is capable of causing the receptor component and the signalling component to heterodimerize.

CBD1 may comprise an $O^6$-alkylguanine-DNA alkyltransferase (AGT) binding domain, CBD2 may comprise a dihydrofolate reductase (DHFR) binding domain, or vice-versa. In this case, the CID may comprise an $O^6$-benzylguanine derivative/methotrexate fusion molecule or a derivative thereof which is capable of causing the receptor component and the signalling component to heterodimerize.

CBD1 may comprise a retinoic acid receptor domain, CBD2 may comprise an ecodysone receptor domain, or vice-versa. In this case, the CID may comprise RSL1 or a derivative thereof which is capable of causing the receptor component and the signalling component to heterodimerize.

CBD1 and CBD2 of the CAR signalling system according to the first aspect of the invention may comprise the same CID binding domain and the CID may comprise two identical binding moieties.

CBD1 and CBD2 of the CAR signalling system according to the first aspect of the invention may comprise FK506 binding protein (FKBP12) binding domains comprising a F36V mutation and the CID may comprise AP1903 or a derivative thereof which is capable of causing the receptor component and the signalling component to heterodimerize.

In a second embodiment, the CAR may comprise a receptor component which spans the membrane multiple times with each intracellular portion constituting a CBD1. Hence a single receptor component may recruit multiple signalling components hence amplifying signal.

In a third embodiment, the CAR may comprise a set of separate receptor components each with an intracellular CBD1 such that in the presence of CID, signalling components connect to each receptor protein component so that the CAR can signal in response to a multiplicity of cognate antigens.

The CID binding domains may be altered such that affinity to the CID differs. For instance altering amino acids at Positions 2095, 2098, and 2101 of FRB can alter binding to Rapamycin: KTW has high, KHF intermediate and PLW is low (Bayle et al, Chemistry & Biology 13, 99-107, January 2006)

Hence, in the fourth embodiment, the CAR may comprise multiple receptor components such that each one has a CBD1 domain of different affinity to the CID. In this way, in the presence of CID, signalling protein components connect to each receptor protein component differentially and hence the CAR signal strengths differentially in response to each cognate antigen.

In the above embodiment, the signalling domain of the signalling protein component may comprise of a single endodomain selected from activating or co-stimulating T-cell signalling receptor such as CD3 zeta, CD28, 41 BB or OX40.

In the above embodiments, the signalling domain of the signalling protein component may comprise of a multiplicity of endodomains selected from activating and co-stimulating T-cell signalling receptor such as CD3 Zeta, CD28, 41 BB and OX40

If an inhibitory CAR is desired, in the above aspects, the signalling domain of the signalling protein may comprise the endodomain of an inhibitory T-cell signalling receptor or a phosphatase.

In a fifth embodiment, the signalling component according to the above embodiments of the invention may comprise a plurality of signalling components, each comprising a different signalling domain and a similar CBD2, wherein the CID agent binding domains each recognise the same CID, but the signalling domains comprise different endodomains. In this way, the CAR can transmit multiple signals but the signalling components being in trans rather than cis are sterically unencumbered from each other's signalling transmission molecules unlike a single signalling component containing a multiplicity of endodomains.

In a sixth embodiment, the CBD2 of the multiple signalling domains in the aspect described above may bind to the CID molecule with different affinities such that the relative contribution of each signalling component can be tuned. Hence the CAR can transmit a more complex signal rather than the fixed stoichiometry of a single signalling component containing a multiplicity of endodomains.

In a seventh embodiment, the CAR systems described above may comprise signalling domains which contains a CBD1, single or multiple endodomains as well as CBD2. Hence, in the presence of CID, concatenation of multiple signalling domains together to amplify signals.

In a second aspect, the present invention provides a receptor component suitable for use in the CAR signalling system of the first aspect of the invention which comprises an antigen-binding domain, a transmembrane domain and a CID binding domain.

In a third aspect, the present invention provides a signalling component suitable for use in the CAR signalling system according to the first aspect of the invention which comprises a signalling domain and a CID binding domain.

In a fourth aspect, the present invention provides a nucleic acid encoding the receptor component according to the second aspect of the invention.

In a fifth aspect, the present invention provides a nucleic acid encoding the signalling component according to the third aspect of the invention.

In a sixth aspect, the present invention provides a nucleic acid sequence encoding the receptor component according to the second aspect of the invention and the signalling component according to the third aspect of the invention, wherein the expressed molecule is a self-cleaving peptide which is cleaved between the receptor component and the signalling component.

In a seventh aspect, the present invention provides a vector comprising a nucleic acid sequence according to any of the fourth to sixth aspects of the invention.

In an eighth aspect, the present invention provides a retroviral vector or a lentiviral vector or a transposon comprising a vector according to the seventh aspect of the invention.

In a ninth aspect, the invention provides a T cell or NK cell which expresses a receptor component according to the second aspect of the invention and at least one signalling component according to the third aspect of the invention.

The T cell or NK cell according to the ninth aspect of the invention may comprise the nucleic acid according to any of the fourth to sixth aspects of the invention or the vector according to the seventh or eighth aspects of the invention.

In a tenth aspect, the present invention provides a pharmaceutical composition comprising a plurality of T cells or NK cells according to the ninth aspect of the invention.

In an eleventh aspect, the present invention provides a pharmaceutical composition according to the tenth 13$^{th}$ aspect of the invention for use in treating and/or preventing a disease.

In a twelfth aspect, the invention provides a method for treating and/or preventing a disease, which comprises the step of administering a pharmaceutical composition according to the tenth aspect of the invention to a subject.

The method according to the twelfth aspect of the invention may comprise the following steps:
(i) isolation of a T or NK cell-containing sample from a subject;
(ii) transduction or transfection of the T or NK cells with a nucleic acid sequence according to any the fourth to sixth aspects or a vector according to the seventh or eighth aspects; and
(iii) administering the cells from (ii) to the subject.

The method according to the twelfth aspect of the invention may further comprise the step of administering a CID suitable for use in the CAR signalling system according to the first aspect to the subject.

In a thirteenth, the present invention provides a method for treating and/or preventing a disease in a subject which subject comprises T cells according to the ninth aspect of the invention, which method comprises the step of administering a CIFD suitable for use in the CAR signalling system according to the first aspect of the invention to the subject.

The method according to the twelfth or thirteenth aspect of the invention may involve monitoring the progression of disease and/or monitoring toxic activity in the subject and adjusting the dose of the CID to provide acceptable levels of disease progression and/or toxic activity.

The disease to be prevented and/or treated according to the eleventh, twelfth or thirteenth aspect of the invention may be cancer.

In a fourteenth aspect, the present invention provides the use of a pharmaceutical composition according to the tenth aspect of the invention in the manufacture of a medicament for the treatment and/or prevention of a disease.

In a fifteenth aspect, the present invention provides a kit which comprises a nucleic acid according to any of the fourth to sixth aspects of the invention or a vector according to the seventh or eighth aspects of the invention.

The kit may also comprise a CID suitable for use in the CAR signalling system according to the first aspect of the invention.

In a sixteenth aspect, the invention provides a kit which comprises a T cell or NK cell according to the ninth aspect of the invention and a CID suitable for use in the CAR signalling system according to the first aspect of the invention.

In a seventeenth aspect, the present invention provides a method for making a T cell or NK cell according to claim ninth aspect of the invention, which comprises the step of introducing: a nucleic acid sequence according to any of the fourth to sixth aspects of the invention or a vector according to the seventh or eighth aspects of the invention, into a T or NK cell.

The T or NK cell may be from a sample isolated from a subject.

In an eighteenth aspect, the invention provides a method for activating the CAR signalling system according to the first aspect of the invention in a subject which comprises a T-cell according to the ninth aspect of the invention, which method comprises the step of administering the CID to the subject.

In a nineteenth aspect the invention provides a method for reducing the activity of the CAR signalling system according to the first aspect of the invention, in a subject which comprises a T-cell or NK cell according to the ninth aspect of the invention, which method comprises reducing or stopping administration of the CID to the subject.

In a twentieth aspect the present invention provides a method for activating signalling in a CAR signalling system according to the first aspect of the invention in a T cell or NK cell according to the ninth aspect of the invention in culture, which comprises the step of introducing the CID agent to the T or NK cell culture.

In a twenty-first aspect the present invention provides a method for reducing or stopping signalling via a CAR signalling system according to the first aspect of the invention in a T or NK cell according to the ninth aspect of the invention in culture, which comprises the step of removing the CID from the T or NK cell culture.

In a twenty-second aspect, there is provided a method for inducing dimerization in vivo between a receptor component according to the second aspect of the invention and a signalling component according to the third aspect of the invention, which comprises the step of administering a chemical inducer of dimerization (CID) to a subject comprising a cell according to the ninth aspect of the invention.

The present invention therefore provides a means of tuning the CAR activity to the presence of an agent, such as a small molecule. This allows the potency of CAR cells to be controlled pharmacologically and tuned to an acceptable balance between achieving the desired therapeutic effect, while avoiding CAR-associated toxicities.

DETAILED DESCRIPTION

Chimeric Antigen Receptors (CARs)

Classical CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain may be necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Figure 3:
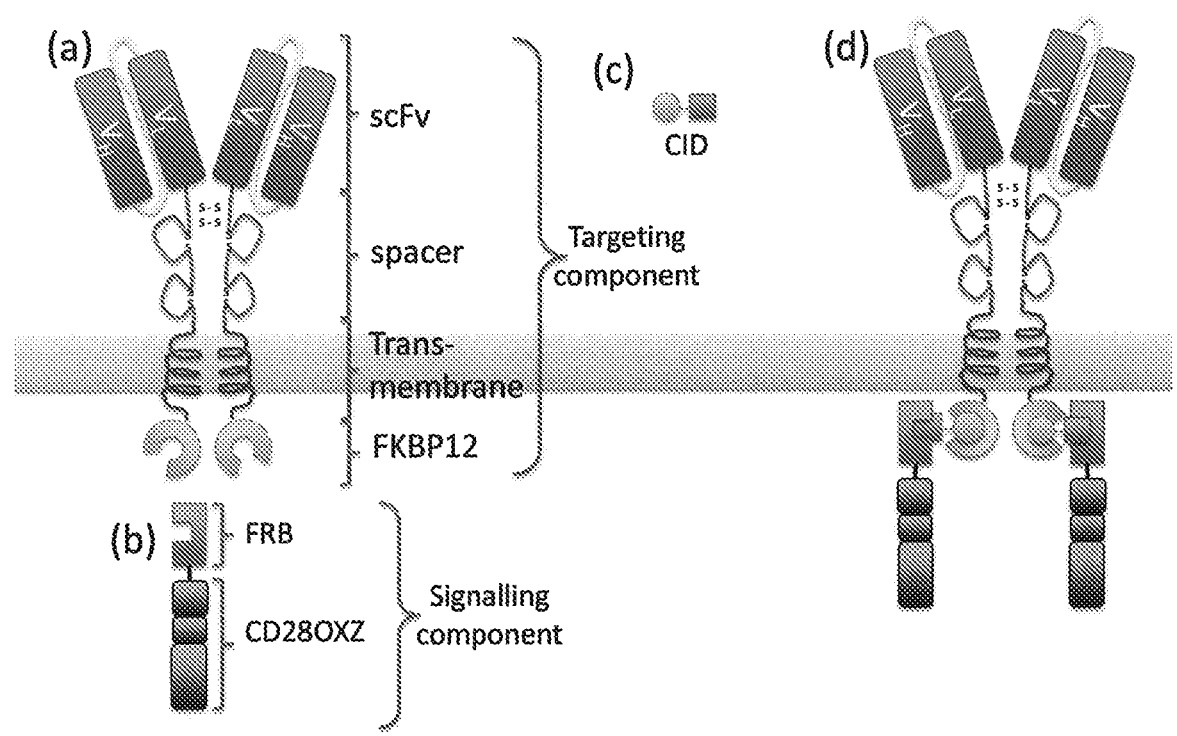
FIG. 3—Illustration of an example of an inducible CAR signalling system in its simplest incarnation. (a) Receptor component comprising of an extracellular scFv, a spacer, a trans-membrane domain and an intracellular FKBP12. (b) Signalling component: intracellular fusion between FRB fragment of mTOR and the endodomains of CD28, OX40 and CD3 Zeta. (c) A chemical inducer of dimerization (CID), in this case is Rapamycin or an analogue. (d) Receptor component. In the presence of CID, the receptor component and the signalling components dimerize allowing signalling in the presence of cognate antigen.
Figure 4:
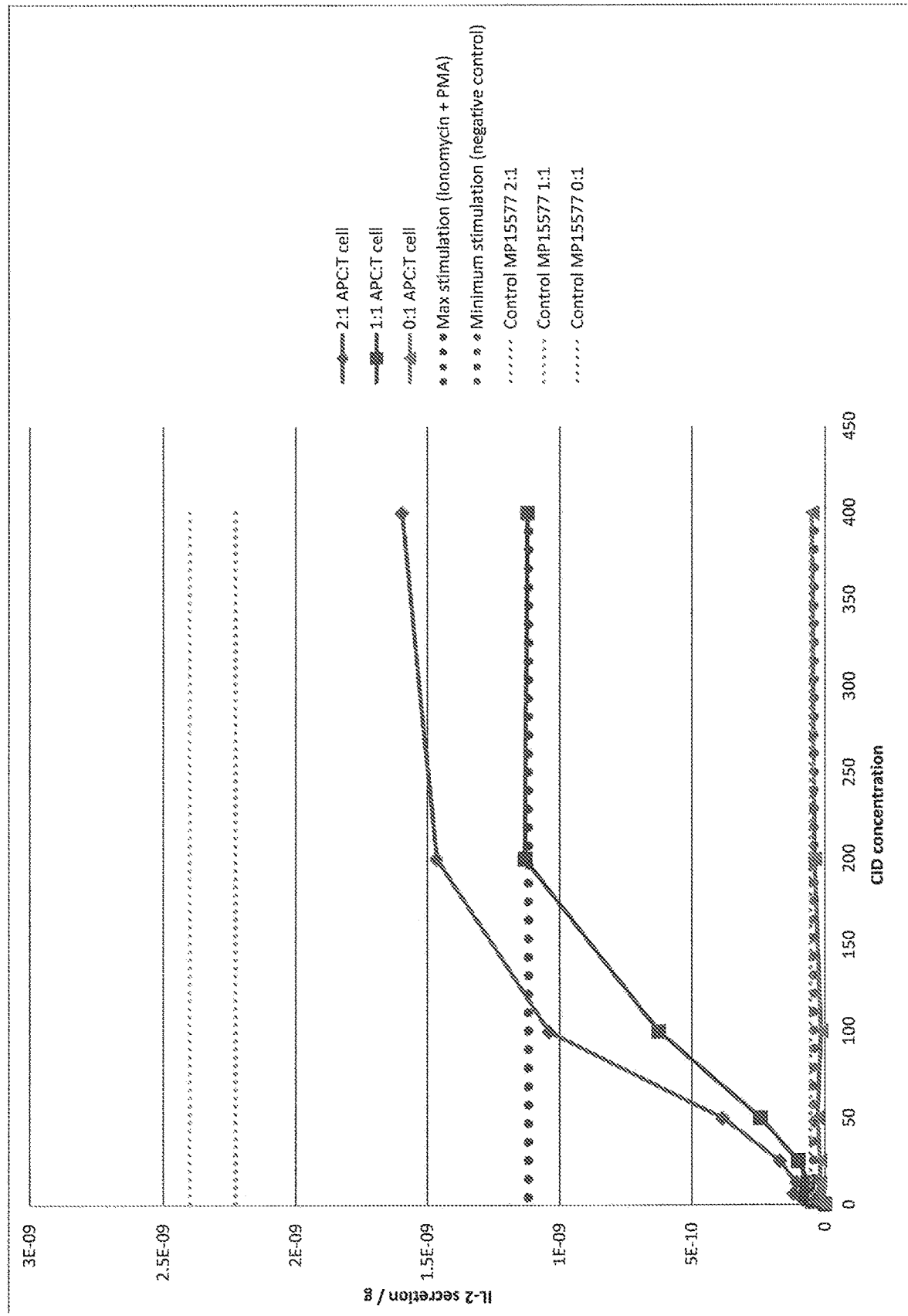
FIG. 4—Function of an inducible CAR system. T-cells were transduced with a CAR system as illustrated in FIG. 3 and with SEQ ID No. 19. This CAR recognizes CD19. CAR expressing T-cells were challenged with CD19+ targets at 1:1 and 2:1 effector to target ratios in the presence of increasing concentration of CID. T-cells respond to target cells only in the presence of CID. Stimulation with PMA/Ionomycin is also show. Response to CD19+ targets of T-cells expressing a standard CD19 CAR (MP15577) to different effector target ratios is also shown.

In a first aspect, the present invention relates to a CAR signalling system in which the antigen-recognizing/antigen binding domain and transmembrane domain are provided on a first molecule (termed herein 'receptor component'), which localizes to the cell membrane. The intracellular signalling domain is provided on a second, intracellular molecule (termed herein 'signaling component'). Certain small molecules have been described which bind simultaneously to two protein domains. Such small molecules can hence act to dimerize proteins (termed herein "chemical inducer of dimerization" or "CID"). Both the receptor component and signaling components comprise a CID binding domain (termed herein 'CID Binding Domain 1', or 'CBD1' and 'CID Binding Domain 2' or 'CBD2' respectively) which allows each receptor component and signalling component to bind simultaneously to the same CID molecule (FIG. 3).

When antigen binds to the antigen-binding domain of the receptor component in the absence of the CID, there is no signalling through the signaling component. When the CID is present, receptor binding of antigen to the antigen-binding domain of the receptor component results in signaling through the signalling component.

Specifically, in the absence of CID, the receptor component and signalling component are located in a stochastically dispersed manner and binding of antigen by the antigen-binding domain of the receptor component does not result in signalling through the signaling component. In the presence of the CID, both the receptor and signalling component of the CAR bind the CID via their CID binding domains, resulting in co-localization of the receptor component and signaling components (heterodimerization). This co-localisation allows signalling through the signalling domain of the signalling component when antigen is bound by the antigen-binding domain of the receptor component.

Herein 'co-localization' or 'heterodimerization' of the receptor and signalling components is analogous to ligation/recruitment of the signalling component to the receptor component via the CID agent.

Antigen binding by the receptor component in the absence of the CID may be termed as resulting in 'non-productive' signaling through the signaling component. Such signaling does not result in cell activation, for example T cell activation. Antigen binding by the receptor component in the presence of CID may be termed as resulting in 'productive' signaling through the signaling component. This signaling results in T-cell activation, triggering for example target cell killing and T cell activation.

Antigen binding by the receptor component in the presence of CID may result in signalling through the signalling component which is 2, 5, 10, 50, 100, 1,000 or 10,000-fold higher than the signalling which occurs when antigen is bound by the receptor domain in the absence of CID.

Signaling through the signaling component may be determined by a variety of methods known in the art. Such methods include assaying signal transduction, for example assaying levels of specific protein tyrosine kinases (PTKs), breakdown of phosphatidylinositol 4,5-biphosphate ($PIP_2$), activation of protein kinase C (PKC) and elevation of intracellular calcium ion concentration. Functional readouts, such as clonal expansion of T cells, upregulation of activation markers on the cell surface, differentiation into effector cells and induction of cytotoxicity or cytokine secretion may also be utilised. As an illustration, in the present examples the inventors determined levels of interleukin-2 (IL-2) produced by T-cells expressing a receptor component and signalling component of the CAR signalling system according to the present invention upon binding of antigen to the receptor component in the presence of varying concentrations of CID.

Chemical Inducer of Dimerization & Binding Domains

The CID and CID binding domains of the CAR signalling system of the first aspect of the invention may be any combination of molecules/peptides/domains which enables the selective co-localisation and dimerization of the receptor component and signalling component in the presence of the CID.

As such, the CID agent is a molecule which is able to simultaneously bind to the receptor component and the signalling component. The CID agent therefore comprises at least two binding moieties.

The CID may be any pharmaceutically acceptable molecule which can simultaneously be bound by at least two binding domains.

The CID is capable being delivered to the cytoplasm of a target cell and being available for intracellular binding.

Small molecule dimerization systems for facilitating the co-localization of peptides are known in the art (Corson et al.; 2008; ACS Chemical Biology; 3(11); 667).

The binding moieties of the CID may interact with identical binding domains present on the receptor component and the signalling component. That is, the CID may comprise two identical binding moieties such that it can simultaneously interact with a binding domain on the receptor component and an identical binding domain on the signalling component.

The CID and CID binding domains may be the FK506 binding protein (FKBP) ligand dimerization system described by Clackson et al. (PNAS; 1998; 95; 10437-10442). This dimerization system comprises two FKBP-like binding domains with a F36V mutation in the FKBP binding domain and a dimerization agent (AP1903) with complementary amino acid substitutions. Exposing cells engineered to express FKBP-like binding domain fusion proteins to AP103 results in the dimerization of the proteins comprising the FKBP-like binding domains but no interactions involving endogenous FKBP.

The dimerization system described by Farrar et al., which utilises bacterial DNA gyrase B (GyrB) binding domains and the antibiotic coumermycin as CID may also be used in the signalling system of the present invention (Methods Enzymol; 2000; 327; 421-419 and Nature; 1996; 383; 178-181).

The binding moieties of the CID may interact with different binding domains on the receptor component and the signalling component. That is, the CID may comprise two different binding moieties which can simultaneously interact with a binding domain on the receptor component and a different binding domain on the signalling component.

The CID and CID binding domains may comprise the dimerization system described by Belshaw et al. (Nature; 1996; 93; 4604-4607), which utilises a FK506 (Tacrolimus)/cyclosporin fusion molecule as the CID agent with FK-binding protein 12 (FKBP12) and cylcophilin A as the binding domains.

Figure 2:
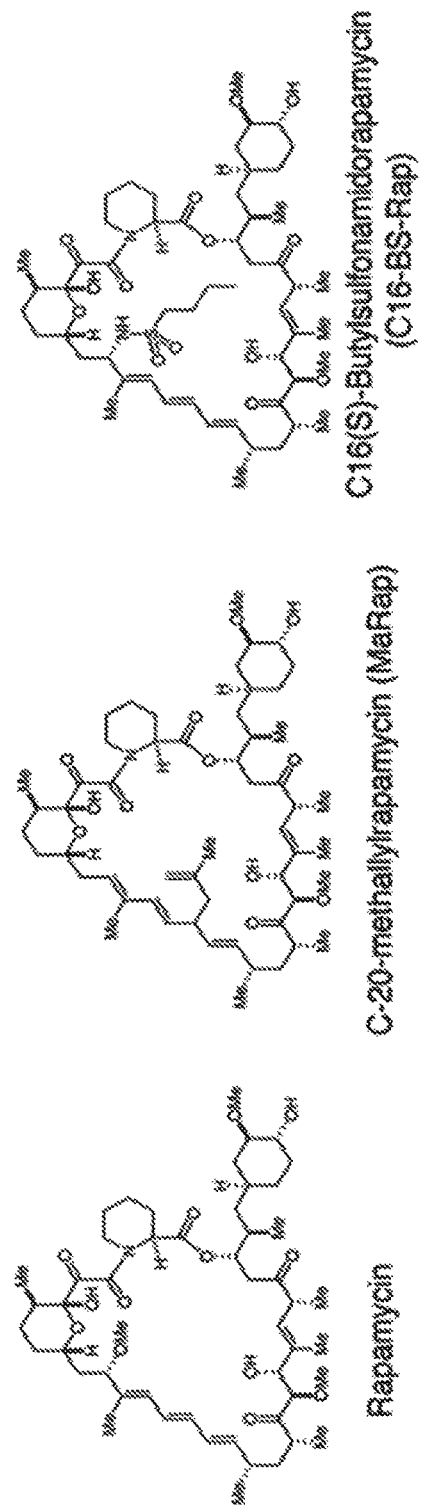
FIG. 2—Structures of Rapamycin analogues.

The CID/CID binding domain may also be the rapamycin and FKBP12/FKBP12-Rapamycin Binding (FRB) domain of mTOR system described by Rivera et al. (Nature Med; 1996; 2; 1028-1032) or the non-immunosuppressive rapamycin analogs (rapalogs) and FKBP12/FRB system described by Bayle et al. (Chem Bio; 2006; 13; 99-107). For example the CID may be C-20-methyllyrlrapamycin (MaRap) or C16(S)-Butylsulfonamidorapamycin (C16-BS-Rap), as described by Bayle et al. and illustrated in FIG. 2 in combination with the corresponding binding domains. The CID may be C16-(S)-3-methylindolerapamycin (C16-iRap) or C16-(S)-7-methylindolerapamycin (AP21976/C16-AiRap) as described by Bayle et al., in combination with the respective complementary binding domains for each.

Other dimerization systems suitable for use in the signalling system of the present invention include an estrone/biotin CID in combination with an oestrogen-binding domain (EBD) and a streptavidin binding domain (Muddana & Peterson; Org. Lett; 2004; 6; 1409-1412; Hussey et al.; J. Am. Chem. Soc.; 125; 3692-3693); a dexamethasone/methotrexate CID in combination with a glucocorticoid-binding domain (GBD) and a dihydrofolate reductase (DHFR) binding domain (Lin et al.; J. Am. Chem. Soc.; 2000; 122; 4247-4248); a similar system in which the methotrexate portion of the CID is replaced with the bacterial specific DHFR inhibitor trimethoprim (Gallagher et al.; Anal. Biochem.; 2007; 363; 160-162) and an O$^6$-benzylguanine derivative/methotrexate CID in combination with an O6-alkylguanine-DNA alkyltransferase (AGT) binding domain and a DHFR binding domain (Gendreizig et al.; J. Am. Chem. Soc.; 125; 14970-14971).

Figure 9:
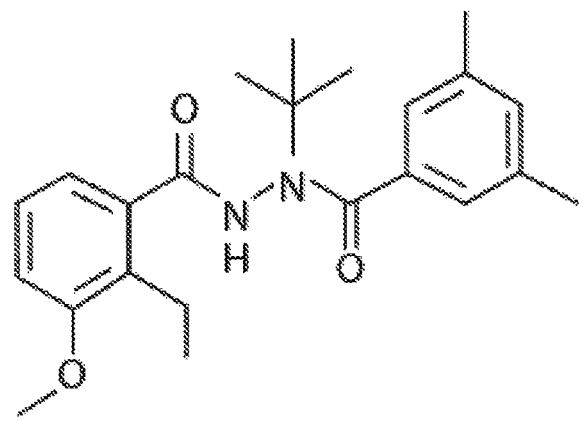
FIG. 9—Chemical structure of RSL1, the synthetic diacylhydrazine (N-(2-ethyl-3-methoxybenzoyl)-N'-(3,5-dimethylbenzoyl)-N'-tert-butylhydrazine. RSL1 is one of a family of compounds that have been found to act as non-steroidal ecdysone agonists and can function as gene inducers.

RSL1 is a synthetic non-steroidal analogue of 20-hydroxyecdysone (see FIG. 9). It is a member of a class of insecticides known as diacylhydrazines and can function to act as a non-steroidal ecdysone agonist. These molecules induce premature moulting and larvae death but are well tolerated in vertebrates. RSL1 has been used in artificial transcription switches in which a two-protein transcription switch is used consisting of a fusion between the ecdysone receptor (EcR) and GAL4, and the retinoid X receptor (RXR) and VP16. In such systems, EcR is modified to interact specifically with RSL13, and RXR is chimeric comprising of helices 1-8 replaced with helices 1-8 of human RXRβ, and helices 9-12 from *Locusta migratoria* RXR. The signalling system of the present invention may use EcR and RXR domains for heterdimerisation in the presence of RSL1 or a derivative thereof.

For example the CID binding domains may be or comprise the sequences shown as SEQ ID NO: 1 to SEQ ID NO: 5, SEQ ID No. 25 or 26.

```
FKBP12 domain
                                        SEQ ID No 1
MGVQVETISPGDGRTFPKRGQTCWHYTGMLEDGKKFDSSRDRNKPFKFML

GKQEVIRGWEEGVAQMSVGQRAKLTISPDYAYGATGHPGIIPPHATLVFD

VELLKLE wild-type FRB segment of mTOR
                                        SEQ ID No 2
MASRILWHEMWHEGLEEASRLYFGERNVKGMFEVLEPLHAMMERGPQTLK

ETSFNQAYGRDLMEAQEWCRKYMKSGNVKDLTQAWDLYYHVFRRISKLES

FRB with T to L substitution at 2098 which allows
binding to AP21967
                                        SEQ ID No 3
MASRILWHEMWHEGLEEASRLYFGERNVKGMFEVLEPLHAMMERGPQTLK

ETSFNQAYGRDLMEAQEWCRKYMKSGNVKDLLQAWDLYYHVFRRISKLES

FRB segment of mTOR with T to H substitution at
2098 and to W at F at residue 2101 of the full
mTOR which binds Rapamycin with reduced affinity
to wild type
                                        SEQ ID No 4
MASRILWHEMWHEGLEEASRLYFGERNVKGMFEVLEPLHAMMERGPQTLK

ETSFNQAYGRDLMEAQEWCRKYMKSGNVKDLHQAFDLYYHVFRRISKLES

FRB segment of mTOR with K to P substitution at
residue 2095 of the full mTOR which binds
Rapamycin with reduced affinity
                                        SEQ ID No 5
MASRILWHEMWHEGLEEASRLYFGERNVKGMFEVLEPLHAMMERGPQTLK

ETSFNQAYGRDLMEAQEWCRKYMKSGNVPDLTQAWDLYYHVFRRISKLES

EcR
                                       SEQ ID No. 25
MPVDRILEAELAVEQKSDQGVEGPGGTGGSGSSPNDPVTNICQAADKQLF

TLVEWAKRIPHFSSLPLDDQVILLRAGWNELLIASFSHRSIDVRDGILLA

TGLHVHRNSAHSAGVGAIFDRVLTELVSKMRDMRMDKTELGCLRAIILFN

PEVRGLKSAQEVELLREKVYAALEEYTRTTHPDEPGRFAKLLLRLPSLRS

IGLKCLEHLFFFRLIGDVPIDTFLMEMLESPSDS

RXR
```

-continued

SEQ ID No. 26
RPECVVPETQCAMKRKEKKAQKEKDKLPVSITTVDDHMPPIMQCEPPPPE

AARIHEVVPRFLSDKLLETNRQKNIPQLTANQQFLIARLIWYQDGYEQPS

DEDLKRITQTVVQQADDENEESDTPFRQITEMTILTVQLIVEFAKGLPGF

AKISQPDQITLLKACSSEVMMLRVARRYDAASDSILFANNQAYTRDNYRK

AGMAEVIEDLLHFCRCMYSMALDNIHYALLTAVVIFSDRPGLEQPQLVEE

IQRYYLNTLRIYILNQLSGSARSSVIYGKILSILSELRTLGMQNSNMCIS

LKLKNRKLPPFLEEIWDVADMSHTQPPPILESPTNL

Variant sequences may have at least 80%, 85%, 90%, 95%, 98% or 99% sequence identity to SEQ ID No. 1 to 5, 25 or 26 provided that the sequences provide an effective dimerization system. That is, provided that the sequences facilitate sufficient co-localisation of the antigen-binding and intracellular signalling components, in the presence of the CID, for successful signaling to occur upon binding of the antigen-binding domain to antigen.

The signalling system according to the present invention is not limited by the arrangement of a specific dimerization system. The receptor component may comprise either binding domain of a given dimerization system so long as the signalling component comprises the corresponding, complementary binding domain which enables the receptor component and signalling component to co-localize in the presence of the CID.

The present invention also relates to a method for activating the CAR signalling system of the first aspect which comprises the step of administering the CID. As described above, administration of the CID results in co-localization of the receptor component and signalling component, such that signalling through the signalling domain occurs upon binding of the antigen-binding domain to antigen.

The CID and CID binding domains may facilitate signalling through the CAR signalling system which is proportional to the concentration of CID present.

The present invention further provides a method for reducing the activity of the CAR system of the first aspect which comprises reducing or stopping the administration of the CID. Reducing the level of the CID results in fewer receptor: signalling component dimers and thus the total level of signalling through the CAR signaling system is decreased in the presence of the antigen. Stopping the administration of the CID results in the absence of receptor: signalling component dimers and termination of signalling despite the presence of antigen binding to the antigen-binding domain.

Another possibility of this system is to "tune" the signal strength the receptor transmits. If the affinity between one or both of the CID binding domains is lessened, less CAR systems will be active and hence signal propagation upon antigen binding is lessened. This may avoid toxicity.

Receptor Component

The present invention provides a receptor component comprising an antigen-binding domain, an optional spacer domain, a transmembrane domain and a CID biding domain (CBD1). When expressed in a cell, the receptor component localises to the cell membrane. Here, the antigen-binding domain of the molecule is orientated on the extracellular side of the membrane and the CBD is localised to the intracellular side of the membrane.

The receptor component therefore provides the antigen-binding function of the CAR signalling system of the present invention.

Antigen Binding Domain

The antigen-binding domain is the portion of a classical CAR which recognizes antigen. In the signalling system of the present invention the antigen-binding is located within the receptor component.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
| --- | --- |
| Diffuse Large B-cell Lymphoma | CD19, CD20 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Transmembrane Domain

The transmembrane domain is the sequence of a classical CAR that spans the membrane. In the signalling system of the present invention the transmembrane domain is located in the receptor component. It may comprise a hydrophobic alpha helix. The transmembrane domain may be derived from CD28, which gives good receptor stability. The transmembrane domain may be from CD148, as shown in SEQ ID No. 23.

Signal Peptide

The receptor component of the CAR signalling system of the present invention may comprise a signal peptide so that when the receptor component is expressed in a cell, such as a T-cell, the nascent protein is directed to the endoplasmic reticulum and subsequently to the cell surface, where it is displayed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID No, 6, 7 or 8 or a variant thereof having 5, 4, 3, 2 or 1 amino acid mutations (insertions, substitutions or additions) provided that the signal peptide still functions to cause cell surface expression of the CAR.

```
SEQ ID No. 6:
MGTSLLCWMALCLLGADHADG
```

The signal peptide of SEQ ID No. 6 is compact and highly efficient. It is predicted to give about 95% cleavage after the terminal glycine, giving efficient removal by signal peptidase.

```
SEQ ID No. 7:
MSLPVTALLLPLALLLHAARP
```

The signal peptide of SEQ ID No. 7 is derived from IgG1.

```
SEQ ID No. 8:
MAVPTQVLGLLLLWLTDARC
```

The signal peptide of SEQ ID No. 8 is derived from CD8.

Spacer Domain

The CAR signalling system described herein may comprise a spacer sequence to connect the antigen-binding domain with the transmembrane domain in the receptor component. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
SEQ ID No. 9 (hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKKD

SEQ ID No. 10 (human CD8 stalk):
TTTPAPRPPTPAPTIASQPLSLRPEACRPAAGGAVHTRGLDFACDI

SEQ ID No. 11 (human IgG1 hinge):
AEPKSPDKTHTCPPCPKDPK

SEQ ID No. 12 (CD2 ectodomain)
KEITNALETINGALGQDINLDIPSFQMSDDIDDIKWEKTSDKKKIAQFRK

EKETFKEKDTYKLFKNGTLKIKHLKTDDQDIYKVSIYDTKGKNVLEKIFD

LKIQERVSKPKISWTCINTTLTCEVMNGTDPELNLYQDGKHLKLSQRVIT

HKWITSLSAKFKCTAGNKVSKESSVEPVSCPEKGLD

SEQ ID no. 13 (CD34 ectodomain)
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT
```

Receptor Component Comprising Multiple Transmembrane Domains

Figure 6:
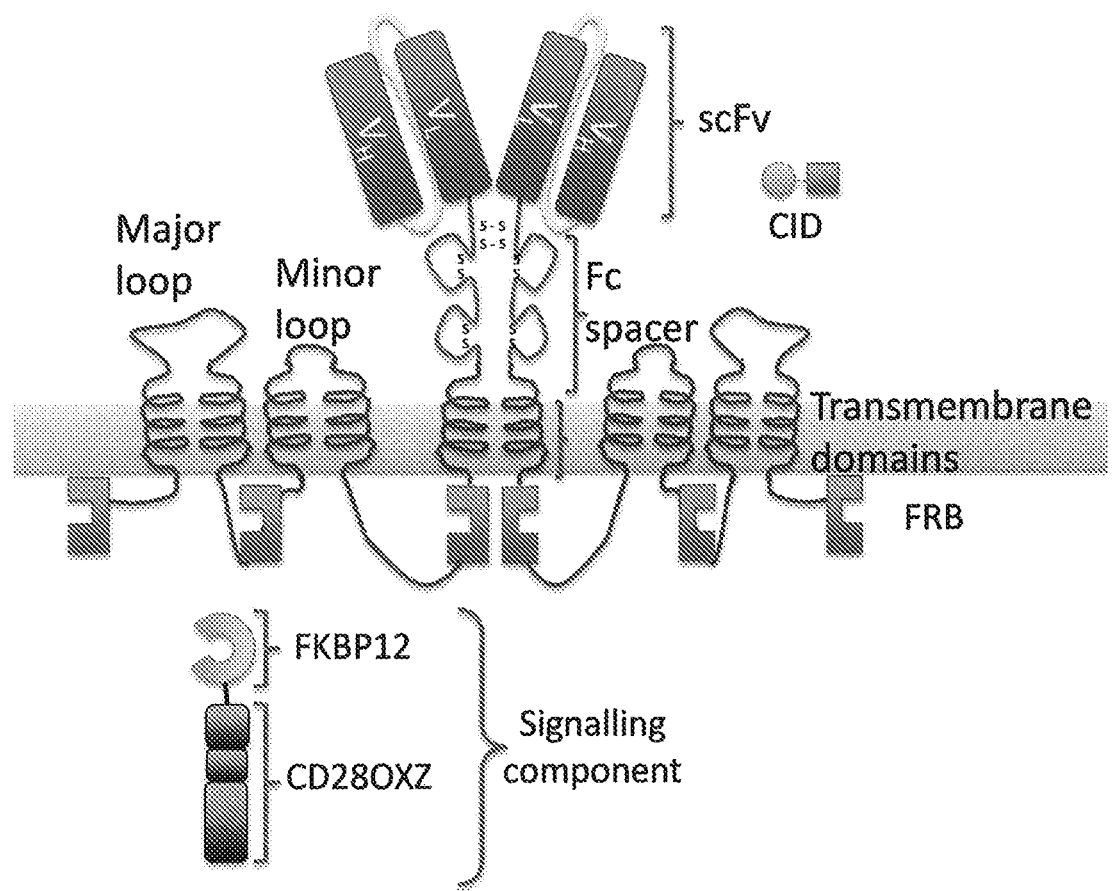
FIG. 6—Illustration of an example of a multiple transmembrane receptor domain receptor component for use in an inducible CAR signalling system. The receptor component is a chimera of a type I CAR linked to the multi-span protein. A scFv is connected to an Fc spacer domain and a TM domain. This in turn is connected to the CD20 molecule with truncated amino and carboxy termini. Each intracellular entry is attached to an FRB domain. The signalling component comprises of FKBP12 and a fusion of CD28, OX40 and CD3 Zeta endodomains. Addition of the CID allows the stochastic ligation of multiple signalling domains to the multiple endodomains which recognize a single antigen receptor component, resulting in amplified signalling in response to antigen.

The receptor component may comprise an appropriate number of transmembrane domains such that each CID binding domain is orientated on the intracellular side of the cell membrane (FIG. 6). For example the receptor component may comprise 3, 5, 7, 9, 11, or more transmembrane domains. In this way, a single receptor component may recruit multiple signalling components amplifying signalling in response to antigen. The signalling system encoded by SEQ ID No. 22 is a multi-spanning receptor with 3 FRB domains.

Multiple Receptor Components

Figure 5:
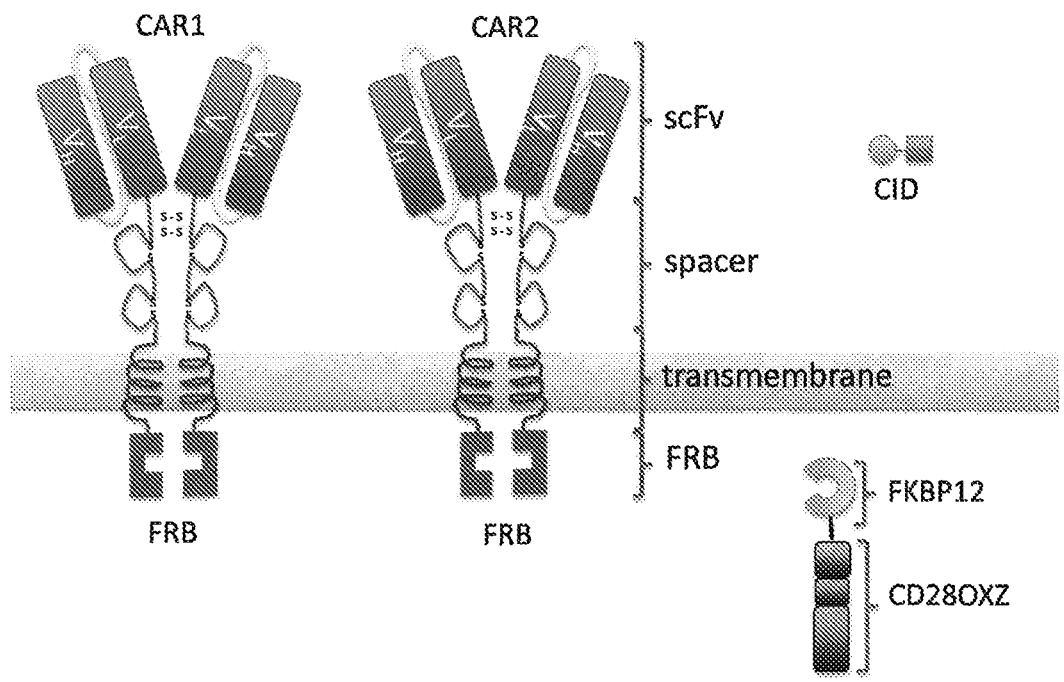
FIG. 5—Illustration of an inducible CAR system with two receptor components. (a) Two receptor components are co-expressed along with a single signalling component. The two receptor components each have a different single chain which recognizes a different target. The receptor components have endodomains comprising of the FRB fragment of mTOR. A single signalling component comprises of FKBP12 and a fusion of CD28, OX40 and CD3 Zeta endodomains. In (a), the FRB sequences are identical and this CAR will signal equally in response to either target. In (b), the FRB sequences differ such that each has a different affinity for the CID. With this implementation, the CAR will signal with different strength in response to each cognate antigen in the presence of CID.
Figure 5:
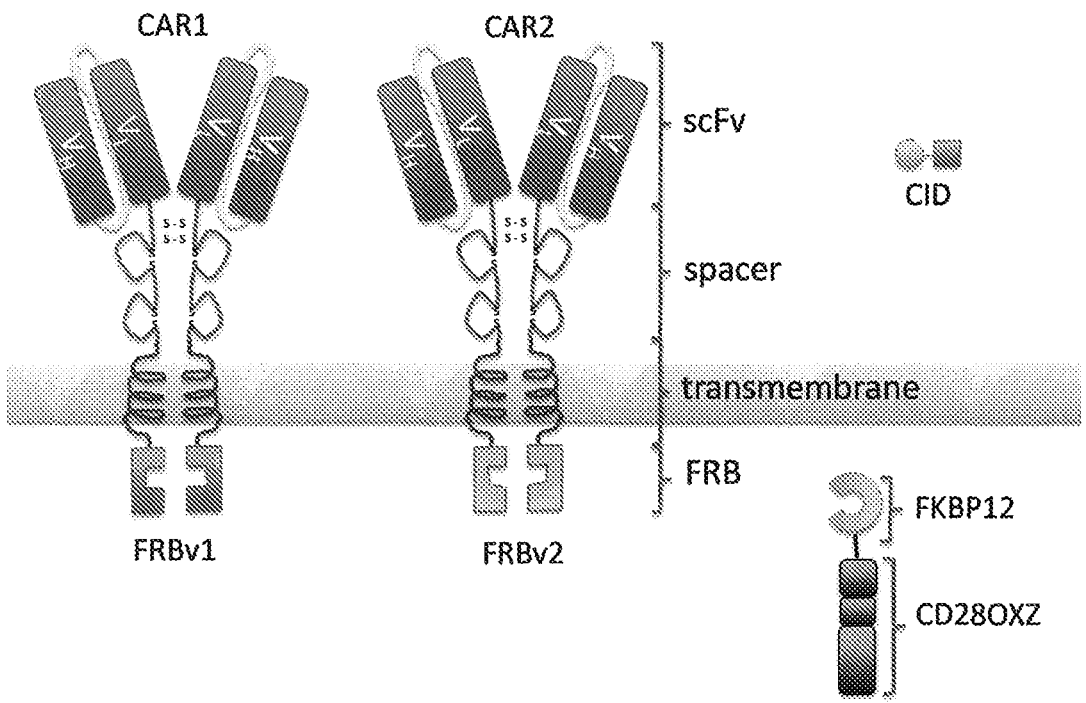

In another embodiment of the invention, the CAR signalling system may comprise of two or more receptor components each recognizing different antigens but comprising of the same intracellular CID binding domain. Such a CAR system would be capable of recognizing multiple antigens (FIG. 5a). This might be useful for instance in avoiding tumour escape. In a further related aspect of the invention, the CBD1 of the receptor components differ in residues which dictate their affinity to the CID. In this way, a CAR system can be tuned such that signalling in response to one antigen is greater or lesser than response to another (FIG. 5b). This might be useful for instance when targeting two tumour antigens simultaneously but one is expressed at a higher density than the other. Response to this antigen could be tuned down to avoid toxicity caused by over-stimulation.

Methods suitable for altering the amino acid residues of the CID binding domain such that its binding affinity for CID is altered are known in the art and include substitution, addition and removal of amino acids using both targeted and random mutagenesis. For example, in the case of CID binding to FRB, a set of mutations have been published with a range of affinity (Bayle et al, Chemistry & Biology 13, 99-107, January 2006). Methods for determining the affinity of a CID for the CID binding domain are also well known in the art and include bioinformatics prediction of protein-protein interactions, affinity electrophoresis, surface plasma resonance, bio-layer interferometry, dual polarisation interferometry, static light scattering and dynamic light scattering.

The signalling system encoded by SEQ ID No. 20 comprises two receptor components and one signalling component.

Signalling Component

The present invention also provides a signalling component comprising a signalling domain and a CID binding domain (CBD2). The signalling component is a soluble molecule and thus localises to the cytoplasm when it is expressed in a cell, for example a T cell.

No signalling occurs through the signalling domain of the signalling component unless it is co-localised with the receptor component provided by the present invention. Such co-localisation occurs only in the presence of the CID, as described above.

Intracellular Signalling Domain

The intracellular signalling domain is the signal-transmission portion of a classical CAR. In the signalling system of the present invention the intracellular signalling domain (signalling domain) is located in the signalling component. In the presence of the CID, the membrane-bound, receptor component and the intracellular signalling component are brought into proximity. After antigen recognition, receptors cluster, native CD45 and CD148 are excluded from the synapse and a signal is transmitted to the cell.

As such the signalling domain of the signalling component is analogous to the endodomain of a classical CAR molecule.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

The signalling component described herein comprises a signalling domain, it may comprise the CD3-Zeta endodomain alone, the CD3-Zeta endodomain with that of either CD28 or OX40 or the CD28 endodomain and OX40 and CD3-Zeta endodomain (FIG. 3A).

The signalling component of a CAR signalling system according to the present invention may comprise the sequence shown as SEQ ID No. 14, 15 or 16 or a variant thereof.

```
CD3 Z endodomain
                                 SEQ ID No. 14
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD28 and CD3 Zeta endodomains
                                 SEQ ID No. 15
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

CD28, OX40 and CD3 Zeta endodomains.
                                 SEQ ID No. 16
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR
```

A variant sequence may have at least 80%, 85%, 90%, 95%, 98% or 99% sequence identity to SEQ ID No. 14, 15 or 16, provided that the sequence provides an effective intracellular signalling domain.

Multiple Signalling Components

Figure 7:
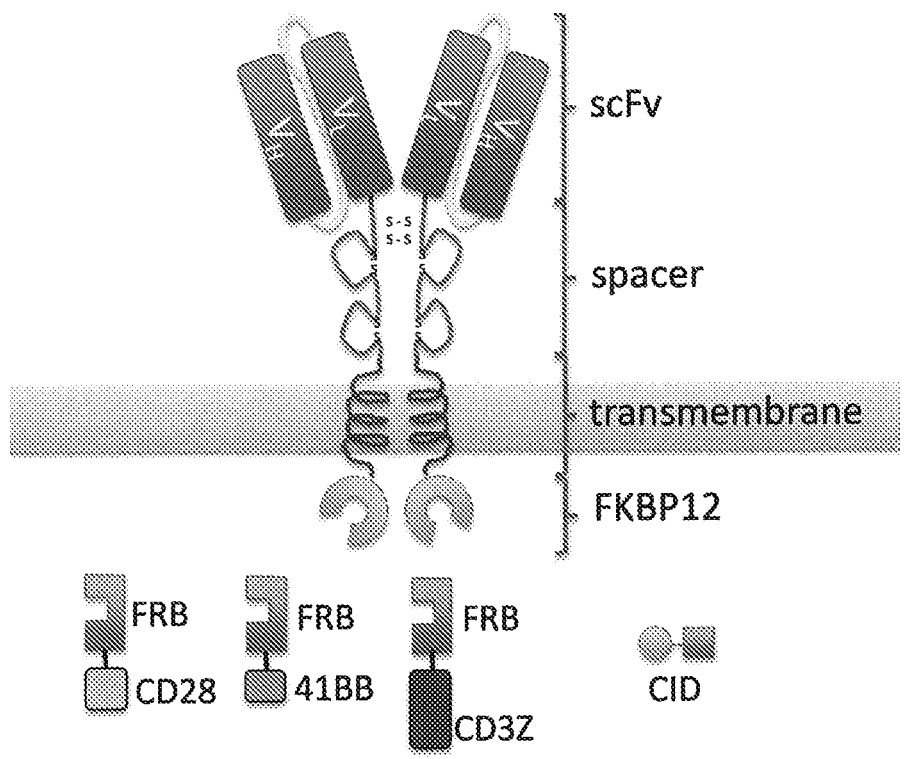
FIG. 7—Illustration of an inducible CAR system with multiple signalling component inducible CAR. This CAR system has a single receptor component comprising of a scFv, an Fc spacer, a TM domain and a FKBP12 endodomain. The three different signalling domains comprise of a fusion between the FRB fragment of mTOR and the CD28 endodomain, a fusion between the FRB fragment of mTOR and the 41BB endodomain and a fusion between the FRB fragment of mTOR and the CD3 Zeta endodomain. In (a), the FRB domains are identical so that each signalling component is recruited equally to the receptor component and the CAR transmits an equal CD28, 41BB and CD3 Zeta signal in the presence of CID and upon recognition of the cognate antigen. In (b), the FRB domains are different so that each signalling component can be recruited differently to the receptor component so that the CAR transmits more or less of each of CD28, 41BB and CD3 Zeta signals depending on the optimum needed for the application.
Figure 7:
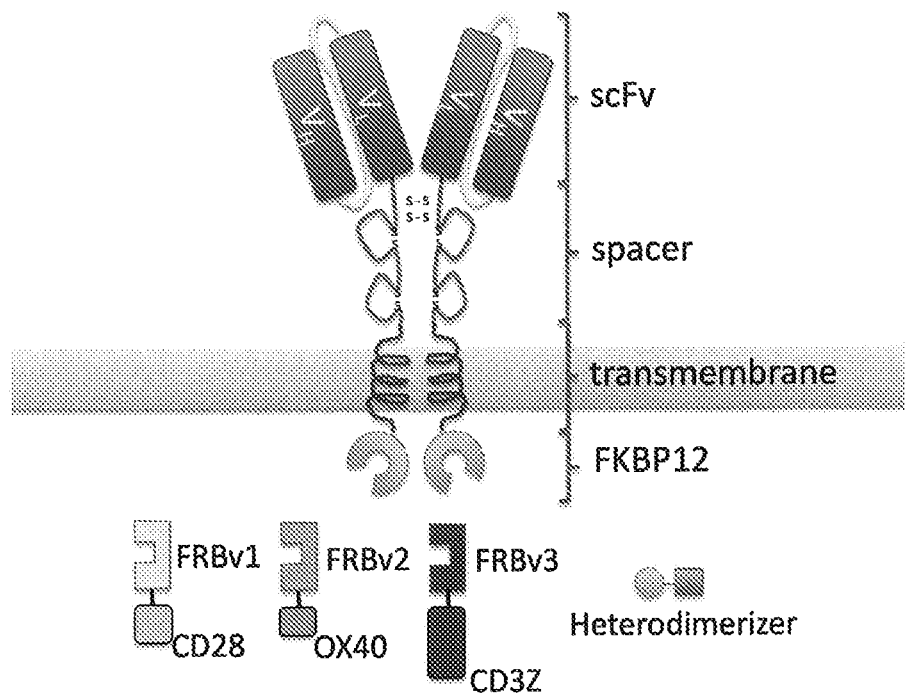

The signalling system according to the first aspect of the present invention may comprise a plurality of signalling components, each comprising a signalling domain and a CIDB2, wherein each signalling domain is bound by the same CID but the signalling domains comprise different endodomains (FIG. 7a). In this way, multiple different endodomains can be activated simultaneously. This is advantageous over a compound signalling domain since each signalling domain remains unencumbered from other signalling domains.

If each signalling component comprises of a CBD2 domains which differ in residues which alter their affinity to CID, the CID enables signalling components comprising different signalling domains to ligate to the CID with differing kinetics (FIG. 7b). This allows greater control over the signalling in response to antigen-binding by the receptor component as different signalling components are recruited to the receptor component in varying kinetics/dynamics. This is advantageous since rather than a fixed equal ratio of signal transmitted by a compound endodomain, an optimal T-cell activation signal may require different proportions of different immunological signals.

The signalling system encoded by SEQ ID No. 21 has one receptor components and three signalling components.

Signalling Components with an Additional CID Binding Domain

Figure 8:
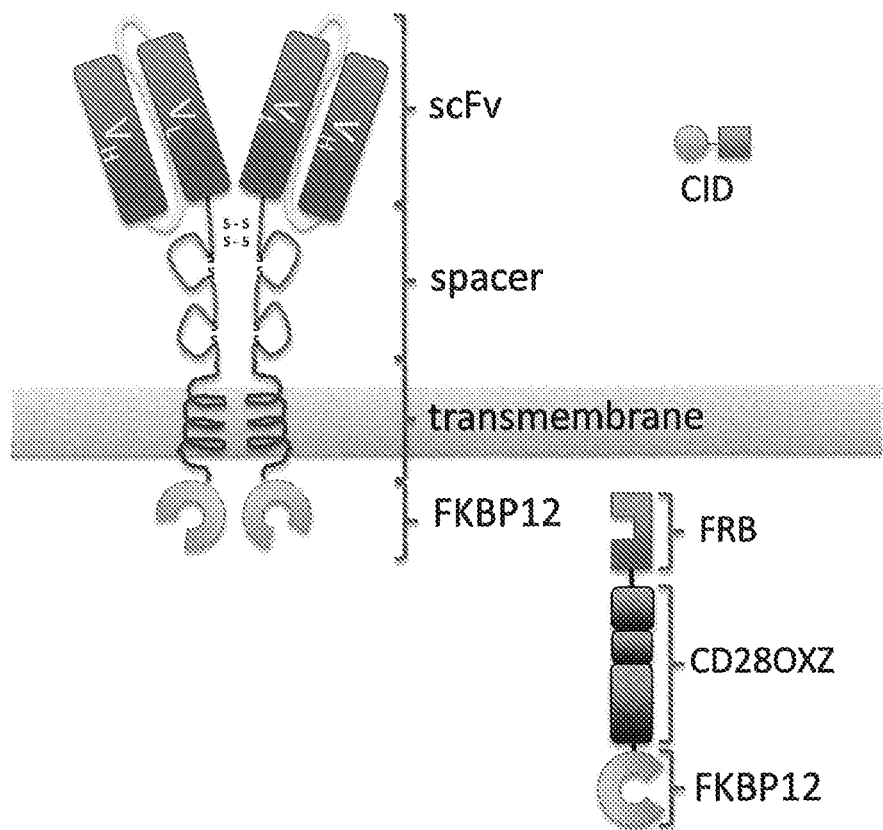
FIG. 8—Illustration of an inducible CAR with signalling component which comprises of two CID binding domains. In this example, there is one receptor component which comprises of a scFv, and Fc spacer, a transmembrane domain and an FKBP12 endodomain. The signalling domain comprises of the FRB domain of mTOR, a fusion of CD28, OX40 and Zeta endodomains and an FKBP12 domain. In the presence of CID, the signalling components multimerize with each other and with the receptor component. Upon antigen recognition, a signal equivalent to the sum of the signalling component multimer is transmitted.

In the case of very low density of target antigen expression, signalling strength may have to be amplified. Take for instance, the native T-cell receptor which is associated with multiple ITAM containing CD3 components. In such circumstances, signalling components can be modified to contain CBD2, a signalling domain and also a CBD1 (FIG. 8). In this way, addition of CID would lead to concatenation of multiple signalling components. The average size of the concatenation can be tuned by varying the amount of signalling components which have a CBD2. In the event of antigen recognition and in the presence of CID, signalling through the concatenation of multiple signalling components would be more potent than through individual signalling components.

Nucleic Acid

The third aspect of the invention relates to a nucleic acid encoding the receptor component of the second aspect and a nucleic acid encoding a signalling component of the third aspect.

The specific encoding nucleic acid sequences for four inducible CARs are given later in description, following the Examples section.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the second aspect of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid according to the third aspect of the invention may be a nucleic acid which encodes both the receptor component and the signalling component.

The nucleic acid may produce a polypeptide which comprises the receptor component and the signalling component joined by a cleavage site. The cleavage site may be self-cleaving, such that when the polypeptide is produced, it is immediately cleaved into the receptor component and the signalling component without the need for any external cleavage activity.

Various self-cleaving sites are known, including the Foot-and-Mouth disease virus (FMDV) 2a self-cleaving peptide, which has the sequence shown as SEQ ID No. 17 or SEQ ID No. 18:

SEQ ID No. 17
RAEGRGSLLTCGDVEENPGP.
or

SEQ ID No. 18
QCTNYALLKLAGDVESNPGP

Where the signalling system comprises a plurality of signalling components, each comprising a signalling domain and a CIDB2, the nucleic acid may have the general formula:

RC-coexpr1-SC1-coexpr2-SC2 wherein:
RC is a nucleic acid sequence encoding the receptor component;
Coexpr1 and coexpr2, which may be the same or different, are nucleic acid sequences allowing co-expression of the two flanking polypeptides (e.g. a sequence which encodes a cleavage site)
SC1 and SC2 are nucleic acid sequence encoding signalling components.

The signalling components encoded by SC1 and SC2 may bind the same CID, but have different endodomains. The nucleic acid construct may comprise nucleic acid sequences encoding more than two signalling components e.g. SC3, SC4 . . . up to SCx, each separated by a coexpression sequence, coexpr3, coexpr4 . . . up to coexprX.

The nucleic acid sequences encoding each component may be in any order, for example: RC-coexpr1-SC1-coexpr2-SC2; SC1-coexpr1-SC2-coexpr2-RC; or SC1-coexpr1-RC-coexpr2-SC2.

Where the signalling system comprises a plurality of receptor components, the nucleic acid may have the general formula:

RC1-coexpr1-RC2-coexpr2-SC wherein:
RC1 and RC2 are nucleic acid sequences encoding receptor components;
Coexpr1 and coexpr2, which may be the same or different, are nucleic acid sequences allowing co-expression of the two flanking polypeptides (e.g. a sequence which encodes a cleavage site)
SC is a nucleic acid sequence encoding the signalling component.

The receptor components may bind to different antigens but the same CID. They may have the same CIDB1. The nucleic acid construct may comprise nucleic acid sequences encoding more than two receptor components e.g. RC3, RC4 . . . up to RCx, each separated by a coexpression sequence, coexpr3, coexpr4 . . . up to coexprX.

The nucleic acid sequences encoding each component may be in any order, for example: RC1-coexpr1-RC2-coexpr2-SC; RC1-coexpr1-SC-coexpr2-RC2; or SC-coexpr1-RC1-coexpr2-RC2.

The co-expressing sequence may be an internal ribosome entry sequence (IRES). The co-expressing sequence may be an internal promoter.

The present invention also provides a kit comprising a nucleic acid encoding the receptor component of the second aspect and/or a nucleic acid encoding a signalling component of the third aspect. The kit may also comprise a heterodimerization agent which is suitable for use in the signalling system of the first aspect.

Vector

The present invention also provides a vector, or kit of vectors which comprises one or more nucleic acid sequence(s) encoding a receptor component of the second aspect and/or signalling component of the third aspect of the invention. Such a vector may be used to introduce the nucleic acid sequence(s) into a host cell so that it expresses the receptor component and signalling component of the CAR signalling system according to the first aspect of the invention. The kit may also comprise a CID which is suitable for use in the signalling system of the first aspect.

The vector may, for example, be a plasmid or a viral vector, such as a retroviral vector or a lentiviral vector, or a transposon based vector or synthetic mRNA.

The vector may be capable of transfecting or transducing a T cell.

Cytolytic Immune Cell

The present invention also relates to an immune cell comprising the CAR signalling system according to the first aspect of the invention.

Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing the molecules of the CAR signalling system according to the first aspect of the invention may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party).

Alternatively, T or NK cells expressing the molecules of the CAR signalling system according to the first aspect of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, CAR cells are generated by introducing DNA or RNA coding for the receptor component and signalling component by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR signalling system according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding the receptor component and/or signalling component of the CAR signalling system according to the second and third aspects of the invention.

The T or NK cells may then by purified, for example, selected on the basis of expression of the antigen-binding domain of the antigen-binding polypeptide.

The present invention also provides a kit which comprises a T or NK cell comprising the CAR signalling system according to the first aspect of the invention and a heterodimerization agent suitable for use in the signalling system.

Pharmaceutical Composition

The present invention also relates to a pharmaceutical composition containing a plurality of cytolytic immune cells expressing the molecules of the CAR signalling system of the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Methods

The present invention provides a method for treating and/or preventing a disease which comprises the step of administering the cytolytic immune cells of the present invention (for example in a pharmaceutical composition as described above) and/or a CID suitable for use in a signalling system according to the first aspect of the invention to a subject.

A method for treating a disease relates to the therapeutic use of the cytolytic immune cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cytolytic immune cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample from a subject;
(ii) transducing or transfecting such cells with a nucleic acid sequence or vector provided by the present invention;
(iii) administering the cells from (ii) to the subject.

The methods for treating a disease may further comprise the step of administering a CID suitable for use in the signalling system of the first aspect of the invention to the subject.

The present invention also provides a method for treating and/or preventing a disease in a subject which subject comprises cells of the invention, which method comprises the step of administering a CID agent suitable for use in the CAR signalling system according to the first aspect to the subject. As such, this method involves administering a suitable CID agent to a subject which already comprises CAR cells of the present invention.

The CID may be administered in the form of a pharmaceutical composition. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The methods for treating a disease provided by the present invention may involve monitoring the progression of the disease and monitoring any toxic activity and adjusting the dose of the CID administered to the subject to provide acceptable levels of disease progression and toxic activity.

Monitoring the progression of the disease means to assess the symptoms associated with the disease over time to determine if they are reducing/improving or increasing/worsening.

Toxic activities relate to adverse effects caused by the CAR cells of the invention following their administration to a subject. Toxic activities may include, for example, immunological toxicity, biliary toxicity and respiratory distress syndrome.

The level of signalling through the signalling system of the first aspect of the invention, and therefore the level of activation CAR cells expressing the signalling system, can be adjusted by altering the amount of CID present. In the present method the level of CAR cell activation may be augmented by increasing the dose of CID administered to the subject. Conversely, the level of CAR cell activation may be reduced by decreasing the dose of CID administered to the subject.

Higher levels of CAR cell activation are likely to be associated with reduced disease progression but increased toxic activities, whilst lower levels of CAR cell activation are likely to be associated with increased disease progression but reduced toxic activities.

As such the dose of CID administered to a subject may be altered in order to provide an acceptable level of both disease progression and toxic activity. The specific level of disease progression and toxic activities determined to be 'acceptable' will vary according to the specific circumstances and should be assessed on such a basis. The present invention provides a method for altering the activation level of the CAR cells in order to achieve this appropriate level.

The present invention provides a CAR cell of the present invention for use in treating and/or preventing a disease.

The invention also relates to the use of a CAR cell of the present invention in the manufacture of a medicament for the treatment and/or prevention of a disease.

The present invention also provides a CID agent suitable for activating a CAR signalling system according to the first aspect of the invention for use in treating and/or preventing a disease.

The present invention also provides a CID agent for use in activating a CAR signalling system according to the first aspect of the invention in a CAR cell.

The invention also provides the use of a CID suitable for activating a CAR signalling system according to the first aspect of the invention in the manufacture of a medicament for the treatment and/or prevention of a disease.

The invention also provides the use of a CID in the manufacture of a medicament for in activating a CAR signalling system according to the first aspect of the invention in a CAR cell.

The disease to be treated and/or prevented by the methods of the present invention may be an infection, such as a viral infection.

The methods of the invention may also be for the control of pathogenic immune responses, for example in autoimmune diseases, allergies and graft-vs-host rejection.

The methods may be for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

The CAR cells and pharmaceutical compositions of present invention may be for use in the treatment and/or prevention of the diseases described above.

The CAR cells and pharmaceutical compositions of present invention may be for use in any of the methods described above.

The present invention also provides a method of administering a cell according to the ninth aspect of the invention to a subject in need of same.

The present invention also provides a method of administering a CID as defined herein to a subject who comprises a cell according to the ninth aspect of the invention.

The invention will now be further described by way of Examples, which are meant to serve to assist one of ordinary skill in the art in carrying out the invention and are not intended in any way to limit the scope of the invention.

EXAMPLES

Example 1—A Rapamycin-Inducible CAR System

T-cells were transduced with a retroviral vector coding for an inducible CAR detailed in FIG. 3 and the sequence of which is shown as SEQ ID 19. This inducible CAR has a single receptor component and a single signalling component. The receptor component comprises of an anti-CD19 scFv, a spacer domain derived from human IgG1, a trans-membrane-domain derived from CD28 and FKBP12 as endodomain. The signalling component comprises of the FRB domain from mTOR and a signalling domain derived from endodomains of CD28, OX40 and CD3-Zeta. Expression of the CAR was determined by staining the transduced cells with a conjugated antibody recognizing the spacer domain and analysing by flow cytometry. The T-cells were incubated with either target cells expressing the cognate target CD19 in ratio of 2:1, 1:1 and 0:1 (target:effector) in the absence of rapamycin or at increasing concentrations. Signalling only occurred in the presence of both the cognate antigen and rapamycin. A dose response to rapamycin and target antigen was observed.

Example 2—An RSL1-Inducible CAR System

RSL1 is a synthetic non-steroidal analogue of 20-hydroxyecdysone (FIG. 9). It is a member of a class of insecticides known as diacylhydrazines and can function to act as a non-steroidal ecdysone agonist. These molecules induce premature moulting and larvae death but are well tolerated in vertebrates (Dhadialla et al (1998) Annu. Rev. Entomol. 43, 545-569). RSL1 has been used in artificial transcription switches (Lessard et al (2007) The Prostate 67, 808-819) whereby a two-protein transcription switch consisting of a fusion between the ecdysone receptor (EcR) and GAL4, and the retinoid X receptor (RXR) and VP16. In such systems, EcR is modified to interact specifically with RSL1 (Kumar et al (2004) J. Biol. Chem. 279, 27211-27218), and RXR is chimeric comprising of helices 1-8 replaced with helices 1-8 of human RXRβ, and helices 9-12 from *Locusta migratoria* RXR.

Figure 10:
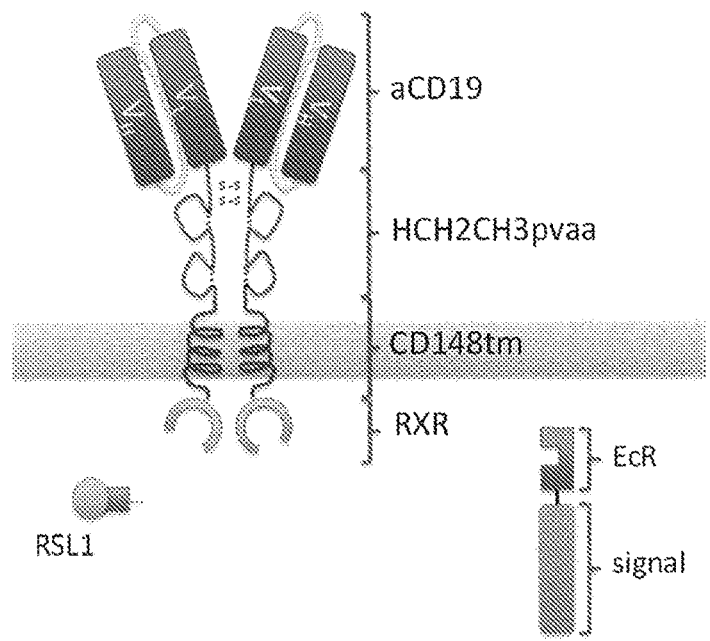
FIG. 10—RSL1 inducible CAR (a) an RSL1 inducible CAR was constructed by using retinoic acid receptor domains and ecodysone receptor domains to constitute the heterodimerization motifs for the antigen recognition component and the signalling component respectively. The antigen recognition component recognizes CD19. (b) T-cells expressing this CAR along with non-transduced T-cells were stained with anti-Fc which recognizes the CAR spacer. The transduced T-cells expressed the CAR well. (c) Transduced T-cells were next challenged with increasing concentration of RSL1 and challenged with either CD19 negative or CD19 positive target cells. T-cells challenged with CD19 positive targets signal only in the presence of RSL1.
Figure 10:
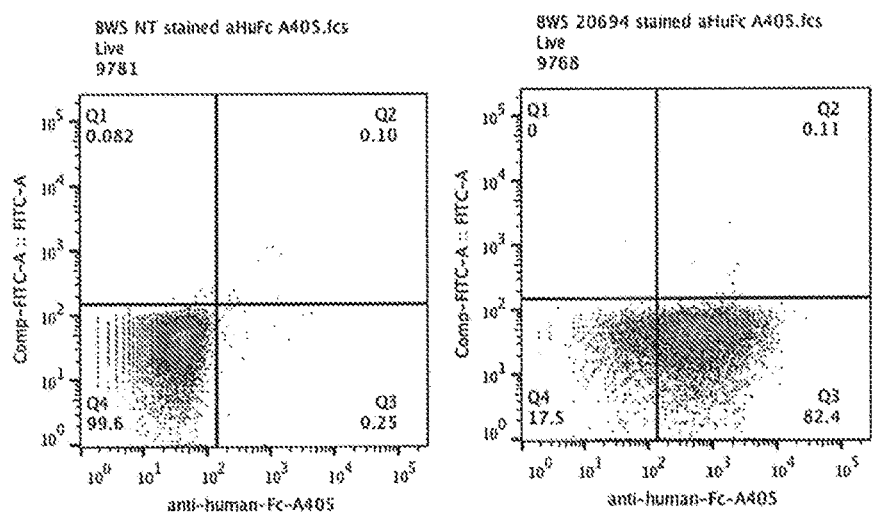
Figure 10:
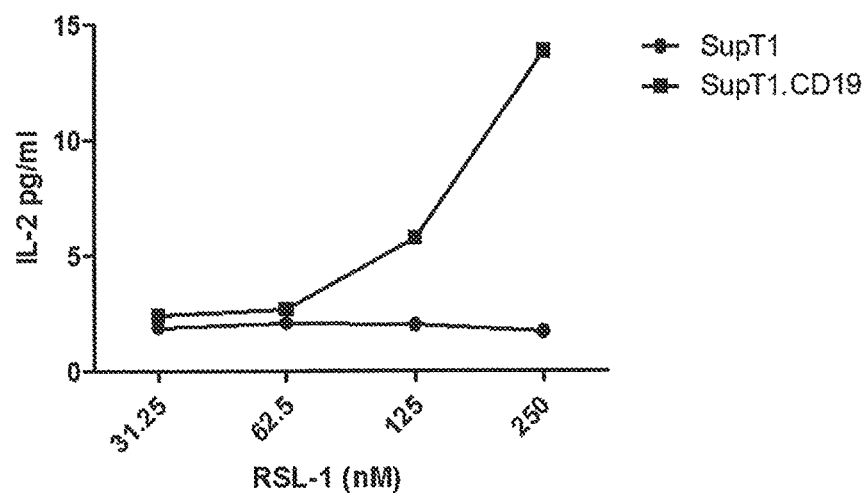

The present inventors have constructed a split CD19 CAR based on the CD19 system described in Example 1 with the heterodimerization motif on the antigen recognition component and signalling components being EcR and RXR respectively (FIG. 10*a* and SEQ ID No. 23). This CAR was transduced into T-cells and found to express well (FIG. 10*b*). These T-cells were challenged with targets which were CD19 negative and CD19 positive. Only CAR T-cells challenged with SupT1 targets in the presence of RSL1 released IL-2 (FIG. 10*c*).

Example 3—An AP1903-Inducible CAR System

Figure 11:
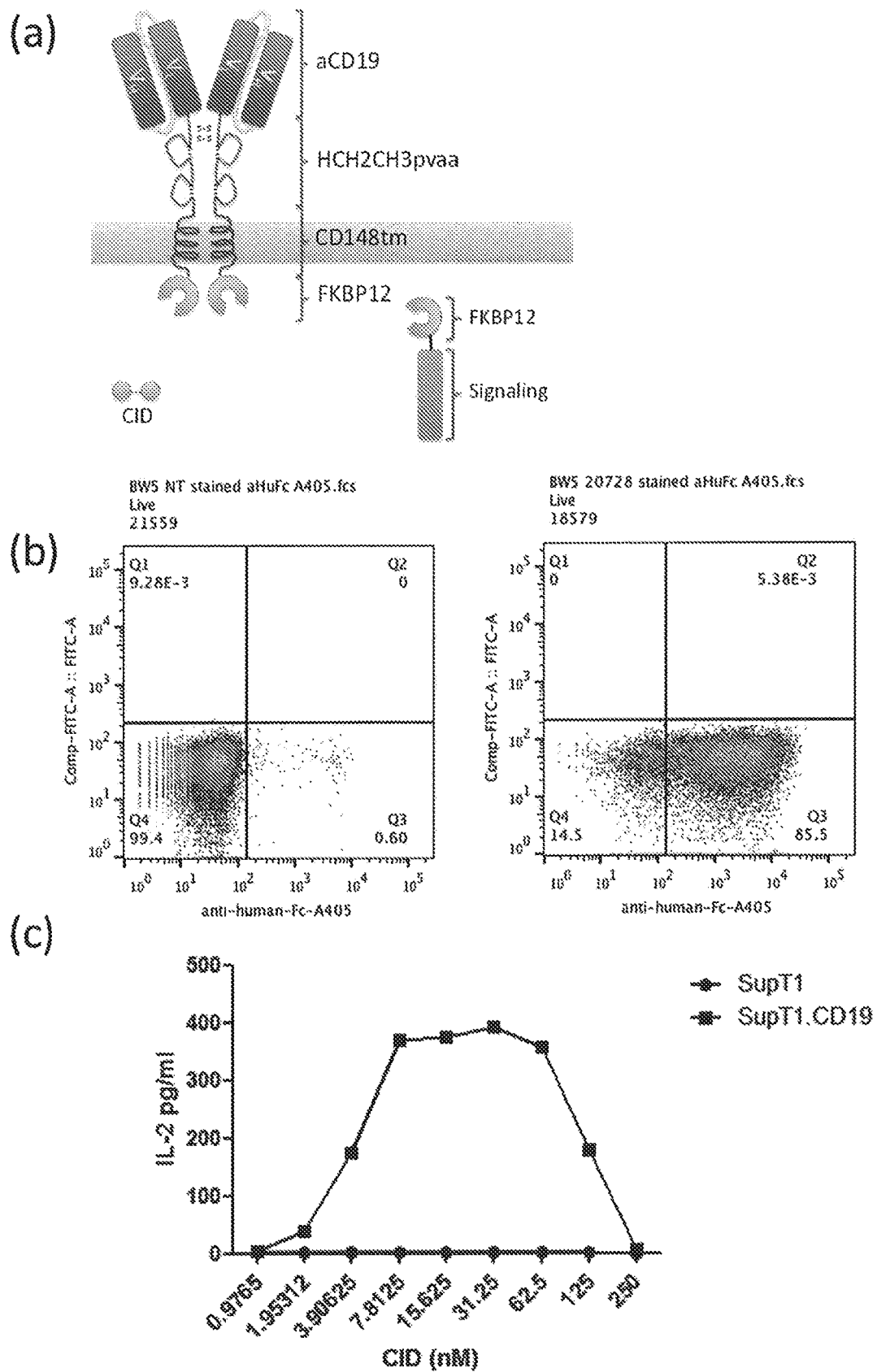
FIG. 11—AP1903 homodimerizer inducible CAR. (a) AP1903 homodimerizer inducible CAR was constructed by using modified FKBP12 domains to constitute the heterodimerization motifs for both the antigen recognition component and the signalling component. The antigen recognition component recognizes CD19. (b) T-cells expressing this CAR along with non-transduced T-cells were stained with anti-Fc which recognizes the CAR spacer. The transduced T-cells expressed the CAR well. (c) Transduced T-cells were next challenged with increasing concentration of CID dimerizer AP1903 and challenged with either CD19 negative or CD19 positive target cells. T-cells challenged with CD19 positive targets signal only in the presence of CID. At high CID concentrations, signalling is reduced likely to saturation of heterodimerization domains with an excess of CID reducing the formation of heterodimers.

AP1903 is a synthetic chemical inducer of dimerization which binds to two mutated FKB12 domains (Clackson et al (1998). Proc. Natl. Acad. Sci. U.S.A 95, 10437-10442). An inducible CAR was developed based on this system, using the modified FKBP12 domains to constitute the heterodimerization domain of both the antigen recognition component and signalling component in the framework as described in Example 1 with the antigen recognition domain and the signalling domain co-expressed with a FMD-2A like sequence (FIG. 11*a* and SEQ ID No. 24). The FKBP12 domains were codon-wobbled to prevent homologous recombination. T-cells were transduced with this construct and challenged with target cells which were CD19 negative or positive.

T-cells responded only to CD19 positive targets in the presence of AP1903 (FIG. 11*b*). At very high concentration of dimerizer, signalling was inhibited likely due to saturating conditions where the stoichiometry favours one FKBP12 binding a single dimerizer molecule rather than one dimerizer molecule binding two FKBP12 domains (FIG. 11*c*).

Specific Inducible Car-Encoding Sequences

SEQ ID No. 19. Simple inducible CAR comprised of one receptor component and one signalling component. The receptor component comprises of a signal peptide, an anti-CD19 scFv, a spacer from the Fc domain of human IgG1, a CD28 transmembrane domain and FKB12 as endodomain. A FMD-2A peptide separates this receptor component from the signalling component. The signalling component comprises of FRB and a compound of endodomains from CD28, OX40 and CD3-Zeta.

```
                                                         SgrAI
                                                       ---------
     1   atggagaccg acaccctgct gctgtggtg ctgctgctgt gggtgccagg cagcaccggc gacatccaga tgacccagac
         >>..................signal peptide...................>>
                                                                       >>.....aCD19 heavy chain......>

81   caccagcagc ctgagcgcca gcctgggcga ccgggtgacc atcagctgca gagccagcca ggacatcagc aagtacctga
         >.................................aCD19 heavy chain..................................>

161   actggtacca gcagaagccc gacggcaccg tgaagctgct gatctaccac accagccggc tgcacagcgg cgtgcccagc
         >.................................aCD19 heavy chain..................................>

XcmI
                                                      ----------------
   241   cggttcagcg gcagcggcag cggcaccgac tacagcctga ccatcagcaa cctggagcag gaggacatcg ccacctactt
         >.................................aCD19 heavy chain..................................>

321   ctgccagcag ggcaacaccc tgccctacac cttcggaggc ggcaccaagc tggagatcac caaggccgga ggcggaggct
         >............................aCD19 heavy chain...........................>>
                                                                                   >>...linker...>

401   ctggcggagg cggctctggc ggaggcggct ctggcggagg cggcagcgag gtgaagctgc aggagtctgg cccaggcctg
         >....................linker.....................>>
                                                        >>.........aCD19 light chain........>

481   gtggccccaa gccagagcct gagcgtgacc tgcaccgtga gcggcgtgag cctgcccgac tacggcgtga gctggatcag
         >.................................aCD19 light chain..................................>

561   gcagccccca cggaagggcc tggagtggct gggcgtgatc tgggcagcg agaccaccta ctacaacagc gccctgaaga
         >.................................aCD19 light chain..................................>

641   gccggctgac catcatcaag gacaacagca agagccaggt gttcctgaag atgaacagcc tgcagaccga cgacaccgcc
         >.................................aCD19 light chain..................................>

721   atctactact gcgccaagca ctactactat ggcggcagct acgctatgga ctactgggc cagggcacca gcgtgaccgt
         >.................................aCD19 light chain..................................>

BamHI                                                                         FseI
            ---------                                                                    ---------
   801   gagctcggat cccgccgagc ccaaatctcc tgacaaaact cacacatgcc caccgtgccc agcacctccc gtggccggcc
         >.>>
                    >>.........................HCH2CH3pvaa.........................>

881   cgtcagtctt cctcttcccc ccaaaaccca aggacaccct catgatcgcc cggacccctg aggtcacatg cgtggtggtg
         >................................HCH2CH3pvaa..................................>

961   gacgtgagcc acgaagaccc tgaggtcaag ttcaactggt acgtggacgg cgtggaggtg cataatgcca agacaaagcc
         >................................HCH2CH3pvaa..................................>
```

-continued

```
        SacII
        ------
1041  gcgggaggag cagtacaaca gcacgtaccg tgtggtcagc gtcctcaccg tcctgcacca ggactggctg aatggcaagg
         >...........................HCH2CH3pvaa.....................................>

1121  agtacaagtg caaggtctcc aacaaagccc tcccagcccc catcgagaaa accatctcca aagccaaagg gcagccccga
         >...........................HCH2CH3pvaa.....................................>

1201  gaaccacagg tgtacaccct gccccatcc cgggatgagc tgaccaagaa ccaggtcagc ctgacctgcc tggtcaaagg
         >...........................HCH2CH3pvaa.....................................>

1281  cttctatccc agcgacatcg ccgtggagtg ggagagcaat gggcaaccgg agaacaacta caagaccacg cctcccgtgc
         >...........................HCH2CH3pvaa.....................................>

1361  tggactccga cggctccttc ttcctctaca gcaagctcac cgtggacaag agcaggtggc agcaggggaa cgtcttctca
         >...........................HCH2CH3pvaa.....................................>

Ppu10I
              -------
              NsiI
              -------
              BfrBI
              -------
1441  tgctccgtga tgcatgaggc cctgcacaat cactataccc agaaatctct gagtctgagc ccaggcaaga aggaccccaa
         >...........................HCH2CH3pvaa.................................>>

1521  gttctgggtc ctggtggtgg tgggaggcgt gctggcctgt tactctctcc tggtgaccgt ggccttcatc atcttctggg
         >>.........................CD28tm........................................>

1601  tgggagtgca ggtggaaacc atctccccag gagacgggcg caccttcccc aagcgcggcc agacctgcgt ggtgcactac
         >>.........................FKBP12........................................>

1681  accgggatgc ttgaagatgg aaagaaattc gattcctccc gggacagaaa caagcccttt aagtttatgc taggcaagca
         >>.........................FKBP12........................................>

1761  ggaggtgatc cgaggctggg aagaaggggt tgcccagatg agtgtgggtc agagagccaa actgactata tctccagatt
         >>.........................FKBP12........................................>

1841  atgcctatgg tgccactggg cacccaggca tcatcccacc acatgccact ctcgtcttcg atgtggagct tctaaaactg
         >>.........................FKBP12........................................>

1921  gaacgcgcag agggccgggg ctcattgctg acctgtggag atgtcgagga aaatcccggc ccaatggctt ctagaatcct
      >>>
         >>.........................2A........................>>
                                                                                   >>..>

2001  ctggcatgag atgtggcatg aaggcctgga agaggcatct cgtttgtact ttggggaaag gaacgtgaaa ggcatgtttg
         >..............................FRB......................................>

SphI
              -------
2081  aggtgctgga gcccttgcat gctatgatgg aacggggccc ccagactctg aaggaaacat ccttttaatca ggcctatggt
         >..............................FRB......................................>

2161  cgagatttaa tggaggccca agagtggtgc aggaagtaca tgaaatcagg gaatgtcaag gacctcctcc aagcctggga
         >..............................FRB......................................>

XhoI
                                              ------
2241  cctctattat catgtgttcc gacgaatctc aaagctcgag agtggcggag gaggcagttc aaggtccgcc gacgcgcctg
         >...............FRB...............>>
                                         >>................CD28OXZ....................>

2321  cataccagca ggggcagaat cagctgtaca acgagctcaa cctcggtagg gcgcgaggaat acgatgtgct cgataagaga
         >.........................CD28OXZ......................................>

NruI
              -------
2401  agaggtcgcg atcccgagat gggaggaaaa cctcagcgcc gcaagaaccc tcaggagggg ctgtataacg aactgcagaa
         >.........................CD28OXZ......................................>

SfiI
                                                                              -------------
2481  ggataagatg gcagaggcct actccgagat tggcatgaag ggtgagagga agaggtaa aggccatgac ggcctctacc
         >.........................CD28OXZ......................................>

2561  aaggcctctc taccgcaacg aaagacactt atgacgctct gcatatgcag gctctccccc ctaggcagtg cactaattac
         >.........................CD28OXZ......................................>
```

```
2641  gcccttctga aacttgccgg cgatgtggag tctaaccctg gccctatcct gtggcacgag atgtggcatg agggtctgga
      >........................................CD28OXZ........................................>

2721  agaggccagc cggctgtact tcggagagag aaatgttaag ggtatgttcg aggtgctgga gccgcttcac gctatgatgg
      >........................................CD28OXZ........................................>

2801  agaggggccc ccagaccctc aaagaaacca gcttcaatca agcctacggg agggatctta tggaggcaca ggaatggtgt
      >........................................CD28OXZ........................................>

2881  cggaagtaca tgaagagcgg gaacgtcaag gacctgctcc aggcttggga tttgtattat cacgtcttta ggcggatcag
      >........................................CD28OXZ........................................>

2961  caagtctgga ggcggaggaa gtctgcacag cgattacatg aacatgaccc cccgaaggcc cggacccaca cgcaaacact
      >........................................CD28OXZ........................................>

3041  atcaacccta tgctccccca cgcgacttcg ccgcctaccg gtcacgcgcc gaggggcgcg gctctttgtt gacttgcggg
      >........................................CD28OXZ........................................>

3121  gacgttgaag agaatcctgg ccccatcctt tggcacgaga tgtggcacga gggcctggag aagcctccc ggctgtattt
      >........................................CD28OXZ........................................>

3201  cggagagcgc aacgtcaaag gaatgtttga ggtgctggag cctctccatg caatgatgga gaggggcct cagactctta
      >........................................CD28OXZ........................................>

3281  aagaaacatc ctttaatcag gcttacggta gagatttgat ggaggctcaa gaatggtgcc ggaaatacat gaagagtgga
      >........................................CD28OXZ........................................>

3361  aacgttaaag acctgctgca ggcatgggac ctgtactatc acgtattcag acggatctca aagtcagggg gaggtggctc
      >........................................CD28OXZ........................................>

3441  cctttatatc ttcaagcagc ctttcatgag gccggtgcag accacacaag aagaggatgg gtgctcttgc cggttccccg
      >........................................CD28OXZ........................................>

3521  aggaggagga gggcggatgc gagctctga
      >..........CD28OXZ...........>>
```

SEQ ID No. 20. Inducible CAR comprised of two receptor component and one signalling component. The first receptor component comprises of a signal peptide, an anti-CD19 scFv, a spacer from the stalk region of CD8, a transmembrane domain from CD28, and FKB12 as an endodomain. The second signalling component comprises of an anti-CD29 scFv, spacer derived from the Fc domain of human IgG1, a CD28 transmembrane domain and FKB12 as endodomain. The signalling component comprises of FRB and a compound of endodomains from CD28, OX40 and CD3-Zeta. A foot-and-mouth disease 2A peptide separates the components.

```
  1  atgagcctgc ccgtgaccgc cctgctgctg cccctggccc tgctgctgca cgccgccaga ccagacatcc agatgaccca
     >>....................signal peptide 1....................>>
                                                                >>.......aCD19_scFv........>

81  gaccaccagc agcctgagcg ccagcctggg cgaccgggtg accatcagct gcagagccag ccaggacatc agcaagtacc
     >........................................aCD19_scFv........................................>

161  tgaactggta ccagcagaag cccgacggca ccgtgaagct gctgatctac cacaccagcc ggctgcacag cggcgtgccc
     >........................................aCD19_scFv........................................>

241  agccggttca gcggnagcgg cagcggcacc gactacagcc tgaccatcag caacctggag caggaggaca tcgccaccta
     >........................................aCD19_scFv........................................>

321  cttctgccag cagggcaaca ccctgcccta caccttcgga ggcggcacca agctggagat caccaaggcc ggaggcggag
     >........................................aCD19_scFv........................................>

401  gctctggcgg aggcggctct ggcggaggcg gctctggcgg aggcggcagc gaggtgaagc tgcaggagtc tggcccaggc
     >........................................aCD19_scFv........................................>

481  ctggtggccc caagccagag cctgagcgtg acctgcaccg tgagcggcgt gagcctgccc gactacggcg tgagctggat
     >........................................aCD19_scFv........................................>

561  caggcagccc ccacggaagg gcctggagtg gctgggcgtg atctgggca gcgagaccac ctactacaac agcgccctga
     >........................................aCD19_scFv........................................>

641  agagccggct gaccatcatc aaggacaaca gcaagagcca ggtgttcctg aagatgaaca gcctgcagac cgacgacacc
     >........................................aCD19_scFv........................................>

721  gccatctact actgcgccaa gcactactac tatggcggca gctacgctat ggactactgg ggccagggca ccagcgtgac
     >........................................aCD19_scFv........................................>
```

```
                                                    SgrAI
                                                  ---------
 801  cgtgagctca gatcccacca cgacgccagc gccgcgacca ccaacaccgg cgcccaccat cgcgtcgcag ccccctgtcc
      >....>>
                    >>................................CD8STK..................................>

881  tgcgcccaga ggcgtgccgg ccagcggcgg ggggcgcagt gcacacgagg gggctggact tcgcctgtga tatctttgg
      >...............................CD8STK..................................>>
                                                                                   >>...>

961  gtgctggtgg tggttggtgg agtcctggct tgctatagct tgctagtaac agtggccttc atcatcttct gggtgggagt
      >...............................CD28tmZ...................................>>
                                                                                   >>..>

1041  gcaggtggaa accatctccc caggagacgg cgcaccttc cccaagcgcg ccagacctg cgtggtgcac tacaccggga
      >...............................FKBP12....................................>>

1121  tgcttgaaga tggaaagaaa ttcgattcct cccgggacag aaacaagccc tttaagttta tgctaggcaa gcaggaggtg
      >...............................FKBP12....................................>>

1201  atccgaggct gggaagaagg ggttgcccag atgagtgtgg gtcagagagc caaactgact atatctccag attatgccta
      >...............................FKBP12....................................>>

1281  tggtgccact gggcacccag gcatcatccc accacatgcc actctcgtct tcgatgtgga gcttctaaaa ctggaacgag
      >...............................FKBP12....................................>>
                                                                                   >>.>

NcoI
                                                  ------
1361  ccgagggcag gggaagtctt ctaacatgcg gggacgtgga ggaaaatccc gggccatgg agaccgacac cctgctgctg
      >...........................2A..................>>
                                                       >>...signal peptide 2....>

1441  tgggtgctgc tgctgtgggt gcccggcagc accggccagg tgcagctgca gcagcccggc gccgagctgg tgaagcccgg
      >..........signal peptide 2.....................>>
                                                       >>......aCD20_scFv.................>

1521  cgccagcgtg aagatgagct gcaaggccag cggctacacc ttcaccagct acaacatgca ctgggtgaag cagacccccg
      >.............................aCD20_scFv..................................>

1601  gccggggcct ggagtggatc ggcgccatct accccggcaa cggcgacacc agctacaacc agaagttcaa gggcaaggcc
      >.............................aCD20_scFv..................................>

2681  accctgaccg ccgacaagag cagcagcacc gcctacatgc agctgagcag cctgaccagc gaggacagcc ccgtgtacta
      >.............................aCD20_scFv..................................>

1761  ctgcgcccgg agcacctact acggcggcga ctggtacttc aacgtgtggg gcgccggcac caccgtgacc gtgagcggag
      >.............................aCD20_scFv..................................>

1841  gcggcggcag cggaggaggc ggctctgggg gaggcggatc tcagatcgtg ctgagccaga gccccgccat cctgagcgcc
      >.............................aCD20_scFv..................................>

1921  agccccggcg agaaggtgac catgacctgc cgggccagca gcagcgtgag ctacatccac tggttccagc agaagcccgg
      >.............................aCD20_scFv..................................>

BstXI
                                                  --------------
2001  cagcagcccc aagccctgga tctacgccac cagcaacctg gccagcggcg tgcccgtgcg gttcagcggc agcggcagcg
      >.............................aCD20_scFv..................................>

2081  gcaccagcta cagcctgacc atcagccggg tggaggccga ggacgccgcc acctactact gccagcagtg gaccagcaac
      >.............................aCD20_scFv..................................>

BamHI
                                                  ------
2161  ccacccacct tcggcggcgg caccaagctg gagatcaagc ggtcggatcc cgccgagccc aaatctcctg acaaaactca
      >----------------aCD20_scFv.................>>
                                                       >>......HCH2CH3pvaa'........>

FseI
                                                  --------
2241  cacatgccca ccgtgcccag cacctcccgt ggccggcccg tcagtcttcc tcttcccccc aaaacccaag gacaccctca
      >.............................HCH2CH3pvaa'................................>

2321  tgatcgcccg gacccctgag gtcacatgcg tggtggtgga cgtgagccac gaagaccctg aggtcaagtt caactggtac
      >.............................HCH2CH3pvaa'................................>

2401  gtggacggcg tggaggtgca taatgccaag acaaagccgc gggaggagca gtacaacagc acgtaccgtg tggtcagcgt
      >.............................HCH2CH3pvaa'................................>
```

-continued

```
2481  cctcaccgtc ctgcaccagg actggctgaa tggcaaggag tacaagtgca aggtctccaa caaagccctc ccagccccca
      >.................................HCH2CH3pvaa'.....................................>

2561  tcgagaaaac catctccaaa gccaagggc agccccgaga ccacaggtg tacaccctgc ccccatcccg ggatgagctg
      >.................................HCH2CH3pvaa'.....................................>

2641  accaagaacc aggtcagcct gacctgcctg gtcaaaggct tctatcccag cgacatcgcc gtggagtggg agagcaatgg
      >.................................HCH2CH3pvaa'.....................................>

2721  gcaaccggag aacaactaca agaccacgcc tcccgtgctg gactccgacg gctccttctt cctctacagc aagctcaccg
      >.................................HCH2CH3pvaa'.....................................>

Ppu10I
                                                      -------
                                                       NsiI
                                                      -------
                                                      BfrBI
                                                      -------
2801  tggacaagag caggtggcag caggggaacg tcttctcatg ctccgtgatg catgaggccc tgcacaatca ctatacccag
      >.................................HCH2CH3pvaa'.....................................>

2881  aaatctctga gtctgagccc aggcaagaag gaccccaagt tctgggtcct ggtggtggtg ggaggcgtgc tggcctgtta
      >.......HCH2CH3pvaa'.......>>
                                              >>...................CD28tm....................>

2961  ctctctcctg gtgaccgtgg ccttcatcat cttctgggtg ggagtgcagg tggaaaccat ctccccagga cgggcgca
      >.................CD28tn.................>>
                                 >>.................FKBP12....................>

3041  ccttccccaa gcgcggccag acctgcgtgg tgcactacac cgggatgctt gaagatggaa agaaattcga ttcctcccgg
      >..........................FKBP12..........................................>

3121  gacagaaaca agccctttaa gttatgcta ggcaagcagg aggtgatccg aggctgggaa gaaggggttg cccagatgag
      >..........................FKBP12..........................................>

3201  tgtgggtcag agagccaaac tgactatatc tccagattat gcctatggtg ccactgggca cccaggcatc atcccaccac
      >..........................FKBP12..........................................>

3281  atgccactct cgtcttcgat gtggagcttc taaaactgga acgcgcagag gccggggct cattgctgac ctgtggagat
      >................FKBP12..................>>
                                              >>..................2A....................>

3361  gtcgaggaaa atcccggccc aatggcttct agaatcctct ggcatgagat gtggcatgaa ggcctggaag aggcatctcg
      >.........2A.........>>
                                              >>......................FRB........................>

SphI
                                                      ------
3441  tttgtacttt ggggaaagga acgtgaaagg catgtttgag gtgctggagc ccttgcatgc tatgatggaa cggggccccc
      >.........................................FRB..........................................>

3521  agactctgaa ggaaacatcc tttaatcagg cctatggtcg agatttaatg gaggcccaag agtggtgcag gaagtacatg
      >.........................................FRB..........................................>

XhoI
                                                                                        ------
3601  aaatcaggga atgtcaagga cctcctccaa gcctgggacc tctattatca tgtgttccga cgaatctcaa agctcgagta
      >.........................FRB.........................................>>
                                                                                          >>

3681  tagcggcggc ggcagcagga gtaagaggag caggctcctg cacagtgact acatgaacat gactccccgc cgccccgggc
      >....linker....>>
                     >>.............................CD28OXZ...............................>

3761  ccacccgcaa gcattaccag ccctatgccc caccacgcga cttcgcagcc tatcgctcca gggaccagag gctgcccccc
      >..........................CD28OXZ..........................................>

3841  gatgccaca agccccctgg gggaggcagt tccggacccc catccaaga ggagcaggcc gacgcccact ccaccctggc
      >..........................CD28OXZ..........................................>

3921  caagatcaga gtgaagttca gcaggagcgc agacgccccc cgctaccagc agggccagaa ccagctctat aacgagctca
      >..........................CD28OXZ..........................................>

4001  atctaggacg aagagaggag tacgatgttt tggacaagag acgtggccgg gaccctgaga tgggggggaaa gccgagaagg
      >..........................CD28OXZ..........................................>

4081  aagaaccctc aggaaggcct gtacaatgaa ctgcagaaag ataagatggc ggaggcctac agtgagattg ggatgaaagg
      >..........................CD28OXZ..........................................>

4161  cgagcgccgg agggggcaagg ggcacgatgg cctttaccag ggtctcagta cagccaccaa ggacacctac gacgcccttc
      >..........................CD28OXZ..........................................>
```

```
4241  acatgcaggc cctgcctcct cgctaa
      >.........CD28OXZ.........>>
```

SEQ ID No. 21. Inducible CAR comprised of one receptor component and three signalling components. The receptor component comprises of a signal peptide, an anti-CD19 scFv, a spacer derived from the Fc domain of human IgG1, a CD28 transmembrane domain and FKB12 as endodomain. The first signalling component comprises of FRB and endodomain from CD3 Zeta, the second comprises FRB and CD28 endodomain, the third FRB and 41BB endodomain. A foot-and-mouth disease 2A peptide separates the components.

```
                                               SgrAI
                                             ---------
    1  atggagaccg acaccctgct gctgtgggtg ctgctgctgt gggtgccagg cagcaccggc gacatccaga tgacccagac
       >>...................signal peptide...................>>
                                                             >>.......scFv anti-D19........>

81  caccagcagc ctgagcgcca gcctgggcga ccgggtgacc atcagctgca gagccagcca ggacatcagc aagtacctga
       >....................................scFv anti-CD19.....................................>

161  actggtacca gcagaagccc gacggcaccg tgaagctgct gatctaccac accagccggc tgcacagcgg cgtgcccagc
       >....................................scFv anti-CD19.....................................>

XcmI
                                          ................
  241  cggttcagcg gcagcggcag cggcaccgac tacagcctga ccatcagcaa cctggagcag gaggacatcg ccacctactt
       >....................................scFv anti-CD19.....................................>

321  ctgccagcag ggcaacaccc tgccctacac cttcggaggc ggcaccaagc tggagatcac caaggccgga ggcggaggct
       >....................................scFv anti-CD19.....................................>

401  ctggcggagg cggctctggc ggaggcggct ctggcggagg cggcagcgag gtgaagctgc aggagtctgg cccaggcctg
       >....................................scFv anti-CD19.....................................>

481  gtggccccaa gccagagcct gagcgtgacc tgcaccgtga gcggcgtgag cctgcccgac tacggcgtga gctggatcag
       >....................................scFv anti-CD19.....................................>

561  gcagcccca cggaagggcc tggagtggct gggcgtgatc tggggcagcg agaccaccta ctacaacagc gccctgaaga
       >....................................scFv anti-CD19.....................................>

641  gccggctgac catcatcaag gacaacagca gagccaggt gttcctgaag atgaacagcc tgcagaccga cgacaccgcc
       >....................................scFv anti-CD19.....................................>

721  atctactact gcgccaagca ctactactat ggcggcagct acgctatgga ctactggggc cagggcacca gcgtgaccgt
       >....................................scFv anti-CD19.....................................>

BamHI                                                                        FseI
              -------                                                                      --------
  801  gagctcggat cccgccgagc ccaaatctcc tgacaaaact cacacatgcc caccgtgccc agcacctccc gtggccggcc
       >.>>
                  >>.........................HCH2CH3pvaa.............................>

881  cgtcagtctt cctcttcccc ccaaaaccca aggacaccct catgatcgcc cggacccctg aggtcacatg cgtggtggtg
       >.......................................HCH2CH3pvaa.......................................>

961  gacgtgagcc acgaagaccc tgaggtcaag ttcaactggt acgtggacgg cgtggaggtg cataatgcca agacaaagcc
       >.......................................HCH2CH3pvaa.......................................>

SacII
       -----
 1041  gcgggaggag cagtacaaca gcacgtaccg tgtggtcagc gtcctcaccg tcctgcacca ggactggctg aatggcaagg
       >.......................................HCH2CH3pvaa.......................................>

1121  agtacaagtg caaggtctcc aacaaagccc tcccagcccc catcgagaaa accatctcca aagccaaagg gcagcccga
       >.......................................HCH2CH3pvaa.......................................>

1201  gaaccacagg tgtacaccct gcccccatcc cgggatgagc tgaccaagaa ccaggtcagc ctgacctgcc tggtcaaagg
       >.......................................HCH2CH3pvaa.......................................>

1281  cttctatccc agcgacatcg ccgtggagtg ggagagcaat gggcaaccgg agaacaacta caagaccacg cctcccgtgc
       >.......................................HCH2CH3pvaa.......................................>
```

```
                                               -continued
1361  tggactccga cggctccttc ttcctctaca gcaagctcac cgtggacaag agcaggtggc agcagggga cgtcttctca
      >.....................................HCH2CH3pvaa......................................>
                  Ppu10I
                  -------
                  NsiI
                  -------
                  BfrBI
                  -------
1441  tgctccgtga tgcatgaggc cctgcacaat cactataccc agaaatctct gagtctgagc ccaggcaaga aggaccccaa
      >.....................................HCH2CH3pvaa........................>>

1521  gttctgggtc ctggtggtgg tgggaggcgt gctggcctgt tactctctcc tggtgaccgt ggccttcatc atcttctggg
      >>.................................................CD28tm.....................................>

1601  tgggagtgca ggtggaaacc atctccccag agacgggcg caccttcccc aagcgcggcc agacctgcgt ggtgcactac
      >>
         >>.............................FKBP12.........................................>

1681  accgggatgc ttgaagatgg aaagaaattc gattcctccc gggacagaaa caagcccttt aagtttatgc taggcaagca
      >...............................FKBP12...........................................>

1761  ggaggtgatc cgaggctggg aagaaggggt tgcccagatg agtgtgggtc agagagccaa actgactata tctccagatt
      >...............................FKBP12...........................................>

1841  atgcctatgg tgccactggg cacccaggca tcatcccacc acatgccact ctcgtcttcg atgtggagct tctaaaactg
      >...............................FKBP12...........................................>

1921  gaacgcgcag agggccgggg ctcattgctg acctgtggag atgtcgagga aaatcccggc ccaatggctt ctagaatcct
      >>>
         >>...................FMD-2A..........................>>
                                                                                          >>.>

2001  ctggcatgag atgtggcatg aaggcctgga agaggcatct cgtttgtact ttggggaaag gaacgtgaaa ggcatgtttg
      >.....................................FRB............................................>
                  SphI
                  -------
2081  aggtgctgga gcccttgcat gctatgatgg aacggggccc ccagactctg aaggaaacat cctttaatca ggcctatggt
      >.....................................FRB............................................>

2161  cgagatttaa tggaggccca agagtggtgc aggaagtaca tgaaatcagg gaatgtcaag gacctcctcc aagcctggga
      >.....................................FRB............................................>
                                                XhoI
                                                ------
2241  cctctattat catgtgttcc gacgaatctc aaagctcgag agtggcggag gaggcagttc aaggtccgcc gacgcgcctg
      >...............FRB.................>>
                                              >>....linker.....>>
                                                                  >>.......CD3-Zeta...........>

2321  cataccagca ggggcagaat cagctgtaca acgagctcaa cctcggtagg cgcgaggaat acgatgtgct cgataagaga
      >...........................CD3-Zeta...............................................>
                  NruI
                  -------
2401  agaggtcgcg atcccgagat gggaggaaaa cctcagcgcc gcaagaaccc tcaggagggg ctgtataacg aactgcagaa
      >...........................CD3-Zeta...............................................>
                                                                          SfiI
                                                                          --------------
2481  ggataagatg gcagaggcct actccgagat tggcatgaag ggtgagagga agagggtaa aggccatgac ggcctctacc
      >...........................CD3-Zeta...............................................>

2561  aaggcctctc taccgcaacg aaagacactt atgacgctct gcatatgcag gctctccccc taggcagtg cactaattac
      >...........................CD3-Zeta...........................>>
                                                                        >>...FMD-2A..>

2641  gcccttctga acttgccgg cgatgtggag tctaaccctg ccctatcct gtggcacgag atgtggcatg agggtctgga
      >...................FMD-2A..................>>
                                                    >>................FRB.................>

2721  agaggccagc cggctgtact tcggagagag aaatgttaag ggtatgttcg aggtgctgga gccgcttcac gctatgatgg
      >.....................................FRB............................................>

2801  agaggggccc ccagaccctc aaagaaacca gcttcaatca gcctacggg agggatctta tggaggcaca ggaatggtgt
      >.....................................FRB............................................>

2881  cggaagtaca tgaagagcgg gaacgtcaag gacctgctcc aggcttggga tttgtattat cacgtcttta ggcggatcag
      >.....................................FRB............................................>
```

-continued

```
2961  caagtctgga ggcggaggaa gtctgcacag cgattacatg aacatgaccc cccgaaggcc cggacccaca cgcaaacact
      >.>>
           >>.....linker.....>>
                                >>............................CD28............................>
3041  atcaaccota tgctccccca cgcgacttcg ccgcctaccg tcacgcgcc gaggggcgcg gctctttgtt gacttgcggg
      >...................CD28......................>>
                                                >>...............FMD-2A................>
3121  gacgttgaag agaatcctgg ccccatcctt tggcacgaga tgtggcacga gggcctggag gaagcctccc ggctgtattt
      >........FMD-2A..........>>
                             >>............................FRB............................>
3201  cggagagcgc aacgtcaaag gaatgtttga ggtgctggag cctctccatg caatgatgga gaggggcct cagactctta
      >............................FRB............................>
3281  aagaaacatc ctttaatcag gcttacggta gagatttgat ggaggctcaa gaatggtgcc ggaaatacat gaagagtgga
      >............................FRB............................>
3361  aacgttaaag acctgctgca ggcatgggac ctgtactatc acgtattcag acggatctca aagtcagggg gcggtggctc
      >............................FRB...............................>>
                                                                      >>....linker.....>
3441  cctttatatc ttcaagcagc ctttcatgag gccggtgcag accacacaag aagaggatgg gtgctcttgc cggttcccg
      >................................41BB.........................................>
3521  aggaggagga gggcggatgc gagctctga
      >.............41BB...........>>
```

SEQ ID No. 22. Inducible CAR with multi-spanning receptor component. The receptor component comprises of a signal peptide, an anti-CD19 scFv, a spacer from the Fc domain of human IgG1, a CD28 transmembrane domain, a first FRB, then the first trans-membrane, minor extracellular loop and second transmembrane domain of CD20, then a second FRB, then the third transmembrane domain, the major extracellular loop and the fourth transmembrane domain of CD20, and a third FRB. The signalling component comprises of FRB and a compound of endodomains from CD28, OX40 and CD3-Zeta. A foot-and-mouth disease 2A peptide separates the two components.

```
                                    SgrAI
                                    ---------
   1  atggagaccg acaccctgct gctgtgggtg ctgctgctgt gggtgccagg cagcaccggc gacatccaga tgacccagac
      >...................signal peptide...................>>
                                                          >>........scFv anti-CD19........>
  81  caccagcagc ctgagcgcca gcctgggcga ccgggtgacc atcagctgca gagccagcca ggacatcagc aagtacctga
      >.....................................scFv anti-CD19.....................................>
 161  actggtacca gcagaagccc gacggcaccg tgaagctgct gatctaccac accagccggc tgcacagcgg cgtgcccagc
      >.....................................scFv anti-CD19.....................................>
                                    XcmI
                                    ----------------
 241  cggttcagcg gcagcggcag cggcaccgac tacagcctga ccatcagcaa cctggagcag gaggacatcg ccacctactt
      >.....................................scFv anti-CD19.....................................>
 321  ctgccagcag ggcaacaccc tgccctacac cttcggaggc ggcaccaagc tggagatcac caaggccgga ggcggaggct
      >.....................................scFv anti-CD19.....................................>
                                                                                          StuI
                                                                                          ------
 401  ctggcggagg cggctctggc ggaggcggct ctggcggagg cggcagcgag gtgaagctgc aggagtctgg cccaggcctg
      >.....................................scFv anti-CD19.....................................>
 481  gtggccccaa gccagagcct gagcgtgacc tgcaccgtga gcggcgtgag cctgcccgac tacggcgtga gctggatcag
      >.....................................scFv anti-CD19.....................................>
 561  gcagcccca cggaagggcc tggagtggct gggcgtgatc tggggcagcg agaccaccta ctacaacagc gccctgaaga
      >.....................................scFv anti-CD19.....................................>
 641  gccggctgac catcatcaag gacaacagca gagccaggt gttcctgaag atgaacagcc tgcagaccga cgacaccgcc
      >.....................................scFv anti-CD19.....................................>
 721  atctactact gcgccaagca ctactactat ggcggcagct acgctatgga ctactgggc cagggcacca gcgtgaccgt
      >.....................................scFv anti-CD19.....................................>
              BamHI                                                                        FseI
              -------                                                                      --------
```

```
                                              -continued
 801   gagctcggat cccgccgagc ccaaatctcc tgacaaaact cacacatgcc caccgtgccc agcacctccc gtggccggcc
       >..>>
                 >>...........................HCH2CH3pvaa...........................>

881   cgtcagtctt cctcttcccc ccaaaaccca aggacaccct catgatcgcc cggacccctg aggtcacatg cgtggtggtg
       >..........................HCH2CH3pvaa...........................................>

961   gacgtgagcc acgaagaccc tgaggtcaag ttcaactggt acgtggacgg cgtggaggtg cataatgcca agacaaagcc
       >..........................HCH2CH3pvaa...........................................>

SacII
       -----
1041   gcgggaggag cagtacaaca gcacgtaccg tgtggtcagc gtcctcaccg tcctgcacca ggactggctg aatggcaagg
       >..........................HCH2CH3pvaa...........................................>

1121   agtacaagtg caaggtctcc aacaaagccc tcccagcccc catcgagaaa accatctcca aagccaaagg gcagccccga
       >..........................HCH2CH3pvaa...........................................>

1201   gaaccacagg tgtacaccct gcccccatcc cgggatgagc tgaccaagaa ccaggtcagc ctgacctgcc tggtcaaagg
       >..........................HCH2CH3pvaa...........................................>

1281   cttctatccc agcgacatcg ccgtggagtg ggagagcaat gggcaaccgg agaacaacta caagaccacg cctcccgtgc
       >..........................HCH2CH3pvaa...........................................>

1361   tggactccga cggctccttc ttcctctaca gcaagctcac cgtggacaag agcaggtggc agcagggaa cgtcttctca
       >..........................HCH2CH3pvaa...........................................>

Ppu10I
                  -------
                  NsiI
                  -------
                  BfrBI
                  -------
1441   tgctccgtga tgcatgaggc cctgcacaat cactataccc agaaatctct gagtctgagc ccaggcaaga aggaccccaa
       >..........................HCH2CH3pvaa..........................>>

1521   gttctgggtc ctggtggtgg tgggaggcgt gctggcctgt tactctctcc tggtgaccgt ggccttcatc atcttctggg
       >..................................CD28tm..........................................>

StuI
                                             -------
1601   tgatcctctg gcatgagatg tggcatgaag gcctggaaga ggcatctcgt ttgtactttg gggaaggaa cgtgaaaggc
       >>
                 >>.........................FRB..........................................>

StuI
                                                                                        ------
1681   atgtttgagg tgctggagcc cttgcatgct atgatggaac ggggccccca gactctgaag gaaacatcct taatcaggc
       >..........................FRB....................................................>

1761   ctatggtcga gatttaatgg aggcccaaga gtggtgcagg aagtacatga atcagggaa tgtcaaggac ctcctccaag
       >..........................FRB....................................................>

1841   cctgggacct ctattatcat gtgttccgac gaatctcaaa gagcagcctg gtgggaccca ccagagcttc ttcatgcgg
       >...............FRB.................>>
                                             >>................CD20....................>

StuI
                                                           ------
1921   gagagcaaga ccctgggagc cgtgcagatc atgaacggcc tgttccacat cgccctggga ggcctgctga tgatccctgc
       >..........................CD20..................................................>

2001   cggcatctac gccccaatct gcgtgaccgt gtggtaccca ctgtggggag catcatgta catcatcagc ggcagcctgc
       >..........................CD20...................................................>

2081   tggccgccac cgagaagaac agcggagggg gaagcatcct gtggcacgag atgtggcatg agggtctgga gaggccagc
       >.......CD20.......>>
                           >>...linker...>>
                                          >>....................FRB......................>

2161   cggctgtact tcggagagag aaatgttaag ggtatgttcg aggtgctgga gccgcttcac gctatgatgg agggggccc
            >>..........................FRB............................................>

2241   ccagaccctc aaagaaacca gcttcaatca agcctacggg agggatctta tggaggcaca ggaatggtgt cggaagtaca
       >>..........................FRB....................................................>

2321   tgaagagcgg gaacgtcaag gacctgctcc aggcttggga tttgtattat cacgtcttta ggcggatcag caagtctgga
       >..........................FRB................................>>
                                                                         >>...>
```

```
2401  ggcggaggaa gtcggaagtg cctggtgaag ggcaagatga tcatgaacag cctgagcctg ttcgccgcca tcagcggcat
      >..linker..>>
                 >>................................CD20....................................>

2481  gatcctgagc atcatggaca tcctgaacat caagatcagc cacttcctga agatggagag cctgaacttc atccgggccc
      >...........................................CD20....................................>

2561  acacccata catcaacatc tacaactgcg agcctgccaa ccccagcgag aagaacagcc cagcaccca gtactgctac
      >...........................................CD20....................................>

BsaBI
                                              -----------
2641  agcatccaga gcctgttcct gggcatcctg agcgtgatgc tgatcttcgc cttcttccag gagctggtga tcgccggcat
      >...........................................CD20....................................>

2721  cgtggagaac gagtggaagc ggacctgcag ccggcccaag agcatcctgt ggcacgagat gtggcatgag ggtctggaag
      >....................CD20....................>>
                                                   >>.................FRB..................>

2801  aggccagccg gctgtacttc ggagagagaa atgttaaggg tatgttcgag gtgctggagc cgcttcacgc tatgatggag
      >...........................................FRB.....................................>

2881  aggggccccc agaccctcaa agaaaccagc ttcaatcaag cctacgggag ggatcttatg gaggcacagg aatggtgtcg
      >...........................................FRB.....................................>

2961  gaagtacatg aagagcggga acgtcaagga cctgctccag gcttgggatt tgtattatca cgtctttagg cggatcagca
      >...........................................FRB.....................................>

3041  agcgcgcaga gggccggggc tcattgctga cctgtgagga tgtcgaggaa atcccggcc caggagtgca ggtggaaacc
      >>>
         >>...........................FMD-2A...........................>>
                                                                         >>.....FKBP12.....>

3121  atctccccag gagacgggcg caccttcccc aagcgcggcc agacctgcgt ggtgcactac accgggatgc ttgaagatgg
      >.........................................FKBP12....................................>

3201  aaagaaattc gattcctccc gggacagaaa caagcccttt aagtttatgc taggcaagca ggaggtgatc cgaggctggg
      >.........................................FKBP12....................................>

3281  aagaaggggt tgcccagatg agtgtgggtc agagagccaa actgactata tctccagatt atgcctatgg tgccactggg
      >.........................................FKBP12....................................>

3361  cacccaggca tcatcccacc acatgccact ctcgtcttcg atgtggagct tctaaaactg gaaaggagta agaggagcag
      >...........................FKBP12.............................>>
                                                                         >>.....28OXZ.....>

3441  gctcctgcac agtgactaca tgaacatgac tccccgccgc cccgggccca cccgcaagca ttaccagccc tatgccccac
      >...........................................28OXZ...................................>

3521  cacgcgactt cgcagcctat cgctccaggg accagaggct gccccccgat gcccacaagc cccctggggg aggcagtttc
      >...........................................28OXZ...................................>

3601  cggaccccca tccaagagga gcaggccgac gcccactcca ccctggccaa gatcagagtg aagttcagca ggagcgcaga
      >...........................................28OXZ...................................>

3681  cgccccgcg taccagcagg gccagaacca gctctataac gagctcaatc taggacgaag agaggagtac gatgttttgg
      >...........................................28OXZ...................................>

3761  acaagagacg tggccgggac cctgagatgg ggggaaagcc gagaaggaag aaccctcagg aaggcctgta caatgaactg
      >...........................................28OXZ...................................>

3841  cagaaagata agatggcgga ggcctacagt gagattggga tgaaaggcga gcgccggagg ggcaaggggc acgatggcct
      >...........................................28OXZ...................................>

3921  ttaccagggt ctcagtacag ccaccaagga cacctacgac gcccttcaca tgcaggccct gcctcctcgc tga
      >...........................................28OXZ..................................>>
```

SEQ ID No. 23. Simple inducible CAR comprised of one receptor component and one signalling component. The signalling component comprises an ecdysone receptor and the CD3-Zeta endodomain (italic). A FMD-2A peptide (shown in bold) separates this signalling component from the receptor component. The receptor component comprises an anti-CD19 scFv, a HCH2CH3 spacer (underlined), a CD148 transmembrane domain (highlighted in grey) and the retinoid X receptor as endodomain.

SEQ ID No. 23

MPVDRILEAELAVEQKSDQGVEGPGGTGGSGSSPNDPVTNICQAADKQLFTLVEWAKRIP
HFSSLPLDDQVILLRAGWNELLIASFSHRSIDVRDGILLATGLHVHRNSAHSAGVGAIFD
RVLTELVSKMRDMRMDKTELGCLRAIILFNPEVRGLKSAQEVELLREKVYAALEEYTRTT
HPDEPGRFAKLLLRLPSLRSIGLKCLEHLFFFRLIGDVPIDTFLMEMLESPSDSSGGGSA
*DAPAYQQGQNQLYNELNLGRREEYDVLDKRRGRDPEMGGKPRRKNPQEGLYNELQKDKMA*
*EAYSEIGMKGERRRGKHDGLYQGLSTATKDTYDALHMQALPPR*RAEGRGSLLTCGDVEE
NPGPMETDTLLLWVLLLWVPGSTGDIQMTQTTSSLSASLGDRVTISCRASQDISKYLNWY
QQKPDGTVKLLIYHTSRLHSGVPSRFSGSGSGTDYSLTISNLEQEDIATYFCQQGNTLPY
TFGGGTKLEITKAGGGGSGGGGSGGGGSGGGGSEVKLQESGPGLVAPSQSLSVTCTVSGV
SLPDYGVSWIRQPPRKGLEWLGVIWGSETTYYNSALKSRLTIIKDNSKSQVFLKMNSLQT
DDTAIYYCAKHYYYGGSYAMDYWGQGTSVTVSSDP<u>AEPKSPDKTHTCPPCPAPPVAGPSV</u>
<u>FLFPPKPKDTLMIARTPEVICVVVDVSHEDPEVKFNWYVDGVEVHNAKTKPREEQYNSTY</u>
<u>RVVSVLTVLHQDWLNGKEYKCKVSNKALPAPIEKTISKAKGQPREPQVYTLPPSRDELTK</u>
<u>NQVSLTCLVKGFYPSDIAVEWESNGQPENNYKTTPPVLDSDGSFFLYSKLTVDKSRWQQG</u>
<u>NVFSCSVMHEALHNHYTQKSLSLSPGKKD</u>PMALIVLGGVAGLLLFIGLGIFFCVRCRHRR
RQAERMSQIKRLLSEKKTCQCHRFQKTCSPISGGGGSRPECVVPETQCAMKRKEKKAQK
EKDKLPVSTTTVDDHMPPIMQCEPPPPEAARIHEVVPRFLSDKLLETNRQKNIPQLTANQ
QFLIARLIWYQDGYEQPSDEDLKRITQTWQQADDENEESDTPFRQITEMTILTVQLIVEF
AKGLPGFAKISQPDQITLLKACSSEVMMLRVARRYDAASDSILFANNQAYTRDNYRKAGM
AEVIEDLLHFCRCMYSMALDNIHYALLTAVVIFSDRPGLEQPQLVEEIQRYYLNTLRIYI
LNQLSGSARSSVIYGKILSILSELRTLGMQNSNMCISLKLKNRKLPPFLEEIWDVADMSH
TQPPPILESPTNL

SEQ ID No. 24. Simple inducible CAR comprised of one receptor component and one signalling component. The signalling component comprises an FKBP12 domain (underlined) and the CD3-Zeta endodomain (italic). A FMD-2A peptide (shown in bold) separates this signalling component from the receptor component. The receptor component comprises an anti-CD19 scFv, a HCH2CH3 spacer (highlighted in grey), a CD148 transmembrane domain and the and FKBP12 domain (underlined).

SEQ ID No. 24

<u>MGVQVETISPGDGRTFPKRGQTCVVHYTGMLEDGKKVDSSRDRNKPFKFMLGKQEVIRGW</u>
<u>EEGVAQMSVGQRAKLTISPDYAYGATGHPGIIPPHATLVFDVELLKLESGGGS</u>*ADAPAYQ*
*QGQNQLYNELNLGRREEYDVLDKRRGRDPEMGGKPRRKNPQEGLYNELQKDKMAEAYSEI*
*GMKGERRRGKHDGLYQGLSTATKDTYDALHMQALPPR*RAEGRGSLLTCGDVEENPGPME
TDTLLLWVLLLWVPGSTGDIQMTQTTSSLSASLGDRVTISGRASQDISKYLNWYQQKPDG
TVKLLIYHTSRLHSGVPSRFSGSGSGTDYSLTISNLEQEDIATYFCQQGNTLPYTFGGGT
KLEITKAGGGGSGGGGSGGGGSGGGGSEVKLQESGPGLVAPSQSLSVTCTVSGVSLPDYG
VSWIRQPPRKGLEWLGVIWGSETTYYNSALKSRLTIIKDNSKSQVFLKMNSLQTDDTAIY
YCAKHYYYGGSYAMDYWGQGTSVTVSSDPAEPKSPDKTHTCPPCPAPPVAGPSVFLFPPK
PKDTLMIARTPEVTCVVVDVSHEDPEVKFNWYVDGVEVHNAKTKPREEQYNSTYRVVSVL

-continued

TVLHQDWLNGKEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSRWQQGNVFSCS

VMHEALHNHYTQKSLSLSPGKKDPMALIVLGGVAGLLLFIGLGIFFCVRCRHRRRQAERM

AQIKRVVSEKKTAQAPHRFQKTCSPISGGGGSGVQVETISPGDGRTFPKRGQTCVVHYTG

MLEDGKKVDSSRDRNKPEKFMLGKQEVIRGWEEGVAQMSVGQRAKLTISPDYAYGATGHP

GIIPPHATLVFDVELLKLE

All publications mentioned in the above specification are herein incorporated by reference in their entirety, with special attention to the subject matter for which they are referred. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A nucleic acid comprising a nucleotide sequence encoding a chimeric antigen receptor (CAR) signalling system, said signalling system comprising;
   (i) a receptor component comprising an extracellular antigen-binding domain, a transmembrane domain and an intracellular first chemical inducer of dimerization (CID) binding domain (CBD1); and
   (ii) a plurality of soluble intracellular signalling components that localise to the cytoplasm when expressed in a cell, each intracellular signalling component comprising a T cell receptor signalling domain and a second CID binding domain (CBD2), wherein the CBD2 of each intracellular signalling component recognises the same CID but the T cell receptor signalling domains comprise different endodomains;
   wherein the nucleic acid sequence encodes a polypeptide that comprises the receptor component and the intracellular signalling components, joined by cleavage sites;
   wherein CBD1 and CBD2 are capable of simultaneously binding to a CID; wherein, in the absence of CID, binding of the antigen-binding domain to antigen does not result in signalling through the T cell receptor signalling domain; whereas, in the presence of CID, the receptor component and the intracellular signalling component heterodimerize and binding of the antigen-binding domain to antigen results in T cell receptor signalling through the T cell receptor signalling domain.

2. The nucleic acid according to claim 1, wherein the encoded receptor component and intracellular signalling components are joined by self-cleaving peptides which are cleaved between the receptor component and the intracellular signalling components after translation.

3. A vector comprising a nucleic acid according to claim 2.

4. A T cell or NK cell which comprises the nucleic acid according to claim 2, or which comprises a vector that comprises said nucleic acid.

5. A pharmaceutical composition comprising a plurality of T cells or NK cells according to claim 4.

6. A method for treating and/or preventing a disease, which comprises the step of administering a pharmaceutical composition according to claim 5 to a subject.

7. A method according to claim 6, which comprises the following steps:
(i) isolating a T cell or NK containing sample from a subject;
(ii) transducing or transfecting the T or NK cells with a nucleic acid sequence according to claim 2 or a vector comprising the nucleic acid sequence and
(iii) administering the T cells or NK cells from (ii) to the subject.

8. A method according to claim 6, which further comprises the step of administering to the subject the CID to which the CBD1 and CBD2 are capable of simultaneously binding.

9. A method for treating and/or preventing a disease in a subject which subject comprises T cells or NK cells according to claim 4, which comprises the step of administering the CID to which the CBD1 and CBD2 are capable of simultaneously binding.

10. A method according to claim 9, which involves monitoring the progression of disease and/or monitoring toxic activity in the subject and adjusting the dose of the CID to provide acceptable levels of disease progression and/or toxic activity.

11. A method according to claim 6, wherein the disease is a cancer.

12. A kit which comprises a nucleic acid according to claim 2 or a vector comprising the nucleic acid, and the CID to which the CBD1 and CBD2 are capable of simultaneously binding.

13. A kit which comprises a T or NK cell according to claim 4 and the CID to which the CBD1 and CBD2 are capable of simultaneously binding.

14. A method for making a T or NK cell that comprises a chimeric antigen receptor (CAR) signalling system, which comprises the step of introducing: a nucleic acid according to claim 2, or a vector comprising the nucleic acid, into a T cell or NK cell.

15. A method according to claim 14, wherein the T or NK cell is from a sample isolated from a subject.

16. A method for activating a CAR signalling system, in a subject comprising a T or NK cell according to claim 4, which method comprises the step of administering the CID to the subject.

17. A method for reducing the activity of a CAR signalling system, in a subject comprising a T or NK cell according to claim 4, which method comprises reducing or stopping administration of the CID to the subject.

18. A method for inducing dimerization in vivo between a receptor component and an intracellular signalling component in a subject comprising a T or NK cell according to claim 4, which comprises the step of administering a chemical inducer of dimerization (CID) to the subject.

19. A vector comprising a nucleic acid according to claim 1.

20. A T cell or NK cell which comprises the vector according to claim 19.

21. A T cell or NK cell that expresses a chimeric antigen receptor (CAR) signalling system, said signalling system comprising;
(i) a receptor component comprising an extracellular antigen-binding domain, a transmembrane domain, and a intracellular first chemical inducer of dimerization (CID) binding domain (CBD1); and
(ii) a plurality of soluble intracellular signalling components that localise to the cytoplasm when expressed in the cell, each intracellular signalling component comprising a T cell receptor signalling domain and a second CID binding domain (CBD2);
wherein CBD1 and CBD2 are capable of simultaneously binding to a CID; wherein, in the absence of CID, binding of the antigen-binding domain to antigen does not result in signalling through the T cell receptor signalling domain; whereas, in the presence of CID, the receptor component and the intracellular signalling component heterodimerize and binding of the antigen-binding domain to antigen results in T cell receptor signalling through the T cell receptor signalling domain,
wherein the CBD2 of each of the plurality of intracellular signalling components recognises the same CID but the T cell receptor signalling domains of the plurality of intracellular signalling components comprise different endodomains.

22. A pharmaceutical composition comprising a plurality of T cells or NK cells according to claim 21.

23. The nucleic acid according to claim 1, wherein the CAR signalling system has a single receptor component.

24. The T cell or NK cell according to claim 21, wherein the CAR signalling system has a single receptor component.

* * * * *

SEQUENCE LISTING

```
<160> NUMBER OF SEQ ID NOS: 26

<210> SEQ ID NO 1
<211> LENGTH: 108
<212> TYPE: PRT
<213> ORGANISM: Artificial Sequence
<220> FEATURE:
<223> OTHER INFORMATION: Chemical inducer of dimerization (CID) binding
      domain - FKBP12 domain

<400> SEQUENCE: 1

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 2
<211> LENGTH: 100
<212> TYPE: PRT
<213> ORGANISM: Artificial Sequence
<220> FEATURE:
<223> OTHER INFORMATION: CID binding domain - wild-type FRB segment of
      mTOR

<400> SEQUENCE: 2
```

```
Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
                20                  25                  30

Glu Val Leu Glu Pro Leu His Ala Met Met Glu Arg Gly Pro Gln Thr
            35                  40                  45

Leu Lys Glu Thr Ser Phe Asn Gln Ala Tyr Gly Arg Asp Leu Met Glu
        50                  55                  60

Ala Gln Glu Trp Cys Arg Lys Tyr Met Lys Ser Gly Asn Val Lys Asp
65                  70                  75                  80

Leu Thr Gln Ala Trp Asp Leu Tyr Tyr His Val Phe Arg Arg Ile Ser
                85                  90                  95

Lys Leu Glu Ser
            100

<210> SEQ ID NO 3
<211> LENGTH: 100
<212> TYPE: PRT
<213> ORGANISM: Artificial Sequence
<220> FEATURE:
<223> OTHER INFORMATION: CID binding domain - FRB with T to L
      substitution at 2098 which allows binding to AP21967

<400> SEQUENCE: 3

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
                20                  25                  30

Glu Val Leu Glu Pro Leu His Ala Met Met Glu Arg Gly Pro Gln Thr
            35                  40                  45

Leu Lys Glu Thr Ser Phe Asn Gln Ala Tyr Gly Arg Asp Leu Met Glu
        50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
                85                  90                  95

Lys Leu Glu Ser
            100

<210> SEQ ID NO 4
<211> LENGTH: 100
<212> TYPE: PRT
<213> ORGANISM: Artificial Sequence
<220> FEATURE:
<223> OTHER INFORMATION: CID binding domain - FRB segment of mTOR

<400> SEQUENCE: 4

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
                20                  25                  30

Glu Val Leu Glu Pro Leu His Ala Met Met Glu Arg Gly Pro Gln Thr
            35                  40                  45

Leu Lys Glu Thr Ser Phe Asn Gln Ala Tyr Gly Arg Asp Leu Met Glu
        50                  55                  60

Ala Gln Glu Trp Cys Arg Lys Tyr Met Lys Ser Gly Asn Val Lys Asp
65                  70                  75                  80

Leu His Gln Ala Phe Asp Leu Tyr Tyr His Val Phe Arg Arg Ile Ser
```

Lys Leu Glu Ser
            100

<210> SEQ ID NO 5
<211> LENGTH: 100
<212> TYPE: PRT
<213> ORGANISM: Artificial Sequence
<220> FEATURE:
<223> OTHER INFORMATION: CID binding domain - FRB segment of mTOR

<400> SEQUENCE: 5

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Pro Asp
65                  70                  75                  80

Leu Thr Gln Ala Trp Asp Leu Tyr Tyr His Val Phe Arg Arg Ile Ser
                85                  90                  95

Lys Leu Glu Ser
            100

<210> SEQ ID NO 6
<211> LENGTH: 21
<212> TYPE: PRT
<213> ORGANISM: Artificial Sequence
<220> FEATURE:
<223> OTHER INFORMATION: Signal peptide

<400> SEQUENCE: 6

Met Gly Thr Ser Leu Leu Cys Trp Met Ala Leu Cys Leu Leu Gly Ala
1               5                   10                  15

Asp His Ala Asp Gly
            20

<210> SEQ ID NO 7
<211> LENGTH: 21
<212> TYPE: PRT
<213> ORGANISM: Artificial Sequence
<220> FEATURE:
<223> OTHER INFORMATION: Signal peptide

<400> SEQUENCE: 7

Met Ser Leu Pro Val Thr Ala Leu Leu Leu Pro Leu Ala Leu Leu Leu
1               5                   10                  15

His Ala Ala Arg Pro
            20

<210> SEQ ID NO 8
<211> LENGTH: 20
<212> TYPE: PRT
<213> ORGANISM: Artificial Sequence
<220> FEATURE:
<223> OTHER INFORMATION: Signal peptide

<400> SEQUENCE: 8

Met Ala Val Pro Thr Gln Val Leu Gly Leu Leu Leu Leu Trp Leu Thr

```
1               5                   10                  15
Asp Ala Arg Cys
            20

<210> SEQ ID NO 9
<211> LENGTH: 234
<212> TYPE: PRT
<213> ORGANISM: Artificial Sequence
<220> FEATURE:
<223> OTHER INFORMATION: Spacer (hinge-CH2CH3 of human IgG1)

<400> SEQUENCE: 9

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 10
<211> LENGTH: 46
<212> TYPE: PRT
<213> ORGANISM: Artificial Sequence
<220> FEATURE:
<223> OTHER INFORMATION: Spacer (human CD8 stalk)

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45
```

<210> SEQ ID NO 11
<211> LENGTH: 20
<212> TYPE: PRT
<213> ORGANISM: Artificial Sequence
<220> FEATURE:
<223> OTHER INFORMATION: Spacer (human IgG1 hinge)

<400> SEQUENCE: 11

Ala Glu Pro Lys Ser Pro Asp Lys Thr His Thr Cys Pro Pro Cys Pro
1               5                   10                  15

Lys Asp Pro Lys
            20

<210> SEQ ID NO 12
<211> LENGTH: 185
<212> TYPE: PRT
<213> ORGANISM: Artificial Sequence
<220> FEATURE:
<223> OTHER INFORMATION: Spacer (CD2 ectodomain)

<400> SEQUENCE: 12

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
                20                  25                  30

Ile Lys Trp Glu Lys Thr Ser Asp Lys Lys Lys Ile Ala Gln Phe Arg
            35                  40                  45

Lys Glu Lys Glu Thr Phe Lys Glu Lys Asp Thr Tyr Lys Leu Phe Lys
        50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
                100                 105                 110

Trp Thr Cys Ile Asn Thr Thr Leu Thr Cys Glu Val Met Asn Gly Thr
            115                 120                 125

Asp Pro Glu Leu Asn Leu Tyr Gln Asp Gly Lys His Leu Lys Leu Ser
        130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 13
<211> LENGTH: 259
<212> TYPE: PRT
<213> ORGANISM: Artificial Sequence
<220> FEATURE:
<223> OTHER INFORMATION: Spacer (CD34 ectodomain)

<400> SEQUENCE: 13

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
                20                  25                  30

Pro Ser Thr Leu Gly Ser Thr Ser Leu His Pro Val Ser Gln His Gly

```
                35                  40                  45
Asn Glu Ala Thr Thr Asn Ile Thr Glu Thr Thr Val Lys Phe Thr Ser
            50                  55                  60
Thr Ser Val Ile Thr Ser Val Tyr Gly Asn Thr Asn Ser Ser Val Gln
65                  70                  75                  80
Ser Gln Thr Ser Val Ile Ser Thr Val Phe Thr Thr Pro Ala Asn Val
                85                  90                  95
Ser Thr Pro Glu Thr Thr Leu Lys Pro Ser Leu Ser Pro Gly Asn Val
            100                 105                 110
Ser Asp Leu Ser Thr Thr Ser Thr Ser Leu Ala Thr Ser Pro Thr Lys
                115                 120                 125
Pro Tyr Thr Ser Ser Ser Pro Ile Leu Ser Asp Ile Lys Ala Glu Ile
            130                 135                 140
Lys Cys Ser Gly Ile Arg Glu Val Lys Leu Thr Gln Gly Ile Cys Leu
145                 150                 155                 160
Glu Gln Asn Lys Thr Ser Ser Cys Ala Glu Phe Lys Lys Asp Arg Gly
                165                 170                 175
Glu Gly Leu Ala Arg Val Leu Cys Gly Glu Glu Gln Ala Asp Ala Asp
            180                 185                 190
Ala Gly Ala Gln Val Cys Ser Leu Leu Leu Ala Gln Ser Glu Val Arg
                195                 200                 205
Pro Gln Cys Leu Leu Leu Val Leu Ala Asn Arg Thr Glu Ile Ser Ser
            210                 215                 220
Lys Leu Gln Leu Met Lys Lys His Gln Ser Asp Leu Lys Lys Leu Gly
225                 230                 235                 240
Ile Leu Asp Phe Thr Glu Gln Asp Val Ala Ser His Gln Ser Tyr Ser
                245                 250                 255
Gln Lys Thr

<210> SEQ ID NO 14
<211> LENGTH: 112
<212> TYPE: PRT
<213> ORGANISM: Artificial Sequence
<220> FEATURE:
<223> OTHER INFORMATION: Signalling component CD3 Z endodomain

<400> SEQUENCE: 14

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
                35                  40                  45
Pro Arg Arg Lys Asn Pro Gln Glu Gly Leu Tyr Asn Glu Leu Gln Lys
            50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 15
<211> LENGTH: 152
<212> TYPE: PRT
<213> ORGANISM: Artificial Sequence
```

```
<220> FEATURE:
<223> OTHER INFORMATION: Signalling component CD28 and CD3 Zeta
      endodomains

<400> SEQUENCE: 15

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65              70                  75                  80

Arg Asp Pro Glu Met Gly Gly Lys Pro Arg Arg Lys Asn Pro Gln Glu
            85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
        115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150

<210> SEQ ID NO 16
<211> LENGTH: 188
<212> TYPE: PRT
<213> ORGANISM: Artificial Sequence
<220> FEATURE:
<223> OTHER INFORMATION: Signalling component CD28, OX40 and CD3 Zeta
      endodomains

<400> SEQUENCE: 16

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
        35                  40                  45

Ala His Lys Pro Pro Gly Gly Gly Ser Phe Arg Thr Pro Ile Gln Glu
    50                  55                  60

Glu Gln Ala Asp Ala His Ser Thr Leu Ala Lys Ile Arg Val Lys Phe
65              70                  75                  80

Ser Arg Ser Ala Asp Ala Pro Ala Tyr Gln Gln Gly Gln Asn Gln Leu
            85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
        115                 120                 125

Asn Pro Gln Glu Gly Leu Tyr Asn Glu Leu Gln Lys Asp Lys Met Ala
    130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175
```

Tyr Asp Ala Leu His Met Gln Ala Leu Pro Pro Arg
            180                 185

<210> SEQ ID NO 17
<211> LENGTH: 20
<212> TYPE: PRT
<213> ORGANISM: Foot-and-mouth disease virus

<400> SEQUENCE: 17

Arg Ala Glu Gly Arg Gly Ser Leu Leu Thr Cys Gly Asp Val Glu Glu
1               5                   10                  15

Asn Pro Gly Pro
            20

<210> SEQ ID NO 18
<211> LENGTH: 20
<212> TYPE: PRT
<213> ORGANISM: Foot-and-mouth disease virus

<400> SEQUENCE: 18

Gln Cys Thr Asn Tyr Ala Leu Leu Lys Leu Ala Gly Asp Val Glu Ser
1               5                   10                  15

Asn Pro Gly Pro
            20

<210> SEQ ID NO 19
<211> LENGTH: 3549
<212> TYPE: DNA
<213> ORGANISM: Artificial Sequence
<220> FEATURE:
<223> OTHER INFORMATION: Simple inducible Chimeric Antigen Receptor
      (CAR)

<400> SEQUENCE: 19
atggagaccg acaccctgct gctgtgggtg ctgctgctgt gggtgccagg cagcaccggc      60
gacatccaga tgacccagac caccagcagc ctgagcgcca gcctgggcga ccgggtgacc     120
atcagctgca gagccagcca ggacatcagc aagtacctga actggtacca gcagaagccc     180
gacggcaccg tgaagctgct gatctaccac accagccggc tgcacagcgg cgtgcccagc     240
cggttcagcg gcagcggcag cggcaccgac tacagcctga ccatcagcaa cctggagcag     300
gaggacatcg ccacctactt ctgccagcag ggcaacaccc tgccctacac cttcggaggc     360
ggcaccaagc tggagatcac caaggccgga ggcggaggct ctggcggagg cggctctggc     420
ggaggcggct ctggcggagg cggcagcgag gtgaagctgc aggagtctgg cccaggcctg     480
gtggccccaa gccagagcct gagcgtgacc tgcaccgtga gcggcgtgag cctgcccgac     540
tacggcgtga gctggatcag gcagccccca cggaagggcc tggagtggct gggcgtgatc     600
tggggcagcg agaccaccta ctacaacagc gccctgaaga gccggctgac catcatcaag     660
gacaacagca gagcccaggt gttcctgaag atgaacagcc tgcagaccga cacccgcc     720 atctactact gcgccaagca ctactactat ggcggcagct acgctatgga ctactgggc     780 cagggcacca gcgtgaccgt gagctcggat cccgccgagc ccaaatctcc tgacaaaact     840
cacacatgcc cacgtgccc agcacctccc gtggccggc cgtcagtctt cctcttcccc     900
ccaaaaccca aggacaccct catgatcgcc ggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080

```
gtcctcaccg tcctgcacca ggactggctg aatggcaagg agtacaagtg caaggtctcc    1140
aacaaagccc tcccagcccc catcgagaaa accatctcca aagccaaagg gcagccccga    1200
gaaccacagg tgtacaccct gccccatcc cgggatgagc tgaccaagaa ccaggtcagc     1260
ctgacctgcc tggtcaaagg cttctatccc agcgacatcg ccgtggagtg ggagagcaat    1320
gggcaaccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc cctgcacaat cactataccc agaaatctct gagtctgagc    1500
ccaggcaaga aggaccccaa gttctgggtc ctggtggtgg tgggaggcgt gctggcctgt    1560
tactctctcc tggtgaccgt ggccttcatc atcttctggg tgggagtgca ggtggaaacc    1620
atctccccag agacgggcg caccttcccc aagcgcggcc agacctgcgt ggtgcactac    1680
accgggatgc ttgaagatgg aaagaaattc gattcctccc gggacagaaa caagcccttt    1740
aagtttatgc taggcaagca ggaggtgatc cgaggctggg aagaagggtg tgcccagatg    1800
agtgtgggtc agagagccaa actgactata tctccagatt atgcctatgg tgccactggg    1860
cacccaggca tcatcccacc acatgccact ctcgtcttcg atgtggagct tctaaaactg    1920
gaacgcgcag agggccgggg ctcattgctg acctgtggag atgtcgagga aaatcccggc    1980
ccaatggctt ctagaatcct ctggcatgag atgtggcatg aaggcctgga agaggcatct    2040
cgtttgtact ttggggaaag gaacgtgaaa ggcatgtttg aggtgctgga gcccttgcat    2100
gctatgatgg aacggggccc ccagactctg aaggaaacat cctttaatca ggcctatggt    2160
cgagatttaa tggaggccca agagtggtgc aggaagtaca tgaaatcagg gaatgtcaag    2220
gacctcctcc aagcctggga cctctattat catgtgttcc gacgaatctc aaagctcgag    2280
agtggcggag gaggcagttc aaggtccgcc gacgcgcctg cataccagca ggggcagaat    2340
cagctgtaca acgagctcaa cctcggtagg cgcgaggaat cgatgtgct cgataagaga     2400
agaggtcgcg atcccgagat gggaggaaaa cctcagcgcc gcaagaaccc tcaggagggg    2460
ctgtataacg aactgcagaa ggataagatg gcagaggcct actccgagat tggcatgaag    2520
ggtgagagga gaagaggtaa aggccatgac ggcctctacc aaggcctctc taccgcaacg    2580
aaagacactt atgacgctct gcatatgcag gctctcccc ctaggcagtg cactaattac     2640
gcccttctga aacttgccgg cgatgtggag tctaaccctg ccctatcct gtggcacgag     2700
atgtggcatg agggtctgga agaggccagc cggctgtact tcggagagag aaatgttaag    2760
ggtatgttcg aggtgctgga gccgcttcac gctatgatgg agaggggccc ccagacccta    2820
aaagaaacca gcttcaatca agcctacggg agggatctta tggaggcaca ggaatggtgt    2880
cggaagtaca tgaagagcgg gaacgtcaag gacctgctcc aggcttggga tttgtattat    2940
cacgtcttta ggcggatcag caagtctgga ggcggaggaa gtctgcacag cgattacatg    3000
aacatgaccc cccgaaggcc cggacccaca cgcaaacact atcaacccta tgctccccca    3060
cgcgacttcg ccgcctaccg gtcacgcgcc gagggggcg gctctttgtt gacttgcggg     3120
gacgttgaag agaatcctgg ccccatcctt tggcacgaga tgtggcacga gggcctggag    3180
gaagcctccc ggctgtattt cggagagcgc aacgtcaaag gaatgtttga ggtgctggag    3240
cctctccatg caatgatgga gaggggggcct cagactctta aagaaacatc ctttaatcag   3300
gcttacggta gagatttgat ggaggctcaa gaatggtgcc ggaaatacat gaagagtgga    3360
aacgttaaag acctgctgca ggcatgggac ctgtactatc acgtattcag acggatctca    3420
aagtcagggg gcggtggctc cctttatatc ttcaagcagc ctttcatgag gccggtgcag    3480
```

```
accacacaag aagaggatgg gtgctcttgc cggttccccg aggaggagga gggcggatgc      3540
gagctctga                                                             3549

<210> SEQ ID NO 20
<211> LENGTH: 4266
<212> TYPE: DNA
<213> ORGANISM: Artificial Sequence
<220> FEATURE:
<223> OTHER INFORMATION: Inducible CAR

<400> SEQUENCE: 20
atgagcctgc ccgtgaccgc cctgctgctg cccctggccc tgctgctgca cgccgccaga        60
ccagacatcc agatgaccca gaccaccagc agcctgagcg ccagcctggg cgaccgggtg       120
accatcagct gcagagccag ccaggacatc agcaagtacc tgaactggta ccagcagaag       180
cccgacggca ccgtgaagct gctgatctac cacaccagcc ggctgcacag cggcgtgccc       240
agccggttca gcggcagcgg cagcggcacc gactacagcc tgaccatcag caacctggag       300
caggaggaca tcgccaccta cttctgccag cagggcaaca ccctgcccta caccttcgga       360
ggcggcacca agctggagat caccaaggcc ggaggcggag gctctggcgg aggcggctct       420
ggcggaggcg gctctggcgg aggcggcagc gaggtgaagc tgcaggagtc tggcccaggc       480
ctggtggccc caagccagag cctgagcgtg acctgcaccg tgagcggcgt gagcctgccc       540
gactacggcg tgagctggat caggcagccc ccacggaagg gcctggagtg gctgggcgtg       600
atctggggca gcgagaccac ctactacaac agcgccctga agagccggct gaccatcatc       660
aaggacaaca gcaagagcca ggtgttcctg aagatgaaca gcctgcagac cgacgacacc       720
gccatctact actgcgccaa gcactactac tatggcggca gctacgctat ggactactgg       780
ggccagggca ccagcgtgac cgtgagctca gatcccacca cgacgccagc gccgcgacca       840
ccaacaccgg cgcccaccat cgcgtcgcag cccctgtccc tgcgcccaga ggcgtgccgg       900
ccagcggcgg ggggcgcagt gcacacgagg gggctggact tcgcctgtga tatcttttgg       960
gtgctggtgg tggttggtgg agtcctggct tgctatagct tgctagtaac agtggccttc      1020
atcatcttct gggtgggagt gcaggtggaa accatctccc caggagacgg cgcgccttc       1080 cccaagcgcg gccagacctg cgtggtgcac tacaccggga tgcttgaaga tggaaagaaa      1140
ttcgattcct cccgggacag aaacaagccc tttaagttta tgctaggcaa gcaggaggtg      1200
atccgaggct gggaagaagg ggttgcccag atgagtgtgg gtcagagagc caaactgact      1260
atatctccag attatgccta tggtgccact gggcacccag gcatcatccc accacatgcc      1320
actctcgtct tcgatgtgga gcttctaaaa ctggaacgag ccgagggcag gggaagtctt      1380
ctaacatgcg gggacgtgga ggaaaatccc gggcccatgg agaccgacac cctgctgctg      1440
tgggtgctgc tgctgtgggt gccggcagc accggccagg tgcagctgca gcagcccggc      1500
gccgagctgg tgaagcccgg cgccagcgtg aagatgagct gcaaggccag cggctacacc      1560
ttcaccagct acaacatgca ctgggtgaag cagacccccg gccgggcct ggagtggatc      1620 ggcgccatct accccggcaa cggcgacacc agctacaacc agaagttcaa gggcaaggcc      1680
accctgaccg ccgacaagag cagcagcacc gcctacatgc agctgagcag cctgaccagc      1740
gaggacagcg ccgtgtacta ctgcgcccgg agcacctact acggcggcga ctggtacttc      1800
aacgtgtggg gcgccggcac caccgtgacc gtgagcggag cggcggcag cggaggaggc      1860 ggctctgggg gaggcggatc tcagatcgtg ctgagccaga gccccgccat cctgagcgcc      1920
```

```
agccccggcg agaaggtgac catgacctgc cgggccagca gcagcgtgag ctacatccac      1980
tggttccagc agaagcccgg cagcagcccc aagccctgga tctacgccac cagcaacctg      2040
gccagcggcg tgcccgtgcg gttcagcggc agcggcagcg gcaccagcta cagcctgacc      2100
atcagccggt ggaggccga ggacgccgcc acctactact gccagcagtg gaccagcaac       2160
ccacccacct tcggcggcgg caccaagctg gagatcaagc ggtcggatcc cgccgagccc      2220
aaatctcctg acaaaactca cacatgccca ccgtgcccag cacctcccgt ggccggcccg      2280
tcagtcttcc tcttcccccc aaaacccaag gacaccctca tgatcgcccg gacccctgag      2340
gtcacatgcg tggtggtgga cgtgagccac gaagaccctg aggtcaagtt caactggtac      2400
gtggacggcg tggaggtgca taatgccaag acaaagccgc gggaggagca gtacaacagc      2460
acgtaccgtg tggtcagcgt cctcaccgtc ctgcaccagg actggctgaa tggcaaggag      2520
tacaagtgca aggtctccaa caaagccctc ccagccccca tcgagaaaac catctccaaa      2580
gccaaagggc agccccgaga accacaggtg tacaccctgc ccccatcccg ggatgagctg      2640
accaagaacc aggtcagcct gacctgcctg gtcaaaggct tctatcccag cgacatcgcc      2700
gtggagtggg agagcaatgg gcaaccggag aacaactaca agaccacgcc tcccgtgctg      2760
gactccgacg gctccttctt cctctacagc aagctcaccg tggacaagag caggtggcag      2820
caggggaacg tcttctcatg ctccgtgatg catgaggccc tgcacaatca ctatacccag      2880
aaatctctga gtctgagccc aggcaagaag gaccccaagt ctgggtcct ggtggtggtg       2940
ggaggcgtgc tggcctgtta ctctctcctg gtgaccgtgg ccttcatcat cttctgggtg      3000
ggagtgcagg tggaaaccat ctccccagga gacgggcgca ccttcccaa gcgcggccag       3060
acctgcgtgg tgcactacac cgggatgctt gaagatggaa agaaattcga ttcctcccgg      3120
gacagaaaca gcccctttaa gtttatgcta ggcaagcagg aggtgatccg aggctgggaa      3180
gaaggggttg cccagatgag tgtgggtcag agagccaaac tgactatatc tccagattat      3240
gcctatggtg ccactgggca cccaggcatc atcccaccac atgccactct cgtcttcgat      3300
gtggagcttc taaaactgga acgcgcagag gccggggct cattgctgac ctgtggagat       3360
gtcgaggaaa atcccggccc aatggcttct agaatcctct ggcatgagat gtggcatgaa      3420
ggcctggaag aggcatctcg tttgtacttt ggggaaagga acgtgaaagg catgtttgag      3480
gtgctggagc ccttgcatgc tatgatggaa cggggccccc agactctgaa ggaaacatcc      3540
tttaatcagg cctatggtcg agatttaatg gaggcccaag agtggtgcag gaagtacatg      3600
aaatcaggga atgtcaagga cctcctccaa gcctgggacc tctattatca tgtgttccga      3660
cgaatctcaa agctcgagta tagcggcggc ggcagcagga gtaagaggag caggctcctg      3720
cacagtgact acatgaacat gactcccgc cgccccgggc ccacccgcaa gcattaccag       3780
ccctatgccc caccacgcga cttcgcagcc tatcgctcca gggaccagag gctgcccccc      3840
gatgccaca gcccctgg gggaggcagt ttccggaccc ccatccaaga ggagcaggcc         3900
gacgcccact ccaccctggc caagatcaga gtgaagttca gcaggagcgc agacgccccc      3960
gcgtaccagc agggccagaa ccagctctat aacgagctca atctaggacg aagagaggag      4020
tacgatgttt tggacaagag acgtggccgg gaccctgaga tgggggaaa gccgagaagg       4080
aagaaccctc aggaaggcct gtacaatgaa ctgcagaaag ataagatggc ggaggcctac      4140
agtgagattg ggatgaaagg cgagcgccgg aggggcaagg ggcacgatgg cctttaccag      4200
ggtctcagta cagccaccaa ggacacctac gacgcccttc acatgcaggc cctgcctcct      4260
cgctaa                                                                4266
```

<210> SEQ ID NO 21
<211> LENGTH: 3549
<212> TYPE: DNA
<213> ORGANISM: Artificial Sequence
<220> FEATURE:
<223> OTHER INFORMATION: Inducible CAR

<400> SEQUENCE: 21

```
atggagaccg acaccctgct gctgtgggtg ctgctgctgt gggtgccagg cagcaccggc    60
gacatccaga tgacccagac caccagcagc ctgagcgcca gcctgggcga ccgggtgacc   120
atcagctgca gagccagcca ggacatcagc aagtacctga actggtacca gcagaagccc   180
gacggcaccg tgaagctgct gatctaccac accagccggc tgcacagcgg cgtgcccagc   240
cggttcagcg gcagcggcag cggcaccgac tacagcctga ccatcagcaa cctggagcag   300
gaggacatcg ccacctactt ctgccagcag ggcaacaccc tgccctacac cttcggaggc   360
ggcaccaagc tggagatcac caaggccgga ggcggaggct ctggcggagg cggctctggc   420
ggaggcggct ctggcggagg cggcagcgag gtgaagctgc aggagtctgg cccaggcctg   480
gtggccccaa gccagagcct gagcgtgacc tgcaccgtga cggcgtgag cctgcccgac   540
tacggcgtga gctggatcag gcagccccca cggaagggcc tggagtggct gggcgtgatc   600
tggggcagcg agaccaccta ctacaacagc gccctgaaga ccggctgac catcatcaag   660
gacaacagca agagccaggt gttcctgaag atgaacagcc tgcagaccga cgacaccgcc   720
atctactact gcgccaagca ctactactat ggcggcagct acgctatgga ctactggggc   780
cagggcacca gcgtgaccgt gagctcggat cccgccgagc ccaaatctcc tgacaaaact   840
cacacatgcc caccgtgccc agcacctccc gtggccggcc cgtcagtctt cctcttcccc   900
ccaaaaccca aggacaccct catgatcgcc cggacccctg aggtcacatg cgtggtggtg   960
gacgtgagcc acgaagaccc tgaggtcaag ttcaactggt acgtggacgg cgtggaggtg  1020
cataatgcca agacaaagcc gcgggaggag cagtacaaca gcacgtaccg tgtggtcagc  1080
gtcctcaccg tcctgcacca ggactggctg aatggcaagg agtacaagtg caaggtctcc  1140
aacaaagccc tcccagcccc catcgagaaa accatctcca agccaaagg cagccccga  1200
gaaccacagg tgtacaccct gcccccatcc cgggatgagc tgaccaagaa ccaggtcagc  1260
ctgacctgcc tggtcaaagg cttctatccc agcgacatcg ccgtggagtg ggagagcaat  1320
gggcaaccgg agaacaacta caagaccacg cctcccgtgc tggactccga cggctccttc  1380
ttcctctaca gcaagctcac cgtggacaag agcaggtggc agcaggggaa cgtcttctca  1440
tgctccgtga tgcatgaggc cctgcacaat cactataccc agaaatctct gagtctgagc  1500
ccaggcaaga aggaccccaa gttctgggtc ctggtggtgg tgggaggcgt gctggcctgt  1560
tactctctcc tggtgaccgt ggccttcatc atcttctggg tgggagtgca ggtggaaacc  1620
atctccccag agacgggcg caccttcccc aagcgcggcc agacctgcgt ggtgcactac  1680
accgggatgc ttgaagatgg aaagaaattc gattcctccc gggacagaaa caagcccttt  1740
aagtttatgc taggcaagca ggaggtgatc cgaggctggg aagaagggt tgcccagatg  1800
agtgtgggtc agagagccaa actgactata tctccagatt atgcctatgg tgccactggg  1860
cacccaggca tcatcccacc acatgccact ctcgtcttcg atgtggagct tctaaaactg  1920
gaacgcgcag agggccgggg ctcattgctg acctgtggag atgtcgagga aatcccggc  1980
ccaatggctt ctagaatcct ctggcatgag atgtggcatg aaggcctgga agaggcatct  2040
```

| | |
|---|---:|
| cgtttgtact ttggggaaag gaacgtgaaa ggcatgtttg aggtgctgga gcccttgcat | 2100 |
| gctatgatgg aacggggccc ccagactctg aaggaaacat cctttaatca ggcctatggt | 2160 |
| cgagatttaa tggaggccca agagtggtgc aggaagtaca tgaaatcagg gaatgtcaag | 2220 |
| gacctcctcc aagcctggga cctctattat catgtgttcc gacgaatctc aaagctcgag | 2280 |
| agtggcggag gaggcagttc aaggtccgcc gacgcgcctg cataccagca ggggcagaat | 2340 |
| cagctgtaca acgagctcaa cctcggtagg cgcgaggaat acgatgtgct cgataagaga | 2400 |
| agaggtcgcg atcccgagat gggaggaaaa cctcagcgcc gcaagaaccc tcaggagggg | 2460 |
| ctgtataacg aactgcagaa ggataagatg gcagaggcct actccgagat tggcatgaag | 2520 |
| ggtgagagga gaagaggtaa aggccatgac ggcctctacc aaggcctctc taccgcaacg | 2580 |
| aaagacactt atgacgctct gcatatgcag gctctccccc ctaggcagtg cactaattac | 2640 |
| gcccttctga aacttgccgg cgatgtggag tctaaccctg gccctatcct gtggcacgag | 2700 |
| atgtggcatg agggtctgga agaggccagc cggctgtact tcggagagag aaatgttaag | 2760 |
| ggtatgttcg aggtgctgga gccgcttcac gctatgatgg agaggggccc ccagaccctc | 2820 |
| aaagaaacca gcttcaatca agcctacggg aaggatctta tggaggcaca ggaatggtgt | 2880 |
| cggaagtaca tgaagagcgg gaacgtcaag gacctgctcc aggcttggga tttgtattat | 2940 |
| cacgtcttta gcggatcag caagtctgga ggcggaggaa gtctgcacag cgattacatg | 3000 |
| aacatgaccc cccgaaggcc cggacccaca cgcaaacact atcaaccta tgctccccca | 3060 |
| cgcgacttcg ccgcctaccg gtcacgcgcc gaggggcgcg gctctttgtt gacttgcggg | 3120 |
| gacgttgaag agaatcctgg ccccatcctt tggcacgaga tgtggcacga gggcctggag | 3180 |
| gaagcctccc ggctgtattt cggagagcgc aacgtcaaag gaatgtttga ggtgctggag | 3240 |
| cctctccatg caatgatgga gagggggcct cagactctta agaaacatc ctttaatcag | 3300 |
| gcttacggta gagatttgat ggaggctcaa gaatggtgcc ggaaatacat gaagagtgga | 3360 |
| aacgttaaag acctgctgca ggcatgggac ctgtactatc acgtattcag acggatctca | 3420 |
| aagtcagggg gcggtggctc cctttatatc ttcaagcagc ctttcatgag gccggtgcag | 3480 |
| accacacaag aagaggatgg ggtgctcttgc cggttccccg aggaggagga gggcggatgc | 3540 |
| gagctctga | 3549 |

<210> SEQ ID NO 22
<211> LENGTH: 3993
<212> TYPE: DNA
<213> ORGANISM: Artificial Sequence
<220> FEATURE:
<223> OTHER INFORMATION: Inducible CAR

<400> SEQUENCE: 22

| | |
|---|---:|
| atggagaccg acaccctgct gctgtgggtg ctgctgctgt gggtgccagg cagcaccggc | 60 |
| gacatccaga tgacccagac caccagcagc ctgagcgcca gcctgggcga ccgggtgacc | 120 |
| atcagctgca gagccagcca ggacatcagc aagtacctga actggtacca gcagaagccc | 180 |
| gacggcaccg tgaagctgct gatctaccac accagccgcg tgcacagcgg cgtgcccagc | 240 |
| cggttcagcg gcagcggcag cggcaccgac tacagcctga ccatcagcaa cctggagcag | 300 |
| gaggacatcg ccacctactt ctgccagcag ggcaacaccc tgccctacac cttcggaggc | 360 |
| ggcaccaagc tggagatcac caaggccgga ggcggaggct ctggcggagg cggctctggc | 420 |
| ggaggcggct ctggcggagg cggcagcgag gtgaagctgc aggagtctgg cccaggcctg | 480 |
| gtggccccaa gccagagcct gagcgtgacc tgcaccgtga gcggcgtgag cctgcccgac | 540 |

```
tacggcgtga gctggatcag gcagccccca cggaagggcc tggagtggct gggcgtgatc      600
tggggcagcg agaccaccta ctacaacagc gccctgaaga gccggctgac catcatcaag      660
gacaacagca agagccaggt gttcctgaag atgaacagcc tgcagaccga cgacaccgcc      720
atctactact gcgccaagca ctactactat ggcggcagct acgctatgga ctactggggc      780
cagggcacca gcgtgaccgt gagctcggat cccgccgagc ccaaatctcc tgacaaaact      840
cacacatgcc caccgtgccc agcacctccc gtggccggcc cgtcagtctt cctcttcccc      900
ccaaaaccca aggacaccct catgatcgcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg agtacaagtg caaggtctcc     1140
aacaaagccc tcccagcccc catcgagaaa accatctcca aagccaaagg gcagcccga     1200 gaaccacagg tgtacaccct gcccccatcc cgggatgagc tgaccaagaa ccaggtcagc     1260
ctgacctgcc tggtcaaagg cttctatccc agcgacatcg ccgtggagtg ggagagcaat     1320
gggcaaccgg agaacaacta caagaccacg cctcccgtgc tggactccga cggctccttc     1380
ttcctctaca gcaagctcac cgtggacaag agcaggtggc agcaggggaa cgtcttctca     1440
tgctccgtga tgcatgaggc cctgcacaat cactataccc agaaatctct gagtctgagc     1500
ccaggcaaga aggacccca gttctgggtc ctggtggtgg tgggaggcgt gctggcctgt     1560
tactctctcc tggtgaccgt ggccttcatc atcttctggg tgatcctctg gcatgagatg     1620
tggcatgaag gcctggaaga ggcatctcgt ttgtactttg gggaaaggaa cgtgaaaggc     1680
atgtttgagg tgctggagcc cttgcatgct atgatggaac gggcccccca gactctgaag     1740
gaaacatcct ttaatcaggc ctatggtcga gatttaatgg aggcccaaga gtggtgcagg     1800
aagtacatga aatcagggaa tgtcaaggac ctcctccaag cctggacct ctattatcat     1860 gtgttccgac gaatctcaaa gagcagcctg gtgggaccca cccagagctt cttcatgcgg     1920
gagagcaaga ccctgggagc cgtgcagatc atgaacggcc tgttccacat cgccctggga     1980
ggcctgctga tgatccctgc cggcatctac gccccaatct gcgtgaccgt gtggtaccca     2040
ctgtggggag gcatcatgta catcatcagc ggcagcctgc tggccgccac cgagaagaac     2100
agcggagggg gaagcatcct gtggcacgag atgtggcatg agggtctgga agaggccagc     2160
cggctgtact tcggagagag aaatgttaag ggtatgttcg aggtgctgga gccgcttcac     2220
gctatgatgg agaggggccc ccagaccctc aaagaaacca gcttcaatca gcctacgggg     2280
agggatctta tggaggcaca ggaatggtgt cggaagtaca tgaagagcgg aacgtcaag     2340 gacctgctcc aggcttggga tttgtattat cacgtcttta gcggatcag caagtctgga     2400 ggcggaggaa gtcggaagtg cctggtgaag ggcaagatga tcatgaacag cctgagcctg     2460
ttcgccgcca tcagcggcat gatcctgagc atcatggaca tcctgaacat caagatcagc     2520
cacttcctga agatggagag cctgaacttc atccgggccc acacccccata catcaacatc     2580 tacaactgcg agcctgccaa ccccagcgag aagaacagcc ccagcaccca gtactgctac     2640
agcatccaga gcctgttcct gggcatcctg agcgtgatgc tgatcttcgc cttcttccag     2700
gagctggtga tcgccggcat cgtggagaac gagtggaagc ggacctgcag ccggcccaag     2760
agcatcctgt ggcacgagat gtggcatgag ggtctggaag aggccagccg gctgtacttc     2820
ggagagagaa atgttaaggg tatgttcgag gtgctggagc cgcttcacgc tatgatggag     2880
```

```
aggggcccccc agaccctcaa agaaaccagc ttcaatcaag cctacgggag ggatcttatg    2940
gaggcacagg aatggtgtcg gaagtacatg aagagcggga acgtcaagga cctgctccag    3000
gcttgggatt tgtattatca cgtctttagg cggatcagca agcgcgcaga gggccggggc    3060
tcattgctga cctgtggaga tgtcgaggaa atcccggcc caggagtgca ggtgaaaacc     3120
atctccccag gagacgggcg caccttcccc aagcgcggcc agacctgcgt ggtgcactac    3180
accgggatgc ttgaagatgg aaagaaattc gattcctccc gggacagaaa caagcccttt    3240
aagtttatgc taggcaagca ggaggtgatc cgaggctggg aagaaggggt tgcccagatg    3300
agtgtgggtc agagagccaa actgactata tctccagatt atgcctatgg tgccactggg    3360
cacccaggca tcatcccacc acatgccact ctcgtcttcg atgtggagct tctaaaactg    3420
gaaaggagta agaggagcag gctcctgcac agtgactaca tgaacatgac tccccgccgc    3480
cccgggccca cccgcaagca ttaccagccc tatgccccac cacgcgactt cgcagcctat    3540
cgctccaggg accagaggct gcccccgat gcccacaagc ccctggggg aggcagtttc      3600 cggaccccca tccaagagga gcaggccgac gcccactcca ccctggccaa gatcagagtg    3660
aagttcagca ggagcgcaga cgcccccgcg taccagcagg gccagaacca gctctataac    3720
gagctcaatc taggacgaag agaggagtac gatgttttgg acaagagacg tggccgggac    3780
cctgagatgg ggggaaagcc gagaaggaag aaccctcagg aaggcctgta caatgaactg    3840
cagaaagata gatgcggaa ggcctacagt gagattggga tgaaaggcga gcgccggagg    3900 ggcaagggc acgatggcct ttaccagggt ctcagtacag ccaccaagga cacctacgac    3960
gcccttcaca tgcaggccct gcctcctcgc tga                                 3993
```

<210> SEQ ID NO 23
<211> LENGTH: 1273
<212> TYPE: PRT
<213> ORGANISM: Artificial Sequence
<220> FEATURE:
<223> OTHER INFORMATION: Simple inducible CAR

<400> SEQUENCE: 23

```
Met Pro Val Asp Arg Ile Leu Glu Ala Glu Leu Ala Val Glu Gln Lys
1               5                   10                  15

Ser Asp Gln Gly Val Glu Gly Pro Gly Gly Thr Gly Gly Ser Gly Ser
                20                  25                  30

Ser Pro Asn Asp Pro Val Thr Asn Ile Cys Gln Ala Ala Asp Lys Gln
            35                  40                  45

Leu Phe Thr Leu Val Glu Trp Ala Lys Arg Ile Pro His Phe Ser Ser
        50                  55                  60

Leu Pro Leu Asp Asp Gln Val Ile Leu Leu Arg Ala Gly Trp Asn Glu
65                  70                  75                  80

Leu Leu Ile Ala Ser Phe Ser His Arg Ser Ile Asp Val Arg Asp Gly
                85                  90                  95

Ile Leu Leu Ala Thr Gly Leu His Val His Arg Asn Ser Ala His Ser
            100                 105                 110

Ala Gly Val Gly Ala Ile Phe Asp Arg Val Leu Thr Glu Leu Val Ser
        115                 120                 125

Lys Met Arg Asp Met Arg Met Asp Lys Thr Glu Leu Gly Cys Leu Arg
    130                 135                 140

Ala Ile Ile Leu Phe Asn Pro Glu Val Arg Gly Leu Lys Ser Ala Gln
145                 150                 155                 160

Glu Val Glu Leu Leu Arg Glu Lys Val Tyr Ala Ala Leu Glu Glu Tyr
```

```
                    165                 170                 175
Thr Arg Thr Thr His Pro Asp Glu Pro Gly Arg Phe Ala Lys Leu Leu
                180                 185                 190

Leu Arg Leu Pro Ser Leu Arg Ser Ile Gly Leu Lys Cys Leu Glu His
            195                 200                 205

Leu Phe Phe Arg Leu Ile Gly Asp Val Pro Ile Asp Thr Phe Leu
    210                 215                 220

Met Glu Met Leu Glu Ser Pro Ser Asp Ser Gly Gly Ser Ala
225                 230                 235                 240

Asp Ala Pro Ala Tyr Gln Gln Gly Gln Asn Gln Leu Tyr Asn Glu Leu
                245                 250                 255

Asn Leu Gly Arg Arg Glu Glu Tyr Asp Val Leu Asp Lys Arg Arg Gly
                260                 265                 270

Arg Asp Pro Glu Met Gly Gly Lys Pro Arg Arg Lys Asn Pro Gln Glu
                275                 280                 285

Gly Leu Tyr Asn Glu Leu Gln Lys Asp Lys Met Ala Glu Ala Tyr Ser
            290                 295                 300

Glu Ile Gly Met Lys Gly Glu Arg Arg Arg Gly Lys Gly His Asp Gly
305                 310                 315                 320

Leu Tyr Gln Gly Leu Ser Thr Ala Thr Lys Asp Thr Tyr Asp Ala Leu
                325                 330                 335

His Met Gln Ala Leu Pro Pro Arg Arg Ala Glu Gly Arg Gly Ser Leu
                340                 345                 350

Leu Thr Cys Gly Asp Val Glu Glu Asn Pro Gly Pro Met Glu Thr Asp
            355                 360                 365

Thr Leu Leu Leu Trp Val Leu Leu Leu Trp Val Pro Gly Ser Thr Gly
    370                 375                 380

Asp Ile Gln Met Thr Gln Thr Thr Ser Ser Leu Ser Ala Ser Leu Gly
385                 390                 395                 400

Asp Arg Val Thr Ile Ser Cys Arg Ala Ser Gln Asp Ile Ser Lys Tyr
                405                 410                 415

Leu Asn Trp Tyr Gln Gln Lys Pro Asp Gly Thr Val Lys Leu Leu Ile
            420                 425                 430

Tyr His Thr Ser Arg Leu His Ser Gly Val Pro Ser Arg Phe Ser Gly
        435                 440                 445

Ser Gly Ser Gly Thr Asp Tyr Ser Leu Thr Ile Ser Asn Leu Glu Gln
    450                 455                 460

Glu Asp Ile Ala Thr Tyr Phe Cys Gln Gln Gly Asn Thr Leu Pro Tyr
465                 470                 475                 480

Thr Phe Gly Gly Gly Thr Lys Leu Glu Ile Thr Lys Ala Gly Gly Gly
                485                 490                 495

Gly Ser Gly Gly Gly Gly Ser Gly Gly Gly Gly Ser Gly Gly Gly Gly
            500                 505                 510

Ser Glu Val Lys Leu Gln Glu Ser Gly Pro Gly Leu Val Ala Pro Ser
        515                 520                 525

Gln Ser Leu Ser Val Thr Cys Thr Val Ser Gly Val Ser Leu Pro Asp
    530                 535                 540

Tyr Gly Val Ser Trp Ile Arg Gln Pro Pro Arg Lys Gly Leu Glu Trp
545                 550                 555                 560

Leu Gly Val Ile Trp Gly Ser Glu Thr Thr Tyr Tyr Asn Ser Ala Leu
                565                 570                 575

Lys Ser Arg Leu Thr Ile Ile Lys Asp Asn Ser Lys Ser Gln Val Phe
            580                 585                 590
```

Leu Lys Met Asn Ser Leu Gln Thr Asp Asp Thr Ala Ile Tyr Tyr Cys
            595                 600                 605

Ala Lys His Tyr Tyr Gly Gly Ser Tyr Ala Met Asp Tyr Trp Gly
            610                 615                 620

Gln Gly Thr Ser Val Thr Val Ser Ser Asp Pro Ala Glu Pro Lys Ser
625                 630                 635                 640

Pro Asp Lys Thr His Thr Cys Pro Pro Cys Pro Ala Pro Pro Val Ala
                    645                 650                 655

Gly Pro Ser Val Phe Leu Phe Pro Pro Lys Pro Lys Asp Thr Leu Met
                660                 665                 670

Ile Ala Arg Thr Pro Glu Val Thr Cys Val Val Val Asp Val Ser His
            675                 680                 685

Glu Asp Pro Glu Val Lys Phe Asn Trp Tyr Val Asp Gly Val Glu Val
690                 695                 700

His Asn Ala Lys Thr Lys Pro Arg Glu Glu Gln Tyr Asn Ser Thr Tyr
705                 710                 715                 720

Arg Val Val Ser Val Leu Thr Val Leu His Gln Asp Trp Leu Asn Gly
                    725                 730                 735

Lys Glu Tyr Lys Cys Lys Val Ser Asn Lys Ala Leu Pro Ala Pro Ile
                740                 745                 750

Glu Lys Thr Ile Ser Lys Ala Lys Gly Gln Pro Arg Glu Pro Gln Val
            755                 760                 765

Tyr Thr Leu Pro Pro Ser Arg Asp Glu Leu Thr Lys Asn Gln Val Ser
770                 775                 780

Leu Thr Cys Leu Val Lys Gly Phe Tyr Pro Ser Asp Ile Ala Val Glu
785                 790                 795                 800

Trp Glu Ser Asn Gly Gln Pro Glu Asn Asn Tyr Lys Thr Thr Pro Pro
                    805                 810                 815

Val Leu Asp Ser Asp Gly Ser Phe Phe Leu Tyr Ser Lys Leu Thr Val
                820                 825                 830

Asp Lys Ser Arg Trp Gln Gln Gly Asn Val Phe Ser Cys Ser Val Met
            835                 840                 845

His Glu Ala Leu His Asn His Tyr Thr Gln Lys Ser Leu Ser Leu Ser
850                 855                 860

Pro Gly Lys Lys Asp Pro Met Ala Leu Ile Val Leu Gly Gly Val Ala
865                 870                 875                 880

Gly Leu Leu Leu Phe Ile Gly Leu Gly Ile Phe Phe Cys Val Arg Cys
                    885                 890                 895

Arg His Arg Arg Arg Gln Ala Glu Arg Met Ala Gln Ile Lys Arg Val
                900                 905                 910

Val Ser Glu Lys Lys Thr Ala Gln Ala Pro His Arg Phe Gln Lys Thr
            915                 920                 925

Cys Ser Pro Ile Ser Gly Gly Gly Ser Arg Pro Glu Cys Val Val
930                 935                 940

Pro Glu Thr Gln Cys Ala Met Lys Arg Lys Glu Lys Lys Ala Gln Lys
945                 950                 955                 960

Glu Lys Asp Lys Leu Pro Val Ser Thr Thr Thr Val Asp Asp His Met
                    965                 970                 975

Pro Pro Ile Met Gln Cys Glu Pro Pro Pro Glu Ala Ala Arg Ile
                980                 985                 990

His Glu Val Val Pro Arg Phe Leu  Ser Asp Lys Leu  Leu Glu Thr Asn
            995                 1000                1005

-continued

```
Arg Gln Lys Asn Ile Pro Gln Leu Thr Ala Asn Gln Gln Phe Leu
    1010                1015                1020

Ile Ala Arg Leu Ile Trp Tyr Gln Asp Gly Tyr Glu Gln Pro Ser
    1025                1030                1035

Asp Glu Asp Leu Lys Arg Ile Thr Gln Thr Trp Gln Gln Ala Asp
    1040                1045                1050

Asp Glu Asn Glu Glu Ser Asp Thr Pro Phe Arg Gln Ile Thr Glu
    1055                1060                1065

Met Thr Ile Leu Thr Val Gln Leu Ile Val Glu Phe Ala Lys Gly
    1070                1075                1080

Leu Pro Gly Phe Ala Lys Ile Ser Gln Pro Asp Gln Ile Thr Leu
    1085                1090                1095

Leu Lys Ala Cys Ser Ser Glu Val Met Met Leu Arg Val Ala Arg
    1100                1105                1110

Arg Tyr Asp Ala Ala Ser Asp Ser Ile Leu Phe Ala Asn Asn Gln
    1115                1120                1125

Ala Tyr Thr Arg Asp Asn Tyr Arg Lys Ala Gly Met Ala Glu Val
    1130                1135                1140

Ile Glu Asp Leu Leu His Phe Cys Arg Cys Met Tyr Ser Met Ala
    1145                1150                1155

Leu Asp Asn Ile His Tyr Ala Leu Leu Thr Ala Val Val Ile Phe
    1160                1165                1170

Ser Asp Arg Pro Gly Leu Glu Gln Pro Gln Leu Val Glu Glu Ile
    1175                1180                1185

Gln Arg Tyr Tyr Leu Asn Thr Leu Arg Ile Tyr Ile Leu Asn Gln
    1190                1195                1200

Leu Ser Gly Ser Ala Arg Ser Ser Val Ile Tyr Gly Lys Ile Leu
    1205                1210                1215

Ser Ile Leu Ser Glu Leu Arg Thr Leu Gly Met Gln Asn Ser Asn
    1220                1225                1230

Met Cys Ile Ser Leu Lys Leu Lys Asn Arg Lys Leu Pro Pro Phe
    1235                1240                1245

Leu Glu Glu Ile Trp Asp Val Ala Asp Met Ser His Thr Gln Pro
    1250                1255                1260

Pro Pro Ile Leu Glu Ser Pro Thr Asn Leu
    1265                1270

<210> SEQ ID NO 24
<211> LENGTH: 919
<212> TYPE: PRT
<213> ORGANISM: Artificial Sequence
<220> FEATURE:
<223> OTHER INFORMATION: Simple inducible CAR

<400> SEQUENCE: 24

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
                20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80
```

-continued

```
Tyr Ala Tyr Gly Ala Thr Gly His Pro Gly Ile Ile Pro Pro His Ala
                85                  90                  95
Thr Leu Val Phe Asp Val Glu Leu Leu Lys Leu Glu Ser Gly Gly Gly
            100                 105                 110
Ser Ala Asp Ala Pro Ala Tyr Gln Gln Gly Gln Asn Gln Leu Tyr Asn
        115                 120                 125
Glu Leu Asn Leu Gly Arg Arg Glu Glu Tyr Asp Val Leu Asp Lys Arg
    130                 135                 140
Arg Gly Arg Asp Pro Glu Met Gly Gly Lys Pro Arg Arg Lys Asn Pro
145                 150                 155                 160
Gln Glu Gly Leu Tyr Asn Glu Leu Gln Lys Asp Lys Met Ala Glu Ala
                165                 170                 175
Tyr Ser Glu Ile Gly Met Lys Gly Glu Arg Arg Arg Gly Lys Gly His
            180                 185                 190
Asp Gly Leu Tyr Gln Gly Leu Ser Thr Ala Thr Lys Asp Thr Tyr Asp
        195                 200                 205
Ala Leu His Met Gln Ala Leu Pro Pro Arg Arg Ala Glu Gly Arg Gly
    210                 215                 220
Ser Leu Leu Thr Cys Gly Asp Val Glu Glu Asn Pro Gly Pro Met Glu
225                 230                 235                 240
Thr Asp Thr Leu Leu Leu Trp Val Leu Leu Leu Trp Val Pro Gly Ser
                245                 250                 255
Thr Gly Asp Ile Gln Met Thr Gln Thr Thr Ser Ser Leu Ser Ala Ser
            260                 265                 270
Leu Gly Asp Arg Val Thr Ile Ser Cys Arg Ala Ser Gln Asp Ile Ser
        275                 280                 285
Lys Tyr Leu Asn Trp Tyr Gln Gln Lys Pro Asp Gly Thr Val Lys Leu
    290                 295                 300
Leu Ile Tyr His Thr Ser Arg Leu His Ser Gly Val Pro Ser Arg Phe
305                 310                 315                 320
Ser Gly Ser Gly Ser Gly Thr Asp Tyr Ser Leu Thr Ile Ser Asn Leu
                325                 330                 335
Glu Gln Glu Asp Ile Ala Thr Tyr Phe Cys Gln Gln Gly Asn Thr Leu
            340                 345                 350
Pro Tyr Thr Phe Gly Gly Gly Thr Lys Leu Glu Ile Thr Lys Ala Gly
        355                 360                 365
Gly Gly Gly Ser Gly Gly Gly Gly Ser Gly Gly Gly Gly Ser Gly Gly
    370                 375                 380
Gly Gly Ser Glu Val Lys Leu Gln Glu Ser Gly Pro Gly Leu Val Ala
385                 390                 395                 400
Pro Ser Gln Ser Leu Ser Val Thr Cys Thr Val Ser Gly Val Ser Leu
                405                 410                 415
Pro Asp Tyr Gly Val Ser Trp Ile Arg Gln Pro Pro Arg Lys Gly Leu
            420                 425                 430
Glu Trp Leu Gly Val Ile Trp Gly Ser Glu Thr Thr Tyr Tyr Asn Ser
        435                 440                 445
Ala Leu Lys Ser Arg Leu Thr Ile Ile Lys Asp Asn Ser Lys Ser Gln
    450                 455                 460
Val Phe Leu Lys Met Asn Ser Leu Gln Thr Asp Asp Thr Ala Ile Tyr
465                 470                 475                 480
Tyr Cys Ala Lys His Tyr Tyr Tyr Gly Gly Ser Tyr Ala Met Asp Tyr
                485                 490                 495
Trp Gly Gln Gly Thr Ser Val Thr Val Ser Ser Asp Pro Ala Glu Pro
```

```
                500                 505                 510
Lys Ser Pro Asp Lys Thr His Thr Cys Pro Cys Pro Ala Pro Pro
        515                 520                 525

Val Ala Gly Pro Ser Val Phe Leu Phe Pro Lys Pro Lys Asp Thr
        530                 535                 540

Leu Met Ile Ala Arg Thr Pro Glu Val Thr Cys Val Val Val Asp Val
545                 550                 555                 560

Ser His Glu Asp Pro Glu Val Lys Phe Asn Trp Tyr Val Asp Gly Val
                565                 570                 575

Glu Val His Asn Ala Lys Thr Lys Pro Arg Glu Glu Gln Tyr Asn Ser
            580                 585                 590

Thr Tyr Arg Val Val Ser Val Leu Thr Val Leu His Gln Asp Trp Leu
        595                 600                 605

Asn Gly Lys Glu Tyr Lys Cys Lys Val Ser Asn Lys Ala Leu Pro Ala
        610                 615                 620

Pro Ile Glu Lys Thr Ile Ser Lys Ala Lys Gly Gln Pro Arg Glu Pro
625                 630                 635                 640

Gln Val Tyr Thr Leu Pro Pro Ser Arg Asp Glu Leu Thr Lys Asn Gln
                645                 650                 655

Val Ser Leu Thr Cys Leu Val Lys Gly Phe Tyr Pro Ser Asp Ile Ala
                660                 665                 670

Val Glu Trp Glu Ser Asn Gly Gln Pro Glu Asn Asn Tyr Lys Thr Thr
        675                 680                 685

Pro Pro Val Leu Asp Ser Asp Gly Ser Phe Phe Leu Tyr Ser Lys Leu
        690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
                725                 730                 735

Leu Ser Pro Gly Lys Lys Asp Pro Met Ala Leu Ile Val Leu Gly Gly
                740                 745                 750

Val Ala Gly Leu Leu Leu Phe Ile Gly Leu Gly Ile Phe Phe Cys Val
        755                 760                 765

Arg Cys Arg His Arg Arg Gln Ala Glu Arg Met Ala Gln Ile Lys
        770                 775                 780

Arg Val Val Ser Glu Lys Lys Thr Ala Gln Ala Pro His Arg Phe Gln
785                 790                 795                 800

Lys Thr Cys Ser Pro Ile Ser Gly Gly Gly Ser Gly Val Gln Val
                805                 810                 815

Glu Thr Ile Ser Pro Gly Asp Gly Arg Thr Phe Pro Lys Arg Gly Gln
                820                 825                 830

Thr Cys Val Val His Tyr Thr Gly Met Leu Glu Asp Gly Lys Lys Val
            835                 840                 845

Asp Ser Ser Arg Asp Arg Asn Lys Pro Phe Lys Phe Met Leu Gly Lys
        850                 855                 860

Gln Glu Val Ile Arg Gly Trp Glu Glu Gly Val Ala Gln Met Ser Val
865                 870                 875                 880

Gly Gln Arg Ala Lys Leu Thr Ile Ser Pro Asp Tyr Ala Tyr Gly Ala
                885                 890                 895

Thr Gly His Pro Gly Ile Ile Pro Pro His Ala Thr Leu Val Phe Asp
        900                 905                 910

Val Glu Leu Leu Lys Leu Glu
        915
```

<210> SEQ ID NO 25
<211> LENGTH: 234
<212> TYPE: PRT
<213> ORGANISM: Artificial Sequence
<220> FEATURE:
<223> OTHER INFORMATION: CID binding domain - EcR

<400> SEQUENCE: 25

Met Pro Val Asp Arg Ile Leu Glu Ala Glu Leu Ala Val Glu Gln Lys
1               5                   10                  15

Ser Asp Gln Gly Val Glu Gly Pro Gly Gly Thr Gly Gly Ser Gly Ser
                20                  25                  30

Ser Pro Asn Asp Pro Val Thr Asn Ile Cys Gln Ala Ala Asp Lys Gln
            35                  40                  45

Leu Phe Thr Leu Val Glu Trp Ala Lys Arg Ile Pro His Phe Ser Ser
    50                  55                  60

Leu Pro Leu Asp Asp Gln Val Ile Leu Leu Arg Ala Gly Trp Asn Glu
65                  70                  75                  80

Leu Leu Ile Ala Ser Phe Ser His Arg Ser Ile Asp Val Arg Asp Gly
                85                  90                  95

Ile Leu Leu Ala Thr Gly Leu His Val His Arg Asn Ser Ala His Ser
            100                 105                 110

Ala Gly Val Gly Ala Ile Phe Asp Arg Val Leu Thr Glu Leu Val Ser
        115                 120                 125

Lys Met Arg Asp Met Arg Met Asp Lys Thr Glu Leu Gly Cys Leu Arg
130                 135                 140

Ala Ile Ile Leu Phe Asn Pro Glu Val Arg Gly Leu Lys Ser Ala Gln
145                 150                 155                 160

Glu Val Glu Leu Leu Arg Glu Lys Val Tyr Ala Ala Leu Glu Glu Tyr
                165                 170                 175

Thr Arg Thr Thr His Pro Asp Glu Pro Gly Arg Phe Ala Lys Leu Leu
            180                 185                 190

Leu Arg Leu Pro Ser Leu Arg Ser Ile Gly Leu Lys Cys Leu Glu His
        195                 200                 205

Leu Phe Phe Phe Arg Leu Ile Gly Asp Val Pro Ile Asp Thr Phe Leu
    210                 215                 220

Met Glu Met Leu Glu Ser Pro Ser Asp Ser
225                 230

<210> SEQ ID NO 26
<211> LENGTH: 335
<212> TYPE: PRT
<213> ORGANISM: Artificial Sequence
<220> FEATURE:
<223> OTHER INFORMATION: CID binding domain - RXR

<400> SEQUENCE: 26

Arg Pro Glu Cys Val Val Pro Thr Gln Cys Ala Met Lys Arg Lys
1               5                   10                  15

Glu Lys Lys Ala Gln Lys Glu Lys Asp Lys Leu Pro Val Ser Thr Thr
                20                  25                  30

Thr Val Asp Asp His Met Pro Pro Ile Met Gln Cys Glu Pro Pro Pro
            35                  40                  45

Pro Glu Ala Ala Arg Ile His Glu Val Pro Arg Phe Leu Ser Asp
        50                  55                  60

Lys Leu Leu Glu Thr Asn Arg Gln Lys Asn Ile Pro Gln Leu Thr Ala

-continued

```
            65                  70                  75                  80
Asn Gln Gln Phe Leu Ile Ala Arg Leu Ile Trp Tyr Gln Asp Gly Tyr
                    85                  90                  95

Glu Gln Pro Ser Asp Glu Asp Leu Lys Arg Ile Thr Gln Thr Trp Gln
                    100                 105                 110

Gln Ala Asp Asp Glu Asn Glu Glu Ser Asp Thr Pro Phe Arg Gln Ile
                    115                 120                 125

Thr Glu Met Thr Ile Leu Thr Val Gln Leu Ile Val Glu Phe Ala Lys
                    130                 135                 140

Gly Leu Pro Gly Phe Ala Lys Ile Ser Gln Pro Asp Gln Ile Thr Leu
145                 150                 155                 160

Leu Lys Ala Cys Ser Ser Glu Val Met Met Leu Arg Val Ala Arg Arg
                    165                 170                 175

Tyr Asp Ala Ala Ser Asp Ser Ile Leu Phe Ala Asn Asn Gln Ala Tyr
                    180                 185                 190

Thr Arg Asp Asn Tyr Arg Lys Ala Gly Met Ala Glu Val Ile Glu Asp
                    195                 200                 205

Leu Leu His Phe Cys Arg Cys Met Tyr Ser Met Ala Leu Asp Asn Ile
            210                 215                 220

His Tyr Ala Leu Leu Thr Ala Val Val Ile Phe Ser Asp Arg Pro Gly
225                 230                 235                 240

Leu Glu Gln Pro Gln Leu Val Glu Glu Ile Gln Arg Tyr Tyr Leu Asn
                    245                 250                 255

Thr Leu Arg Ile Tyr Ile Leu Asn Gln Leu Ser Gly Ser Ala Arg Ser
                    260                 265                 270

Ser Val Ile Tyr Gly Lys Ile Leu Ser Ile Leu Ser Glu Leu Arg Thr
            275                 280                 285

Leu Gly Met Gln Asn Ser Asn Met Cys Ile Ser Leu Lys Leu Lys Asn
            290                 295                 300

Arg Lys Leu Pro Pro Phe Leu Glu Glu Ile Trp Asp Val Ala Asp Met
305                 310                 315                 320

Ser His Thr Gln Pro Pro Ile Leu Glu Ser Pro Thr Asn Leu
                    325                 330                 335
```